(12) United States Patent
Jung et al.

(10) Patent No.: US 9,718,893 B2
(45) Date of Patent: Aug. 1, 2017

(54) BISPECIFIC ANTIBODY MOLECULE

(71) Applicant: SYNIMMUNE GMBH, Tuebingen (DE)

(72) Inventors: Gundram Jung, Rottenburg-Wendelsheim (DE); Michael Durben, Tuebingen (DE); Ludger Grosse-Hovest, Tuebingen (DE)

(73) Assignee: SYNIMMUNE GMBH, Tuebingen (DE)

( * ) Notice: Subject to any disclaimer, the term of this patent is extended or adjusted under 35 U.S.C. 154(b) by 0 days.

(21) Appl. No.: 14/366,669

(22) PCT Filed: Nov. 12, 2012

(86) PCT No.: PCT/EP2012/072364
§ 371 (c)(1),
(2) Date: Jun. 18, 2014

(87) PCT Pub. No.: WO2013/092001
PCT Pub. Date: Jun. 27, 2013

(65) Prior Publication Data
US 2015/0119555 A1    Apr. 30, 2015

Related U.S. Application Data

(60) Provisional application No. 61/577,327, filed on Dec. 19, 2011.

(51) Int. Cl.
*C07K 16/46* (2006.01)
*C07K 16/28* (2006.01)
*C07K 16/30* (2006.01)

(52) U.S. Cl.
CPC ........ *C07K 16/468* (2013.01); *C07K 16/2803* (2013.01); *C07K 16/283* (2013.01); *C07K 16/2809* (2013.01); *C07K 16/2818* (2013.01); *C07K 16/2863* (2013.01); *C07K 16/2866* (2013.01); *C07K 16/3015* (2013.01); *C07K 16/3053* (2013.01); *C07K 2317/31* (2013.01); *C07K 2317/522* (2013.01); *C07K 2317/524* (2013.01); *C07K 2317/526* (2013.01); *C07K 2317/55* (2013.01); *C07K 2317/622* (2013.01)

(58) Field of Classification Search
CPC .............. C07K 16/468; C07K 16/2809; C07K 2317/522; C07K 2317/31; C07K 2317/524; C07K 2317/55; C07K 2317/622
USPC ...................................................... 530/387.3
See application file for complete search history.

(56) References Cited

U.S. PATENT DOCUMENTS

2014/0314764 A1*  10/2014  Jung et al. ................. 424/136.1

FOREIGN PATENT DOCUMENTS

| WO | 2006031994 A2 | 3/2006 |
| WO | 2006116260 A2 | 11/2006 |
| WO | 2007109254 A2 | 9/2007 |
| WO | 2009018386 A1 | 2/2009 |
| WO | 2009155513 A2 | 12/2009 |
| WO | 2011025964 A2 | 3/2011 |
| WO | 2011047180 A1 | 4/2011 |

OTHER PUBLICATIONS

Ibragimova and Eade (Biophysical Journal, (Oct. 1999), vol. 77, pp. 2191-2198).*
Salfeld (Nature Biotech. 25(12): 1369-1372 (2007)).*
Dall'Acqua (J. Immunol. 177:1129-1138 (2006).*
Medical dictionary.thefreedictionary definition for "attenuation" (pp. 1-4; Dec. 1, 2016).*
International Search Report issued Apr. 11, 2013 in PCT/EP2012/072364 (5 pages).
Lu et al., "Fab-scFv fusion protein: an efficient approach to production of bispecific antibody fragments", Journal of Immunological Methods. Elsevier Science Publishers B.V ., 267(2):213-226, 2002.
Seifert et al., "The IgM CH2 domain as covalently linked homodimerization module for the generation of fusion proteins with dual specificity", Protein Engineering, Design and Selection, 25(10):603-612, 2012 (Sep. 17, 2012).
Baudino et al., "Impact of a three amino acid deletion in the CH2 domain of murine IgG1 on Fc-associated effector functions", The Journal of Immunology, 181(6):4107-4112, 2008.
Baudino et al., "Crucial role of aspartic acid at position 265 in the CH2 domain for murine IgG2a and IgG2b Fc-associated effector functions", The Journal of Immunology, 181(9):6664-6669, 2008.
Chames and Baty, "Bispecific antibodies for cancer therapy: the light at the end of the tunnel?", MAbs. Nov.-Dec. 2009;1(6):539-47. Review.
Gergely and Sarmay, "The two binding-site models of human IgG binding Fc gamma receptors", FASEB J. Dec. 1990;4(15):3275-83.
Thakur and Lum, "Cancer therapy with bispecific antibodies: Clinical experience", Curr Opin Mol Ther. Jun. 2010;12(3):340-9. Review.
Wines et al., "The IgG Fc contains distinct Fc receptor (FcR) binding sites: the leukocyte receptors Fc gamma RI and Fc gamma RIIa bind to a region in the Fc distinct from that recognized by neonatal FcR and protein A", J Immunol. May 15, 2000;164(10):5313-8.
Durben et al., "Characterization of a bispecific FLT3 X CD3 antibody in an improved, recombinant format for the treatment of leukemia", Mol Ther. Apr. 2015;23(4):648-55. doi: 10.1038/mt.2015.2. Epub Jan. 12, 2015.
Yates Z et al. "Histidine residue mediates radical-induced hinge cleavage of human IgG1". J Biol Chem. Jun. 11, 2010;285(24):18662-71. Epub Mar. 19, 2010.
Rob C Aalberse and Janine Schuurman "IgG4 breaking the rules Immunology". Jan. 2002; 105(1): 9-19.

(Continued)

*Primary Examiner* — Lynn Bristol
(74) *Attorney, Agent, or Firm* — Acuity Law Group, PC; Michael Whittaker

(57) ABSTRACT

The present invention relates to a bispecific antibody molecule, as well as a method for producing the same, its use and a nucleic acid molecule encoding the bispecific antibody molecule. The invention in particular provides an antibody molecule that is capable of mediating target cell restricted activation of immune cells.

13 Claims, 21 Drawing Sheets

(56) References Cited

OTHER PUBLICATIONS

Bloom JW et al. "Intrachain disulfide bond in the core hinge region of human IgG4". Protein Sci. Feb. 1997;6(2):407-15.
Yan et al. "Engineering upper hinge improves stability and effector function of a human JgGJ". J Biol Chem. Feb. 17, 2012;287(8):5891-7. Epub Dec. 27, 2011.
Communication pursuant to Rule 114(2) EPC, third party observations, dated Oct. 13, 2016 in European patent application 12 798 623.0 (6 pages).

* cited by examiner

H)

I)

J)

K)

L)

M)

N)

bsFc-CH₃-1/2

O)

Modification for bsFc-½-format*

| | CH₁ ⇒ | | | functional hinge | | | | | | | | | | | CH₂ | | | | |
|---|---|---|---|---|---|---|---|---|---|---|---|---|---|---|---|---|---|---|---|
| | | | | upper genetic hinge ⇒ | | | core ⇒ | | lower | | | | | | | | | | |
| IgGγ1 (wt) | K | K | V | E P K S C D K T | H T | C | P P C | P | A P E L | L | G G P | S | V F L | ...//... | D | N | A | A |
| **Position | 215 | | | | 220 | 226 | 229 | 233 | 234 | 235 | 236 237 238 | 239 | 242 | | 265 | 297 | 327 | 330 |
| bsFc-½ | | | | | | s | s | | | | | | | | | | | |
| Δ₁ | | | | | | s | s | | | | | | | | G | Q | Q | S |
| Glycan | | | | | | s | — | | | | — — — | | | | G | Q | Q | S |
| Δ₂ | | | | | | s | — | P | P | V | A — — | | | | G | Q | Q | S |
| Δ₃ | | | | | | s | — | — | — | V | A — — | | | | G | Q | Q | S |
| Δ₄ | | | | | | s | — | P | P | V | A — — | | | | G | Q | Q | S |
| Δ₅ | | | | | | s | — | — | — | — | — — — | | | | G | Q | Q | S |

*Does also apply to the bsFc^ko – CH₃ – ½-format (Fig. 1N).
**The positional numbering of amino acids is according to the EU-index.

Modification for bsFc-1-format*

| | CH$_1$ ⟹ | | | | | | upper genetic hinge | | | | | functional hinge core ⟹ | | | | | lower | | | | | ⟹ CH$_2$ | | | | | | | |
|---|---|---|---|---|---|---|---|---|---|---|---|---|---|---|---|---|---|---|---|---|---|---|---|---|---|---|---|---|---|---|
| Igγ1 (wt) | K | K | V | E | P | K | S | C | D | K | T | H | T | C | P | P | C | P | A | P | E | L | L | G | G | P | S | V | F | L .../.... D N A A |
| **Position | | | 215 | | | | | 220 | | | | | | 226 | | | 229 | | | | 233 | 234 | 235 | 236 | 237 | 238 | 239 | | 242 | 265  297  327  330 |
| bsFc-1 | | | | | | | | | | | | | | | | | | | | | | | | | | | | | | | |
| Δ$_1$ | | | | | | | | | | | | | | | | | | | | | | P | V | A | — | — | — | | | | G    Q    Q    S |
| Glycan | | | | | | | | | | | | | | | | | | | | | | | | | | | | | | | G    Q    Q    S |
| Δ$_2$ | | | | | | | | | | | | | | | | | | | | | | P | V | A | — | — | — | | | | G    Q    Q    S |
| Δ$_3$ | | | | | | | | | | | | | | | | | | | | | | — | V | A | — | — | — | | | | G    Q    Q    S |
| Δ$_4$ | | | | | | | | | | | | | | | | | | | | | | P | V | A | — | — | — | | | | G    Q    Q    S |
| Δ$_5$ | | | | | | | | | | | | | | | | | | | | | | — | — | — | — | — | — | | | | G    Q    Q    S |

*Does also apply to the bsFc-½-dimer-format (Fig. 1F).
**The positional numbering of amino acids is according to the EU-index.

D)

E

F

Target cell restricted T-cell activation

Specific lysis of tumor cells

A)

B)

A) Size exclusion chromatography

Specificity:

FLT3xCD3

B) Production rates

Fig. 6

A) light chain sequences

1) Anti-FLT3 chimeric light chain (clone 4G8): (SEQ ID NO: 1)

DIVLTQSPATLSVTPGDSVSLSC<u>RASQSISNNL</u>HWYQQKSHESPRLLIK<u>YASQSIS</u>**GIPSRFSGS
GSGTDFTLSINSVETEDFGVYFC<u>QQSNTWPYT</u>FGGGTKLEIK***RTVAAPSVFIFPPSDEQLKSGTA
SVVCLLNNFYPREAKVQWKVDNALQSGNSQESVTEQDSKDSTYSLSSTLTLSKADYEKHKVYAC
EVTHQGLSSPVTKSFNRGEC\**

2) Anti-FLT3 chimeric light chain (clone BV10): (SEQ ID NO: 2)

DIVMTQSPSSLSVSAGEKVTMSC<u>KSSQSLLNSGNQKNYMA</u>WYQQKPGQPPKLLIY<u>GASTRES</u>
GVPDRFTGSGSGTDFTLTISSVQAEDLAVYYC<u>QNDHSYPLT</u>FGAGTKLELK*RTVAAPSVFIFPPS
DEQLKSGTASVVCLLNNFYPREAKVQWKVDNALQSGNSQESVTEQDSKDSTYSLSSTLTLSKAD
YEKHKVYACEVTHQGLSSPVTKSFNRGEC\**

3) Anti-CSPG4 chimeric light chain (clone 9.2.27): (SEQ ID NO: 3)

DIELTQSPASLAVSLGQRATISC<u>RASESVDSYGNSFMH</u>WYQQKPGQPPKLLIY<u>LASNLES</u>**GVPA
RFSGSGSRTDFTLTIDPVEADDAATYYC<u>QQNNEDPLT</u>FGGGTKLEIK***RTVAAPSVFIFPPSDEQL
KSGTASVVCLLNNFYPREAKVQWKVDNALQSGNSQESVTEQDSKDSTYSLSSTLTLSKADYEKH
KVYACEVTHQGLSSPVTKSFNRGEC\**

Anti-CD19 chimeric light (clone 4G7) (SEQ ID NO: 4)

DIVMTQAAPSIPVTPGESVSISC<u>RSSKSLLNSNGNTYLY</u>WFLQRPGQSPQLLIY<u>RMSNLAS</u>**GVP
DRFSGSGSGTAFTLRISRVEAEDVGVYYC<u>MQHLEYPFT</u>FGAGTKLELK***RTVAAPSVFIFPPSDE
QLKSGTASVVCLLNNFYPREAKVQWKVDNALQSGNSQESVTEQDSKDSTYSLSSTLTLSKADYE
KHKVYACEVTHQGLSSPVTKSFNRGEC\**

5) Anti-EGFR light chain (clone C225) (SEQ ID NO: 5)

DILLTQSPVILSVSPGERVSFSC<u>RASQSIGTNIH</u>WYQQRTNGSPRLLIK<u>YASESIS</u>**GIPSRFSGSG
SGTDFTLSINSVESEDIADYYC<u>QQNNNWPTT</u>FGAGTKLELK***RTVAAPSVFIFPPSDEQLKSGTAS
VVCLLNNFYPREAKVQWKVDNALQSGNSQESVTEQDSKDSTYSLSSTLTLSKADYEKHKVYACE
VTHQGLSSPVTKSFNRGEC\**

Fig. 6 CONT.

B) heavy chain/main chain sequences

1) FLT3 x CD3; bsFc$^{ko}$-1/2 [N-terminal anti-FLT3 chimeric heavy chain (clone 4G8) and C-terminal CD3 single-chain (clone UCHT1; VL-VH orientation)], being a chain of a glycan-ko-variant-halfmolecule (SEQ ID NO: 6)

QVQLQQPGAELVKPGASLKLSCKSSGYTFTSYWMHWVRQRPGHGLEWIGEIDPSDSYKDYNQ
KFKDKATLTVDRSSNTAYMHLSSLTSDDSAVYYCARAITTTPFDFWGQGTTLTVSS**ASTKGPSV
FPLAPSSKSTSGGTAALGCLVKDYFPEPVTVSWNSGALTSGVHTFPAVLQSSGLYSLSSVVTVP
SSSLGTQTYICNVNHKPSNTKVDKKV**EPKSCDKTHTSPPSPAPPVAGPSVFLFPPKPKDTLMISR
TPEVTCVVVGVSHEDPEVKFNWYVDGVEVHNAKTKPREEQYQSTYRVVSVLTVLHQDWLNGKE
YKCKVSNKQLPSPIEKTISKAK**G*QPSG*DIQMTQSPSSLSASVGDRVTITC*RASQDIRNYL*NWYQQ
KPGKAPKLLIY*YTSRLES*GVPSRFSGSGSGTDYTLTISSLQPEDFATYYC*QQGNTLPW*TFGQGT
KVEIK*GGGGSGGGGSGGGGS*EVQLVESGGGLVQPGGSLRLSCAASGYSFT*GYTMN*WVRQAP
GKGLEWVA*LINPYKGVSTYNQKFKD*RFTISVDKSKNTAYLQMNSLRAEDTAVYYCAR*SGYYGD
SDWYFDV*WGQGTLVTVSS***

2) FLT3 x CD3; bsFc$^{ko}$-1/2 [N-terminal anti-FLT3 chimeric heavy chain (clone BV10) and C-terminal CD3 single-chain (clone UCHT1; VL-VH orientation)], being a chain of a glycan-ko-variant-halfmolecule (SEQ ID NO: 7)

QVQLKQSGPGLVQPSQSLSITCTVSGFSLTNYGLHWVRQSPGKGLEWLGVIWSGGSTDYNAA
FISRLSISKDNSKSQVFFKMNSLQADDTAIYYCARKGGIYYANHYYAMDYWGQGTSVTVSS**AST
KGPSVFPLAPSSKSTSGGTAALGCLVKDYFPEPVTVSWNSGALTSGVHTFPAVLQSSGLYSLSS
VVTVPSSSLGTQTYICNVNHKPSNTKVDKKV**EPKSCDKTHTSPPSPAPPVAGPSVFLFPPKPKDT
LMISRTPEVTCVVVGVSHEDPEVKFNWYVDGVEVHNAKTKPREEQYQSTYRVVSVLTVLHQDW
LNGKEYKCKVSNKQLPSPIEKTISKAK**G*QPSG*DIQMTQSPSSLSASVGDRVTITC*RASQDIRNYL
NWYQQKPGKAPKLLIY*YTSRLES*GVPSRFSGSGSGTDYTLTISSLQPEDFATYYC*QQGNTLPW
TFGQGTKVEIK*GGGGSGGGGSGGGGS*EVQLVESGGGLVQPGGSLRLSCAASGYSFT*GYTMN*
WVRQAPGKGLEWVA*LINPYKGVSTYNQKFKD*RFTISVDKSKNTAYLQMNSLRAEDTAVYYCA
R*SGYYGDSDWYFDV*WGQGTLVTVSS***

Fig. 6 CONT.

3) FLT3 x TCRα/β; bsFc$^{ko}$-1/2 [N-terminal anti-FLT3 chimeric heavy chain (clone 4G8) and C-terminal TCRα/β single-chain (clone BMA031; VH-VL orientation)], being a chain of a glycan-ko-variant-halfmolecule (SEQ ID NO: 8)

QVQLQQPGAELVKPGASLKLSCKSSGYTFT<u>SYWMH</u>WVRQRPGHGLEWIG<u>EIDPSDSYKDYNQ
KFKDKATLTVDRSSNTAYMHLSSLTSDDSAVYYCAR<u>AITTTPFDF</u>WGQGTTLTVSSASTKGPSV
FPLAPSSKSTSGGTAALGCLVKDYFPEPVTVSWNSGALTSGVHTFPAVLQSSGLYSLSSVVTV
PSSSLGTQTYICNVNHKPSNTKVDKKV</u>EPKSCDKTHTSPPSPAPPVAGPSVFLFPPKPKDTLMIS
RTPEVTCVVVGVSHEDPEVKFNWYVDGVEVHNAKTKPREEQYQSTYRVVSVLTVLHQDWLNGK
EYKCKVSNKQLPSPIEKTISKAK*GQPSG*EVQLQQSGPELVKPGASVKMSCKASGYKFT<u>SYVMH</u>
WVKQKPGQGLEWIG<u>YINPYNDVTKYNEKFKG</u>KATLTSDKSSSTAYMELSSLTSEDSAVHYCAR
<u>GSYYDYDGFVY</u>GQGTLVTVSS*GGGGSGGGGSGGGGS*QIVLTQSPAIMSASPGEKVTMTC*SAT
SSVSYMH*WYQQKSGTSPKRWIY*DTSKLAS*GVPARFSGSGSGTSYSLTISSMEAEDAATYYC*Q
QWSSNPLT*FGAGTKLELK\*

4) FLT3 x TCRα/β; bsFc$^{ko}$-1/2 [N-terminal anti-FLT3 chimeric heavy chain (clone BV10) and C-terminal TCRα/β single-chain (clone BMA031; VH-VL orientation)], being a chain of a glycan-ko-variant-halfmolecule (SEQ ID NO: 9)

QVQLKQSGPGLVQPSQSLSITCTVSGFSLT<u>NYGLH</u>WVRQSPGKGLEWLG<u>VIWSGGSTDYNAA
FISRLSISKDNSKSQVFFKMNSLQADDTAIYYCAR<u>KGGIYYANHYYAMDY</u>WGQGTSVTVSSAST
KGPSVFPLAPSSKSTSGGTAALGCLVKDYFPEPVTVSWNSGALTSGVHTFPAVLQSSGLYSLSS
VVTVPSSSLGTQTYICNVNHKPSNTKVDKKV</u>EPKSCDKTHTSPPSPAPPVAGPSVFLFPPKPKDT
LMISRTPEVTCVVVGVSHEDPEVKFNWYVDGVEVHNAKTKPREEQYQSTYRVVSVLTVLHQDW
LNGKEYKCKVSNKQLPSPIEKTISKAK*GQPSG*EVQLQQSGPELVKPGASVKMSCKASGYKFT<u>S
YVMH</u>WVKQKPGQGLEWIG<u>YINPYNDVTKYNEKFKG</u>KATLTSDKSSSTAYMELSSLTSEDSAVH
YCAR<u>GSYYDYDGFVY</u>GQGTLVTVSS*GGGGSGGGGSGGGGS*QIVLTQSPAIMSASPGEKVTMT
C*SATSSVSYMH*WYQQKSGTSPKRWIY*DTSKLAS*GVPARFSGSGSGTSYSLTISSMEAEDAATY
YC*QQWSSNPLT*FGAGTKLELK\*

Fig. 6 CONT.

5) FLT3 x CD28; bsFc$^{ko}$-1/2 [N-terminal anti-FLT3 chimeric heavy chain (clone 4G8) and C-terminal CD28 single-chain (clone 9.3; VL-VH orientation)], being a chain of a glycan-ko-variant-halfmolecule (SEQ ID NO: 10)

QVQLQQPGAELVKPGASLKLSCKSSGYTFT<u>SYWMH</u>WVRQRPGHGLEWIG<u>EIDPSDSYKDYNQ</u>
<u>KFKD</u>KATLTVDRSSNTAYMHLSSLTSDDSAVYYCAR<u>AITTTPFDF</u>WGQGTTLTVSSASTKGPSV
FPLAPSSKSTSGGTAALGCLVKDYFPEPVTVSWNSGALTSGVHTFPAVLQSSGLYSLSSVVTVP
SSSLGTQTYICNVNHKPSNTKVDKKV<u>EPKSCDKTHTSPPSPAPPVAGPSVFLFPPKPKDTLMISR</u>
<u>TPEVTCVVVGVSHEDPEVKFNWYVDGVEVHNAKTKPREEQYQSTYRVVSVLTVLHQDWLNGKE</u>
<u>YKCKVSNKQLPSPIEKTISKAK</u>G*QPSGDIELTQSPASLAVSLGQRATISC*<u>*RASESVEYYVTSLMQ*</u>
*WYQQKPGQPPKLLIF*<u>*AASNVESG*</u>*VPARFSGSGSGTNFSLNIHPVDEDDVAMYFC*<u>*QQSRKVPYT*</u>
*FGGGTKLEIKR*<u>*GGGGSGGGGSGGGGS*</u>*QVKLQQSGPGLVTPSQSLSITCTVSGFSLS*<u>*DYGVH*</u>W
VRQSPGQGLEWLG<u>VIWAGGGTNYNSALMS</u>RKSISKDNSKSQVFLKMNSLQADDTAVYYCAR<u>D</u>
<u>KGYSYYYSMDY</u>WGQGTTVTVSS\*

6) FLT3 x CD28; bsFc$^{ko}$-1/2 [N-terminal anti-FLT3 chimeric heavy chain (clone BV10) and C-terminal CD28 single-chain (clone 9.3; VL-VH orientation)], being a chain of a glycan-ko-variant-halfmolecule (SEQ ID NO: 11)

QVQLKQSGPGLVQPSQSLSITCTVSGFSLT<u>NYGLH</u>WVRQSPGKGLEWLG<u>VIWSGGSTDYNAA</u>
<u>FISR</u>LSISKDNSKSQVFFKMNSLQADDTAIYYCAR<u>KGGIYYANHYYAMDY</u>WGQGTSVTVSSAST
KGPSVFPLAPSSKSTSGGTAALGCLVKDYFPEPVTVSWNSGALTSGVHTFPAVLQSSGLYSLSS
VVTVPSSSLGTQTYICNVNHKPSNTKVDKKV<u>EPKSCDKTHTSPPSPAPPVAGPSVFLFPPKPKDT</u>
<u>LMISRTPEVTCVVVGVSHEDPEVKFNWYVDGVEVHNAKTKPREEQYQSTYRVVSVLTVLHQDW</u>
<u>LNGKEYKCKVSNKQLPSPIEKTISKAK</u>G*QPSG*
*DIELTQSPASLAVSLGQRATISC*<u>*RASESVEYYVTSLMQ*</u>*WYQQKPGQPPKLLIF*<u>*AASNVESG*</u>*VPA*
*RFSGSGSGTNFSLNIHPVDEDDVAMYFC*<u>*QQSRKVPYT*</u>*FGGGTKLEIKR*<u>*GGGGSGGGGSGGGG*</u>
<u>*S*</u>*QVKLQQSGPGLVTPSQSLSITCTVSGFSLS*<u>*DYGVH*</u>WVRQSPGQGLEWLG<u>VIWAGGGTNYNS</u>
<u>ALMS</u>RKSISKDNSKSQVFLKMNSLQADDTAVYYCAR<u>DKGYSYYYSMDY</u>WGQGTTVTVSS\*

Fig. 6 CONT.

7) FLT3 x CD16; bsFc$^{ko}$-1/2 [N-terminal anti-FLT3 chimeric heavy chain (clone 4G8) and C-terminal CD16 single-chain (clone 3G8; VL-VH orientation)], being a chain of a glycan-ko-variant-halfmolecule (SEQ ID NO: 12)

QVQLQQPGAELVKPGASLKLSCKSSGYTFT<u>SYWMH</u>WVRQRPGHGLEWIG<u>EIDPSDSYKDYNQ</u>
<u>KFKD</u>KATLTVDRSSNTAYMHLSSLTSDDSAVYYCAR<u>AITTTPFDF</u>WGQGTTLTVSSASTKGPSV
FPLAPSSKSTSGGTAALGCLVKDYFPEPVTVSWNSGALTSGVHTFPAVLQSSGLYSLSSVVTVP
SSSLGTQTYICNVNHKPSNTKVDKKV<u>EPKSCDKTHTSPPSPAPPVAGPSVFLFPPKPKDTLMISR</u>
<u>TPEVTCVVVGVSHEDPEVKFNWYVDGVEVHNAKTKPREEQYQSTYRVVSVLTVLHQDWLNGKE</u>
<u>YKCKVSNKQLPSPIEKTISKAK</u>G*QPSGDIVLTQSPASLAVSLGQRATISC*<u>*KASQSVDFGDSFMN*</u>
*WYQQKPGQPPKLLIY*<u>*TTSNLES*</u>*GIPARFSASGSGTDFTLNIHPVEEEDTATYYC*<u>*QQSNEDPYTF*</u>
*GGGTKLEIK*<u>*GGGGSGGGGSGGGGS*</u>*QVTLKESGPGILQPSQTLSLTCSFSGFSLR*<u>*TSGMGVGW*</u>
*IRQPSGKGLEWLA*<u>*HIWWDDDKRYNPALKS*</u>*RLTISKDTSSNQVFLKIASVDTADTATYYCAQ*<u>*INP*</u>
<u>*AWFAY*</u>*WGQGTLVTVSS*\*

8) FLT3 x CD16; bsFc$^{ko}$-1/2 [N-terminal anti-FLT3 chimeric heavy chain (clone BV10) and C-terminal CD16 single-chain (clone 3G8; VL-VH orientation)], being a chain of a glycan-ko-variant-halfmolecule (SEQ ID NO. 13)

QVQLKQSGPGLVQPSQSLSITCTVSGFSLT<u>NYGLH</u>WVRQSPGKGLEWLG<u>VIWSGGSTDYNAA</u>
<u>FISR</u>LSISKDNSKSQVFFKMNSLQADDTAIYYCAR<u>KGGIYYANHYYAMDY</u>WGQGTSVTVSSAST
KGPSVFPLAPSSKSTSGGTAALGCLVKDYFPEPVTVSWNSGALTSGVHTFPAVLQSSGLYSLSS
VVTVPSSSLGTQTYICNVNHKPSNTKVDKKV<u>EPKSCDKTHTSPPSPAPPVAGPSVFLFPPKPKDT</u>
<u>LMISRTPEVTCVVVGVSHEDPEVKFNWYVDGVEVHNAKTKPREEQYQSTYRVVSVLTVLHQDW</u>
<u>LNGKEYKCKVSNKQLPSPIEKTISKAK</u>G*QPSGDIVLTQSPASLAVSLGQRATISC*<u>*KASQSVDFDG*</u>
<u>*DSFMN*</u>*WYQQKPGQPPKLLIY*<u>*TTSNLES*</u>*GIPARFSASGSGTDFTLNIHPVEEEDTATYYC*<u>*QQSNE*</u>
<u>*DPYTF*</u>*GGGTKLEIK*<u>*GGGGSGGGGSGGGGS*</u>*QVTLKESGPGILQPSQTLSLTCSFSGFSLR*<u>*TSG*</u>
<u>*MGVGW*</u>*IRQPSGKGLEWLA*<u>*HIWWDDDKRYNPALKS*</u>*RLTISKDTSSNQVFLKIASVDTADTATYY*
*CAQ*<u>*INPAWFAY*</u>*WGQGTLVTVSS*\*

Fig. 6 CONT.

9) CD19 x CD3, bsFc$^{ko}$-1/2 [N-terminal anti-CD19 chimeric heavy chain (clone 4G7) and C-terminal anti-CD3 single-chain (clone UCHT1; VL-VH orientation)]: being a chain of a glycan-ko-variant-halfmolecule (SEQ ID NO: 14)

**EVQLQQSGPELIKPGASVKMSCKASGYTFT<u>SYVMH</u>WVKQKPGQGLEWIG<u>YINPYNDGTKYNE
KFKGK</u>ATLTSDKSSSTAYMELSSLTSEDSAVYYCAR<u>GTYYYGSRVFDY</u>WGQGTTLTVSS**ASTK
GPSVFPLAPSSKSTSGGTAALGCLVKDYFPEPVTVSWNSGALTSGVHTFPAVLQSSGLYSLSSV
VTVPSSSLGTQTYICNVNHKPSNTKVDKKVE<u>PKSCDKTHTSPPSPAPPVAGPSVFLFPPKPKDTL
MISRTPEVTCVVVGVSHEDPEVKFNWYVDGVEVHNAKTKPREEQYQSTYRVVSVLTVLHQDWL
NGKEYKCKVSNKQLPSPIEKTISKAK</u>*GQPSGDIQMTQSPSSLSASVGDRVTITC<u>RASQDIRNYLN</u>
*WYQQKPGKAPKLLIY<u>YTSRLES</u>GVPSRFSGSGSGTDYTLTISSLQPEDFATYYC<u>QQGNTLPWT</u>*
*FGQGTKVEIKGGGGSGGGGSGGGGS*EVQLVESGGGLVQPGGSLRLSCAASGYSFT<u>GYTMNW</u>
VRQAPGKGLEWVA<u>LINPYKGVSTYNQKFKD</u>RFTISVDKSKNTAYLQMNSLRAEDTAVYYCAR<u>S
GYYGDSDWYFDV</u>WGQGTLVTVSS***

10) CD19 x TCRα/β, bsFc$^{ko}$-1/2 [N-terminal anti-CD19 chimeric heavy chain (clone 4G7) and C-terminal anti-TCRα/β single-chain (clone BMA031; VH-VL orientation)]: being a chain of a glycan-ko-variant-halfmolecule (SEQ ID NO: 15)

**EVQLQQSGPELIKPGASVKMSCKASGYTFT<u>SYVMH</u>WVKQKPGQGLEWIG<u>YINPYNDGTKYNE
KFKGK</u>ATLTSDKSSSTAYMELSSLTSEDSAVYYCAR<u>GTYYYGSRVFDY</u>WGQGTTLTVSS**ASTK
GPSVFPLAPSSKSTSGGTAALGCLVKDYFPEPVTVSWNSGALTSGVHTFPAVLQSSGLYSLSSV
VTVPSSSLGTQTYICNVNHKPSNTKVDKKVE<u>PKSCDKTHTSPPSPAPPVAGPSVFLFPPKPKDTL
MISRTPEVTCVVVGVSHEDPEVKFNWYVDGVEVHNAKTKPREEQYQSTYRVVSVLTVLHQDWL
NGKEYKCKVSNKQLPSPIEKTISKAK</u>*GQPSG***EVQLQQSGPELVKPGASVKMSCKASGYKFT<u>SY
VMH</u>WVKQKPGQGLEWIG<u>YINPYNDVTKYNEKFKGK</u>ATLTSDKSSSTAYMELSSLTSEDSAVHY
CAR<u>GSYYDYDGFVY</u>GQGTLVTVSS***GGGGSGGGGSGGGGSQIVLTQSPAIMSASPGEKVTMTC*
*SATSSVS<u>YMH</u>WYQQKSGTSPKRWIY<u>DTSKLAS</u>GVPARFSGSGSGTSYSLTISSMEAEDAATYY*
*C<u>QQWSSNPLT</u>FGAGTKLELK***

Fig. 6 CONT.

11) CD19 x CD28; bsFc$^{ko}$-1/2 [N-terminal anti-CD19 chimeric heavy chain (clone 4G7) and C-terminal CD28 single-chain (clone 9.3; VL-VH orientation)], being a chain of a glycan-ko-variant-halfmolecule (SEQ ID NO: 16)

EVQLQQSGPELIKPGASVKMSCKASGYTFT<u>SYVMH</u>WVKQKPGQGLEWIG<u>YINPYNDGTKYNE
KFKG</u>KATLTSDKSSSTAYMELSSLTSEDSAVYYCAR<u>GTYYYGSRVFDY</u>WGQGTTLTVSSASTK
GPSVFPLAPSSKSTSGGTAALGCLVKDYFPEPVTVSWNSGALTSGVHTFPAVLQSSGLYSLSSV
VTVPSSSLGTQTYICNVNHKPSNTKVDKKV<u>EPKSCDKTHTSPPSPAPPVAGPSVFLFPPKPKDTL
MISRTPEVTCVVVGVSHEDPEVKFNWYVDGVEVHNAKTKPREEQYQSTYRVVSVLTVLHQDWL
NGKEYKCKVSNKQLPSPIEKTISKAK</u>GQPSG
DIELTQSPASLAVSLGQRATISC<u>RASESVEYYVTSLMQ</u>WYQQKPGQPPKLLIF<u>AASNVES</u>GVPA
RFSGSGSGTNFSLNIHPVDEDDVAMYFC<u>QQSRKVPYT</u>FGGGTKLEIKRGGGGSGGGGSGGGG
<u>S</u>QVKLQQSGPGLVTPSQSLSITCTVSGFSLS<u>DYGVH</u>WVRQSPGQGLEWLG<u>VIWAGGGTNYNS
ALMS</u>RKSISKDNSKSQVFLKMNSLQADDTAVYYCAR<u>DKGYSYYYSMDY</u>WGQGTTVTVSS*

12) CD19 x CD16; bsFc$^{ko}$-1/2 [N-terminal anti-CD19 chimeric heavy chain (clone 4G7) and C-terminal CD16 single-chain (clone 3G8; VL-VH orientation)], being a chain of a glycan-ko-variant-halfmolecule (SEQ ID NO: 17)

EVQLQQSGPELIKPGASVKMSCKASGYTFT<u>SYVMH</u>WVKQKPGQGLEWIG<u>YINPYNDGTKYNE
KFKG</u>KATLTSDKSSSTAYMELSSLTSEDSAVYYCAR<u>GTYYYGSRVFDY</u>WGQGTTLTVSSASTK
GPSVFPLAPSSKSTSGGTAALGCLVKDYFPEPVTVSWNSGALTSGVHTFPAVLQSSGLYSLSSV
VTVPSSSLGTQTYICNVNHKPSNTKVDKKV<u>EPKSCDKTHTSPPSPAPPVAGPSVFLFPPKPKDTL
MISRTPEVTCVVVGVSHEDPEVKFNWYVDGVEVHNAKTKPREEQYQSTYRVVSVLTVLHQDWL
NGKEYKCKVSNKQLPSPIEKTISKAK</u>GQPSGDIVLTQSPASLAVSLGQRATISC<u>KASQSVDFDGD
SFMN</u>WYQQKPGQPPKLLIY<u>TTSNLES</u>GIPARFSASGSGTDFTLNIHPVEEEDTATYYC<u>QQSNED
PYT</u>FGGGTKLEIKGGGGSGGGGSGGGGSQVTLKESGPGILQPSQTLSLTCSFSGFSLR<u>TSGM
GVGW</u>IRQPSGKGLEWLA<u>HIWWDDDKRYNPALKS</u>RLTISKDTSSNQVFLKIASVDTADTATYYC
AQ<u>INPAWFAY</u>WGQGTLVTVSS*

Fig. 6 CONT.

13) CSPG4 x CD3, bsFc$^{ko}$-1/2 [N-terminal anti-CSPG4 chimeric heavy chain (clone 9.2.27) and C-terminal anti-CD3 single-chain (clone UCHT1; VL-VH orientation)], being a chain of a glycan-ko-variant-halfmolecule (SEQ ID NO: 18)

QVKLQQSGPELVKPGASVKISCKASGYAFS<u>RSWMN</u>WVKQRPGQGLEWIG<u>RIYPGDGDTNYN</u>
<u>GKFKG</u>KATLTADKSSSTAYMQVSSLTSVDSAVYFCAR<u>GNTVVVPYTMDY</u>WGQGTTVTVSSAS
TKGPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKV<u>EPKSCDKTHTSPPSPAPPVAGPSVFLFPPKPKD</u>
<u>TLMISRTPEVTCVVVGVSHEDPEVKFNWYVDGVEVHNAKTKPREEQYQSTYRVVSVLTVLHQD</u>
<u>WLNGKEYKCKVSNKQLPSPIEKTISKAK</u>*GQPSGDIQMTQSPSSLSASVGDRVTITC*<u>*RASQDIRNY*</u>
<u>*LNWYQQKPGKAPKLLIY*</u><u>*YTSRLES*</u>*GVPSRFSGSGSGTDYTLTISSLQPEDFATYYC*<u>*QQGNTLP*</u>
<u>*WT*</u>*FGQGTKVEIK*<u>*GGGGSGGGGSGGGGS*</u>*EVQLVESGGGLVQPGGSLRLSCAASGYSFT*<u>*GYTM*</u>
<u>*NWVRQAPGKGLEWVA*</u><u>*LINPYKGVSTYNQKFKD*</u>*RFTISVDKSKNTAYLQMNSLRAEDTAVYYC*
*AR*<u>*SGYYGDSDWYFDV*</u>*WGQGTLVTVSS**

14) CSPG4 x TCRα/β, bsFc$^{ko}$-1/2 [N-terminal anti-CSPG4 chimeric heavy chain (clone 9.2.27) and C-terminal anti-TCRα/β single-chain (clone BMA031; VH-VL orientation)]: being a chain of a glycan-ko-variant-halfmolecule (SEQ ID NO: 19)

QVKLQQSGPELVKPGASVKISCKASGYAFS<u>RSWMN</u>WVKQRPGQGLEWIG<u>RIYPGDGDTNYN</u>
<u>GKFKG</u>KATLTADKSSSTAYMQVSSLTSVDSAVYFCAR<u>GNTVVVPYTMDY</u>WGQGTTVTVSSAS
TKGPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKV<u>EPKSCDKTHTSPPSPAPPVAGPSVFLFPPKPKD</u>
<u>TLMISRTPEVTCVVVGVSHEDPEVKFNWYVDGVEVHNAKTKPREEQYQSTYRVVSVLTVLHQD</u>
<u>WLNGKEYKCKVSNKQLPSPIEKTISKAK</u>*GQPSG*EVQLQQSGPELVKPGASVKMSCKASGYKFT
S<u>YVMH</u>WVKQKPGQGLEWIG<u>YINPYNDVTKYNEKFKG</u>KATLTSDKSSSTAYMELSSLTSEDSAV
HYCAR<u>GSYYDYDGFVY</u>GQGTLVTVSS<u>*GGGGSGGGGSGGGGS*</u>*QIVLTQSPAIMSASPGEKVTM*
*TC*<u>*SATSSVSYMH*</u>*WYQQKSGTSPKRWIY*<u>*DTSKLAS*</u>*GVPARFSGSGSGTSYSLTISSMEAEDAAT*
*YYC*<u>*QQWSSNPLT*</u>*FGAGTKLELK**

Fig. 6 CONT.

15) CSPG4 x CD28; bsFc$^{ko}$-1/2 [N-terminal anti-CSPG4 chimeric heavy chain (clone 9.2.27) and C-terminal CD28 single-chain (clone 9.3; VL-VH orientation)], being a chain of a glycan-ko-variant-halfmolecule (SEQ ID NO: 20)

**QVKLQQSGPELVKPGASVKISCKASGYAFSRSWMNWVKQRPGQGLEWIGRIYPGDGDTNYN
GKFKGKATLTADKSSSTAYMQVSSLTSVDSAVYFCARGNTVVVPYTMDYWGQGTTVTVSS**AS
TKGPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHTSPPSPAPPVAGPSVFLFPPKPKD
TLMISRTPEVTCVVVGVSHEDPEVKFNWYVDGVEVHNAKTKPREEQYQSTYRVVSVLTVLHQD
WLNGKEYKCKVSNKQLPSPIEKTISKAKG*QPSG*
*DIELTQSPASLAVSLGQRATISC*RASESVEYYVTSLMQW*YQQKPGQPPKLLIF*AASNVES*GVPA
RFSGSGSGTNFSLNIHPVDEDDVAMYFC*QQSRKVPYT*FGGGTKLEIKR*GGGGSGGGGSGGGG
S*QVKLQQSGPGLVTPSQSLSITCTVSGFSLS*DYGVH*WVRQSPGQGLEWLG*VIWAGGGTNYNS
ALMS*RKSISKDNSKSQVFLKMNSLQADDTAVYYCAR*DKGYSYYYSMDY*WGQGTTVTVSS***

16) CSPG4 x CD16; bsFc$^{ko}$-1/2 [N-terminal anti-CSPG4 chimeric heavy chain (clone 9.2.27) and C-terminal CD16 single-chain (clone 3G8; VL-VH orientation)], being a chain of a glycan-ko-variant-halfmolecule (SEQ ID NO: 21)

**QVKLQQSGPELVKPGASVKISCKASGYAFSRSWMNWVKQRPGQGLEWIGRIYPGDGDTNYN
GKFKGKATLTADKSSSTAYMQVSSLTSVDSAVYFCARGNTVVVPYTMDYWGQGTTVTVSS**AS
TKGPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHTSPPSPAPPVAGPSVFLFPPKPKD
TLMISRTPEVTCVVVGVSHEDPEVKFNWYVDGVEVHNAKTKPREEQYQSTYRVVSVLTVLHQD
WLNGKEYKCKVSNKQLPSPIEKTISKAKG*QPSGDIVLTQSPASLAVSLGQRATISC*KASQSVDFD
GDSFMN*WYQQKPGQPPKLLIY*TTSNLES*GIPARFSASGSGTDFTLNIHPVEEEDTATYYC*QQSN
EDPYT*FGGGTKLEIK*GGGGSGGGGSGGGGS*QVTLKESGPGILQPSQTLSLTCSFSGFSLR*TSG
MGVG*WIRQPSGKGLEWLA*HIWWDDDKRYNPALKS*RLTISKDTSSNQVFLKIASVDTADTATYY
CAQ*INPAWFAY*WGQGTLVTVSS***

Fig. 6 CONT.

17) EGFR x CD3; bsFc$^{ko}$-1/2 [N-terminal anti-EGFR chimeric heavy chain (clone C225) and C-terminal CD3 single-chain (clone UCHT1; VL-VH orientation)], being a chain of a glycan-ko-variant-halfmolecule (SEQ ID NO: 22)

QVQLKQSGPGLVQPSQSLSITCTVSGFSLT<u>NYGVH</u>WVRQSPGKGLEWLG<u>VIWSGGNTDYNTP</u>
<u>FTSR</u>LSINKDNSKSQVFFKMNSLQSNDTAIYYCAR<u>ALTYYDYEFAY</u>WGQGTLVTVSSASTKGPS
VFPLAPSSKSTSGGTAALGCLVKDYFPEPVTVSWNSGALTSGVHTFPAVLQSSGLYSLSSVVTV
PSSSLGTQTYICNVNHKPSNTKVDKKV<u>EPKSCDKTHTSPPSPAPPVAGPSVFLFPPKPKDTLMIS</u>
<u>RTPEVTCVVVGVSHEDPEVKFNWYVDGVEVHNAKTKPREEQYQSTYRVVSVLTVLHQDWLNGK</u>
<u>EYKCKVSNKQLPSPIEKTISKAK</u>*GQPSGDIQMTQSPSSLSASVGDRVTITC*<u>*RASQDIRNYLNWYQ*</u>
*QKPGKAPKLLIY*<u>*YTSRLES*</u>*GVPSRFSGSGSGTDYTLTISSLQPEDFATYYC*<u>*QQGNTLPWT*</u>*FGQ*
*GTKVEIK*<u>*GGGGSGGGGSGGGGS*</u>*EVQLVESGGGLVQPGGSLRLSCAASGYSFT*<u>*GYTMN*</u>*WVRQ*
*APGKGLEWVA*<u>*LINPYKGVSTYNQKFKD*</u>*RFTISVDKSKNTAYLQMNSLRAEDTAVYYCAR*<u>*SGYY*</u>
<u>*GDSDWYFDV*</u>*WGQGTLVTVSS**

18) EGFR x TCRα/β; bsFc$^{ko}$-1/2 [N-terminal anti-EGFR chimeric heavy chain (clone C225) and C-terminal TCRα/β single-chain (clone BMA031; VH-VL orientation)], being a chain of a glycan-ko-variant-halfmolecule (SEQ ID NO: 23)

QVQLKQSGPGLVQPSQSLSITCTVSGFSLT<u>NYGVH</u>WVRQSPGKGLEWLG<u>VIWSGGNTDYNTP</u>
<u>FTSR</u>LSINKDNSKSQVFFKMNSLQSNDTAIYYCAR<u>ALTYYDYEFAY</u>WGQGTLVTVSSASTKGPS
VFPLAPSSKSTSGGTAALGCLVKDYFPEPVTVSWNSGALTSGVHTFPAVLQSSGLYSLSSVVTV
PSSSLGTQTYICNVNHKPSNTKVDKKV<u>EPKSCDKTHTSPPSPAPPVAGPSVFLFPPKPKDTLMIS</u>
<u>RTPEVTCVVVGVSHEDPEVKFNWYVDGVEVHNAKTKPREEQYQSTYRVVSVLTVLHQDWLNGK</u>
<u>EYKCKVSNKQLPSPIEKTISKAK</u>*GQPSG*EVQLQQSGPELVKPGASVKMSCKASGYKFT<u>SYVMH</u>
WVKQKPGQGLEWIG<u>YINPYNDVTKYNEKFKG</u>KATLTSDKSSSTAYMELSSLTSEDSAVHYCAR
<u>GSYYDYDGFVY</u>GQGTLVTVSS*<u>GGGGSGGGGSGGGGS</u>QIVLTQSPAIMSASPGEKVTMTC<u>SAT</u>*
*<u>SSVSYMH</u>WYQQKSGTSPKRWIY<u>DTSKLAS</u>GVPARFSGSGSGTSYSLTISSMEAEDAATYYC<u>Q</u>*
*<u>QWSSNPLTFGAGTKLELK</u>**

Fig. 6 CONT.

19) EGFR x CD28; bsFc$^{ko}$-1/2 [N-terminal anti-EGFR chimeric heavy chain (clone C225) and C-terminal CD28 single-chain (clone 9.3; VL-VH orientation)], being a chain of a glycan-ko-variant-halfmolecule (SEQ ID NO: 24)

QVQLKQSGPGLVQPSQSLSITCTVSGFSLTNYGVHWVRQSPGKGLEWLGVIWSGGNTDYNTP
FTSRLSINKDNSKSQVFFKMNSLQSNDTAIYYCARALTYYDYEFAYWGQGTLVTVSSASTKGPS
VFPLAPSSKSTSGGTAALGCLVKDYFPEPVTVSWNSGALTSGVHTFPAVLQSSGLYSLSSVVTV
PSSSLGTQTYICNVNHKPSNTKVDKKVEPKSCDKTHTSPPSPAPPVAGPSVFLFPPKPKDTLMIS
RTPEVTCVVVGVSHEDPEVKFNWYVDGVEVHNAKTKPREEQYQSTYRVVSVLTVLHQDWLNGK
EYKCKVSNKQLPSPIEKTISKAK*GQPSG*
*DIELTQSPASLAVSLGQRATISCRASESVEYYVTSLMQWYQQKPGQPPKLLIFAASNVESGVPA*
*RFSGSGSGTNFSLNIHPVDEDDVAMYFCQQSRKVPYTFGGGTKLEIKR**GGGGSGGGGSGGGG*
*S*QVKLQQSGPGLVTPSQSLSITCTVSGFSLSDYGVHWVRQSPGQGLEWLGVIWAGGGTNYNS
ALMSRKSISKDNSKSQVFLKMNSLQADDTAVYYCARDKGYSYYYSMDYWGQGTTVTVSS*

20) EGFR x CD16; bsFc$^{ko}$-1/2 [N-terminal anti-EGFR chimeric heavy chain (clone C225) and C-terminal CD16 single-chain (clone 3G8; VL-VH orientation)], being a chain of a glycan-ko-variant-halfmolecule (SEQ ID NO: 25)

QVQLKQSGPGLVQPSQSLSITCTVSGFSLTNYGVHWVRQSPGKGLEWLGVIWSGGNTDYNTP
FTSRLSINKDNSKSQVFFKMNSLQSNDTAIYYCARALTYYDYEFAYWGQGTLVTVSSASTKGPS
VFPLAPSSKSTSGGTAALGCLVKDYFPEPVTVSWNSGALTSGVHTFPAVLQSSGLYSLSSVVTV
PSSSLGTQTYICNVNHKPSNTKVDKKVEPKSCDKTHTSPPSPAPPVAGPSVFLFPPKPKDTLMIS
RTPEVTCVVVGVSHEDPEVKFNWYVDGVEVHNAKTKPREEQYQSTYRVVSVLTVLHQDWLNGK
EYKCKVSNKQLPSPIEKTISKAK*GQPSGDIVLTQSPASLAVSLGQRATISCKASQSVDFDGDSFM
*N*WYQQKPGQPPKLLIYTTSNLESGIPARFSASGSGTDFTLNIHPVEEEDTATYYCQQSNEDPYT
*FGGGTKLEIKGGGGSGGGGSGGGGSQVTLKESGPGILQPSQTLSLTCSFSGFSLRTSGMGVG*
WIRQPSGKGLEWLAHIWWDDDKRYNPALKSRLTISKDTSSNQVFLKIASVDTADTATYYCAQIN
PAWFAYWGQGTLVTVSS*

Fig. 6 CONT.

21) FLT3 x CD3; bsFc$^{ko}$-1 [N-terminal anti-FLT3 chimeric heavy chain (clone 4G8) und C-terminal CD3 single-chain (clone UCHT1; VL-VH orientation)]: being a chain of a ko-variant-(full) molecule that includes a CH3 domain, not a glycomutant (SEQ ID NO: 26)

QVQLQQPGAELVKPGASLKLSCKSSGYTFTSYWMHWVRQRPGHGLEWIGEIDPSDSYKDYNQ
KFKDKATLTVDRSSNTAYMHLSSLTSDDSAVYYCARAITTTPFDFWGQGTTLTVSSASTKGPSV
FPLAPSSKSTSGGTAALGCLVKDYFPEPVTVSWNSGALTSGVHTFPAVLQSSGLYSLSSVVTVP
SSSLGTQTYICNVNHKPSNTKVDKKV**EPKSCDKTHTCPPCPAPPVAGPSVFLFPPKPKDTLMISR
TPEVTCVVVGVSHEDPEVKFNWYVDGVEVHNAKTKPREEQYNSTYRVVSVLTVLHQDWLNGKE
YKCKVSNKQLPSPIEKTISKAKGQPREPQVYTLPPSRDELTKNQVSLTCLVKGFYPSDIAVEWES
NGQPENNYKTTPPVLDSDGSFFLYSKLTVDKSRWQQGNVFSCSVMHEALHNHYTQKSLSLSPG
KSG*DIQMTQSPSSLSASVGDRVTITCRASQDIRNYLNWYQQKPGKAPKLLIYYTSRLES**GVPSR
FSGSGSGTDYTLTISSLQPEDFATYYCQQGNTLPWTFGQGTKVEIK**GGGGSGGGGSGGGGS*E
*VQLVESGGGLVQPGGSLRLSCAASGYSFT*GYTMNWVRQAPGKGLEWVALINPYKGVSTYNQ
KFKDRFTISVDKSKNTAYLQMNSLRAEDTAVYYCARSGYYGDSDWYFDVWGQGTLVTVSS*****

BISPECIFIC ANTIBODY MOLECULE

CROSS-REFERENCE TO RELATED APPLICATIONS

The present invention is filed under 35 U.S.C. §371 as the U.S. national phase of International Application No. PCT/EP2012/072364, filed 12 Nov. 2012, which designated the U.S. and claims the right of priority of U.S. provisional application 61/577,327 filed with the US Patent and Trademark Office on 19 Dec. 2011, the entire content of which is incorporated herein for all purposes.

SEQUENCE LISTING

The instant application contains a Sequence Listing which has been submitted in ASCII format via EFS-Web and is hereby incorporated by reference in its entirety. Said ASCII copy, created on Jun. 18, 2014, is named SCH1800US2 SeqListing.txt and is 125 kilobytes in size.

FIELD OF THE INVENTION

The present invention relates to a bispecific antibody molecule, as well as a method for producing the same, its use and a nucleic acid molecule encoding the bispecific antibody molecule. The invention in particular provides an antibody molecule that is capable of mediating target cell restricted activation of immune cells.

BACKGROUND

Monoclonal antibodies against the antigen-specific T cell receptor (TCR)/CD3-complex are able to efficiently activate T cells. This activation, however, requires the antibody to be—via its Fc portion—multimerized on the surface of Fc receptor expressing cells, which often also provide accessory signals for T cell activation (Davis, L., Vida, R. and Lipsky, P. E., Regulation of human T lymphocyte mitogenesis by antibodies to CD3, J. Immunol. [1986] 137: 3758-3767).

Bispecific antibodies, which recognize both an antigen on target cells (e.g. FLT3 or CD19 on leukemia cells, the CSPG4-antigen on melanoma cells or EGFR on glioblastoma cells) and the antigen specific T cell receptor (TCR)/CD3-complex, are likewise able to activate T cells (Jung, G., Ledbetter, J. A., and Muller-Eberhard, H. J., Induction of cytotoxicity in resting human T lymphocytes bound to tumor cells by antibody heteroconjugates, Proc. Natl. Acad. Sci. U.S.A [1987] 84: 4611-4615; Jung, G., & Eberhard, H. J., An in-vitro model for tumor immunotherapy with antibody heteroconjugates, Immunol. Today [1988] 9: 257-260; Jung, G., Brandl, M., Eisner, W., Fraunberger, P., Reifenberger, G., Schlegel, U., Wiestler, O. D., Reulen, H. J., Wilmanns, W. Local immunotherapy of glioma patients with a combination of 2 bispecific antibody fragments and resting autologous lymphocytes: evidence for in situ T-cell activation and therapeutic efficacy, Int J Cancer. [2001] 91: 225-30), and in addition to focus the activated cells on the target cell (Staerz, U. D., Kanagawa, O., and Bevan, M. J., Hybrid antibodies can target sites for attack by T cells, Nature [1985] 314: 628-631; Perez, P., Hoffman, R. W., Shaw, S., Bluestone, J. A., and Segal, D. M. Specific targeting of cytotoxic T cells by anti-T3 linked to anti-target cell antibody, Nature [1985] 316: 354-356; Jung, G., Honsik, C. J., Reisfeld, R. A. and Muller-Eberhard, H. J. Activation of human peripheral blood mononuclear cells by anti-T3: killing of tumor target cells coated with anti-target-anti-T3 conjugates, Proc. Natl. Acad. Sci. U.S.A, 83: 4479-4483, 1986). As a result T cell mediated lysis of tumour cells occurs. Agonistic antibodies to T-cell costimulatory molecule such as CD28, enhance anti-CD3 mediated T-cell activation. Such costimulatory antibodies are particularly effective if they are also provided in a bispecific format (Grosse-Hovest, L., Hartlapp, I., Marwan, W., Brem, G., Rammensee, H. G., and Jung, G., A recombinant bispecific single-chain antibody induces targeted, supra-agonistic CD28-stimulation and tumor cell killing, Eur. J. Immunol. [2003] 33: 1334-1340). In any case, we regard it as an absolute requirement for therapeutic applications of bispecific antibodies having CD3 specificity that binding to Fc receptors can be excluded (Jung, G., and Eberhard, H. J., An in-vitro model for tumor immunotherapy with antibody heteroconjugates, Immunol. Today [1988] 9: 257-260; Jung, G., Freimann, U., Von Marshall, Z., Reisfeld, R. A., and Wilmanns, W., Target cell-induced T cell activation with bi- and trispecific antibody fragments, Eur. J. Immunol. [1991] 21: 2431-2435). Such binding to Fc receptors would result in T cell activation in vivo, which occurs, regardless of the binding to a target antigen, at any location where Fc receptor expressing cells can be found, for instance within the entire hematopoietic, lymphatic and reticuloendothelial system. According to experience such T cell activation results in systemic activation of T cells, accompanied by a cytokine release syndrome, a dreaded adverse reaction during therapeutic use of T cell activating cytokines or antibodies (Rosenberg, S. A., Lotze, M. T., Yang, J. C., Aebersold, P. M., Linehan, W. M., Seipp, C. A., and White, D. E., Experience with the use of high-dose interleukin-2 in the treatment of 652 cancer patients, Ann. Surg. [1989] 210: 474-484; Tibben, J. G., Boerman, O. C., Massuger, L. F., Schijf, C. P., Claessens, R. A., and Corstens, F. H., Pharmacokinetics, biodistribution and biological effects of intravenously administered bispecific monoclonal antibody OC/TR F(ab')2 in ovarian carcinoma patients, Int. J. Cancer [1996] 66: 477-483; Kroesen, B. J., Buter, J., Sleijfer, D. T., Janssen, R. A., van der Graaf, W. T., The, T. H., de, L. L. and Mulder, N. H., Phase I study of intravenously applied bispecific antibody in renal cell cancer patients receiving subcutaneous interleukin 2, Br. J. Cancer [1994] 70: 652-661). Hence, the aim in formatting bispecific CD3 antibodies needs to be avoiding an Fc mediated systemic activation of T cells, and thereby allowing target cell restricted activation, which is exclusively dependent on binding of the target portion of the bispecific antibody to the corresponding target antigen (Jung, G., & Eberhard, H. J., An in-vitro model for tumor immunotherapy with antibody heteroconjugates, Immunol. Today [1988] 9: 257-260; Jung, G., Freimann, U., Von Marshall, Z., Reisfeld, R. A., and Wilmanns, W. Target cell-induced T cell activation with bi- and trispecific antibody fragments, Eur. J. Immunol. [1991] 21: 2431-2435). From the above said it emerges that when selecting the target antigen, expression as restricted to malign cells as possible has to be taken care of. In this way activation by non-malign cells and an accompanying release of cytokines can be kept as low as possible.

Similar considerations apply if bispecific antibodies are constructed that contain agonistic effector antibodies binding to triggering receptors on immune cells other than T cells, such as CD16 expressed on NK cells. In any case, Fc-mediated binding of the antibodies to Fc receptors should be avoided according to the reasoning outlined above for T cells.

The bispecific antibody which has proceeded furthest in clinical development today is Blinatumomab (Micromet, Inc., Rockville, Md.), a bispecific single chain antibody with CD19×CD3 specificity and a remarkable therapeutic activity against lymphoma and leukemia cells (Bargou, R., et al., Tumor regression in cancer patients by very low doses of a T cell-engaging antibody, Science [2008] 321: 974-977; Topp, M. S., et al., Targeted therapy with the T-cell-engaging antibody blinatumomab of chemotherapy-refractory minimal residual disease in B-lineage acute lymphoblastic leukemia patients results in high response rate and prolonged leukemia-free survival, J. Clin. Oncol. [2011] 29: 2493-2498).

Since the single chain format does not contain any domain of the Fc part, this antibody is target cell restricted within the above explained meaning, i.e. it only activates T cells in the presence of CD19 expressing target cells (Brischwein, K., et al., Strictly target cell-dependent activation of T cells by bispecific single-chain antibody constructs of the BiTE class, J. Immunother. [2007] 30: 798-807).

CD19 is, however, also expressed on normal B cells so that, despite target cell restriction, following therapeutic application, a systemic release of cytokines occurs, causing significant cytotoxicity already at daily doses around 100 μg (Bargou, R., et al., Tumor regression in cancer patients by very low doses of a T cell-engaging antibody, Science [2008] 321: 974-977; Topp, M. S., et al., Targeted therapy with the T-cell-engaging antibody blinatumomab of chemotherapy-refractory minimal residual disease in B-lineage acute lymphoblastic leukemia patients results in high response rate and prolonged leukemia-free survival, J. Clin. Oncol. [2011] 29: 2493-2498).

In addition the single chain format has the following disadvantages: (i) the molecular weight of about 50 kDa is relatively low and is associated with a short serum half life, (ii) antibodies of this format easily aggregate and (iii) are difficult to produce in conventional fermenting processes (Grosse-Hovest, L., Hartlapp, I., Marwan, W., Brem, G., Rammensee, H. G., and Jung, G., A recombinant bispecific single-chain antibody induces targeted, supra-agonistic CD28-stimulation and tumor cell killing, Eur. J. Immunol. [2003] 33: 1334-1340; Grosse-Hovest, L., et al., Cloned transgenic farm animals produce a bispecific antibody for T cell-mediated tumor cell killing, Proc. Natl. Acad. Sci. U.S.A [2004] 101: 6858-6863).

It is therefore an object of the present invention to provide a bispecific antibody molecule that overcomes at least some of the above difficulties and that can be generally used in therapy, amongst others for strictly target cell restricted activation of immune cells as described above.

SUMMARY OF THE INVENTION

In a first aspect the present invention provides a recombinant bispecific antibody molecule. The recombinant bispecific antibody molecule consists of a Fab fragment, a single chain Fv fragment and an immunoglobulin CH2 domain. The Fab fragment includes a first binding site for a first antigen. The single chain Fv fragment includes a second binding site for a second antigen. The Fab fragment and the single chain Fv fragment are coupled to each other via the CH2 domain. In typical embodiments the cystein residues forming inter-heavy chain disulfide bonds (C226 and C229 in human IgG-immunoglobulins) are exchanged.

In a second aspect the invention provides a tetrameric antibody molecule. The tetrameric antibody molecule includes a dimer of the antibody molecule according to the first aspect. The dimer is generally defined by a bond between cysteine residues of two antibody molecules of the first aspect, namely between cysteins in the hinge region. Such cysteine residues are typically preserved amino acids (C226 and C229 in human IgG-immunoglobulins).

In a third aspect the invention provides a recombinant bispecific antibody molecule. The recombinant bispecific antibody molecule includes a Fab fragment that includes a first binding site for a first antigen, a single chain Fv fragment that includes a second binding site for a second antigen, an immunoglobuline CH2 domain, and an immunoglobuline CH3 domain. The Fab fragment and the single chain Fv fragment are linked via the CH2 domain/CH3 domain. At least one amino acid residue of the CH2 domain that is able to mediate binding to Fc-receptors is lacking or mutated. In typical embodiments of this aspect at least one of the cystein residues forming inter-chain disulfide bonds (C226 and C229 in human IgG-antibodies) are exchanged. In some embodiments such molecules may contain additional modifications in the CH3 region that prevent dimerization with homotypic CH3 domains.

In a fourth aspect the invention provides a tetrameric antibody molecule. The tetrameric antibody molecule consists of a dimer of the recombinant bispecific antibody molecule according to the third aspect. The dimer is generally defined by a bond between preserved cysteines in the hinge region (C226 and C229 in human IgG-antibodies).

In a fifth aspect the invention provides a further recombinant bispecifc antibody molecule. This antibody molecule includes a Fab fragment including a first binding site for a first antigen, a single chain Fv fragment including a second binding site for a second antigen, an immunoglobulin CH2 domain, and an immunoglobulin CH3 domain. The Fab fragment and the single chain Fv fragment are linked to each other via the CH2 domain and the CH3 domain. At least one cysteine residue of this antibody molecule that is able to form a disulfide bridge for dimerisation is lacking or mutated.

In a sixth aspect the invention provides a nucleic acid molecule. The nucleic acid molecule encodes an antibody molecule according to any one of the first, the second, the third, the fourth or the fifth aspect.

In a seventh aspect the invention provides a pharmaceutical composition. The pharmaceutical composition includes an antibody molecule according to one of the first, the second, the third, the fourth and the fifth aspect.

In an eighth aspect the invention provides a method of treating a disease. The method includes using an antibody molecule according to one of the first, the second, the third, the fourth and the fifth aspects. Generally the antibody molecule is administered to a patient in need thereof.

In an ninth aspect the invention provides a host cell that includes a nucleic acid molecule according to the sixth aspect.

In a tenth aspect the invention provides a method of producing an antibody molecule according to one of the first, the second, the third, the fourth and fifth aspects. The method includes expressing a nucleic acid encoding the antibody molecule under conditions that allow expression of the nucleic acid molecule.

These aspects of the invention will be more fully understood in view of the following description, drawings and non-limiting examples.

BRIEF DESCRIPTION OF THE DRAWINGS

FIG. 1A depicts a bivalent molecule with a Fab fragment, a CH2 domain and a single chain Fv fragment. The antibody molecule has a main chain in which the CH2 domain is coupled via its N-terminus to the heavy chain CH1 and VH domains of a Fab fragment and via its C-terminus to a single chain Fv fragment (bsFc-1/2-format).

FIG. 1B depicts a bivalent antibody molecule with a main chain in which the CH2 domain is linked to the light chain of a Fab fragment, i.e. in which the main chain includes a VL and a CL domain, a hinge region, a CH2 domain and a single chain Fv fragment.

FIG. 1C shows a bivalent antibody molecule in which the main chain includes a VL and a CH1 domain, a hinge region, a CH2 domain and a single chain Fv fragment. A second chain of lower weight includes a VH and a CL domain. In the antibody molecule of FIG. 1C the Fab fragment is thus not a "classical (naturally occurring)" Fab fragment in which the variable domain of the light and the heavy chain are fused to its respective constant domain (CL or CH1, respectively) but a "hybrid" Fab fragment in which the variable domain is fused to the constant domain of the "opposite chain, i.e. the VH domain is fused to the CL domain and the VL domain is fused to the CH1 domain.

FIG. 1D depicts a bivalent antibody molecule with a main chain in which the CH2 domain is linked to a CL and a VH domain. A second chain of lower weight includes a VL and a CH1 domain. The antibody molecule of FIG. 1D thus includes a "hybrid Fab fragment" (that includes the first binding site) as it is also present in the molecule of FIG. 1C.

FIG. 1E depicts a bivalent antibody molecule with a build-up as in FIG. 1A, in which amino acids in the CH2 domain and/or the hinge region have been modified (indicated by "X" as depicted in FIG. 1O, bsFc$^{ko}$-1/2-format). Likewise, such modifications can be inserted into the molecules depicted in 1B-1D. In the molecules depicted in FIGS. 1A-1E the cystein residues forming inter-chain disulfide bonds (C226 and C229 in human IgG-antibodies) are exchanged to prevent formation of dimers (●).

FIG. 1F depicts as an illustrative embodiment a tetravalent molecule being a dimer of the unit depicted in FIG. 1A. Such a molecule may also be constructed in the Fab-configurations depicted in FIGS. 1B-1D with and without the Fc modifications depicted in FIG. 1E. These modifications are listed in FIG. 1P.

FIG. 1G depicts as an illustrative embodiment a tetravalent molecule, being a dimer of a unit that includes a Fab fragment, a CH2 domain, a CH3 domain and a single chain Fv fragment. Amino acids in the CH2 domain and in the hinge region have been modified (X); summarized in FIG. 1P. The two main chains of the antibody include a VH and a CH1 domain, a hinge region, a CH2 domain, a CH3 domain and a single chain Fv fragment (bsFc$^{ko}$-1-format). Similar molecules may also be constructed in the Fab-configurations depicted in FIGS. 1A-1E. In all these molecules dimers are defined by means of preserved cysteins in the hinge region (C226 and C229 in human IgG-antibodies).

FIG. 1H depicts a tetravalent molecule, being a dimer of a unit that includes with a Fab fragment, a CH2 domain, a CH3 domain and a single chain Fv fragment. Within the Fab fragment the two main chains of the antibody include a VH and a CL domain.

FIG. 1I shows a tetravalent antibody with a general build-up as depicted in FIG. 1G. In contrast to the embodiment of FIG. 1G only one of the two main chains of this antibody includes amino acids in the CH2 domain and the hinge region that have been modified (indicated by "X").

FIG. 1J depicts a tetravalent molecule in which the two main chains include a VL and a CL domain, a hinge region, a CH2 domain, a CH3 domain and a single chain Fv fragment.

FIG. 1K depicts a tetravalent molecule with two structurally different Fab fragments. The first main chain of the antibody includes a VL and a CL domain, a hinge region, a CH2 domain, a CH3 domain and a single chain Fv fragment. The second main chain of the antibody includes a VH and a CH1 domain, a hinge region, a CH2 domain, a CH3 domain and a single chain Fv fragment.

FIG. 1L depicts a tetravalent molecule, being a dimer of a unit that includes a Fab fragment, a CH2 domain, a CH3 domain and a single chain Fv fragment. Within the Fab fragment the two main chains of the antibody include a VL and a CH1 domain.

FIG. 1M depicts a further tetravalent molecule with two structurally different Fab fragments. The first main chain of the antibody includes a VL and a CH1 domain, a hinge region, a CH2 domain, a CH3 domain and a single chain Fv fragment. The second main chain of the antibody includes a VH and a CL domain, a hinge region, a CH2 domain, a CH3 domain and a single chain Fv fragment.

FIG. 1N depicts as an illustrative embodiment a bivalent molecule with a Fab fragment, a CH2 and CH3 domain and a single chain Fv fragment. The antibody molecule has a main chain in which the CH2 domain is coupled via its N-terminus to the heavy chain CH1 and VH domains of a Fab fragment and via its C-terminus to a CH3 domain which is coupled via its C-terminus to a single chain Fv-fragment. Such a molecule may also be constructed in the Fab-configurations depicted in FIGS. 1A-1D and may contain Fc modifications in the hinge and CH2 region ("X") as depicted in FIGS. 1E and 1O. In addition they may contain modifications in the CH3 domain that prevent dimerization of this domain and may influence binding to the neonatal Fc receptor (FcRn). Examples of residues that are involved in the dimerization and thus may be modified by deletion or mutation include T366, L368, F405, Y407, and K409 (cf. Dall'Aqua et al. "Contribution of domain interface residues to the stability of antibody CH3 domain homodimers" Biochemistry (1998) Volume: 37, Issue: 26, Pages: 9266-9273. Other contact residues in the CH3 domain interface, that can be modified, include Q347, Y349, T350, L351, L368, K370, K392, T394, P395, V397, L398, D399, F405, Y407, and K409. See S. Miller Protein-Protein Recognition and the Association of Immunoglobulin Constant Domains. J. Mol. Biol. (1990) Volume 216 pp 965-973, and J. Deisenhofer Crystallographic refinement and atomic models of a human Fc fragment and its complex with fragment B of protein A from *Staphylococcus aureus* at 2.9- and 2.8-A resolution. Biochemistry (1981) Volume 20 pp 2361-2370, and, as far as the binding of the neonatal Fc receptor is concerned, for example, the following amino acids residues of the CH2 domain: T250, M252, S254, T256, T307 H310 and of the CH3 domain: E380 M428, H433, N434, H435 (see the review of Roopenian & Akilesh; FcRn: the neonatal Fc receptor comes of age. Nature Reviews Immunology (2007) Volume 7 pp: 715-725. In all these molecules of the invention the cystein residues forming inter-chain disulfide bonds (C226 and C229 in human IgG-antibodies) are exchanged to prevent formation of dimers (●).

Figure 1:
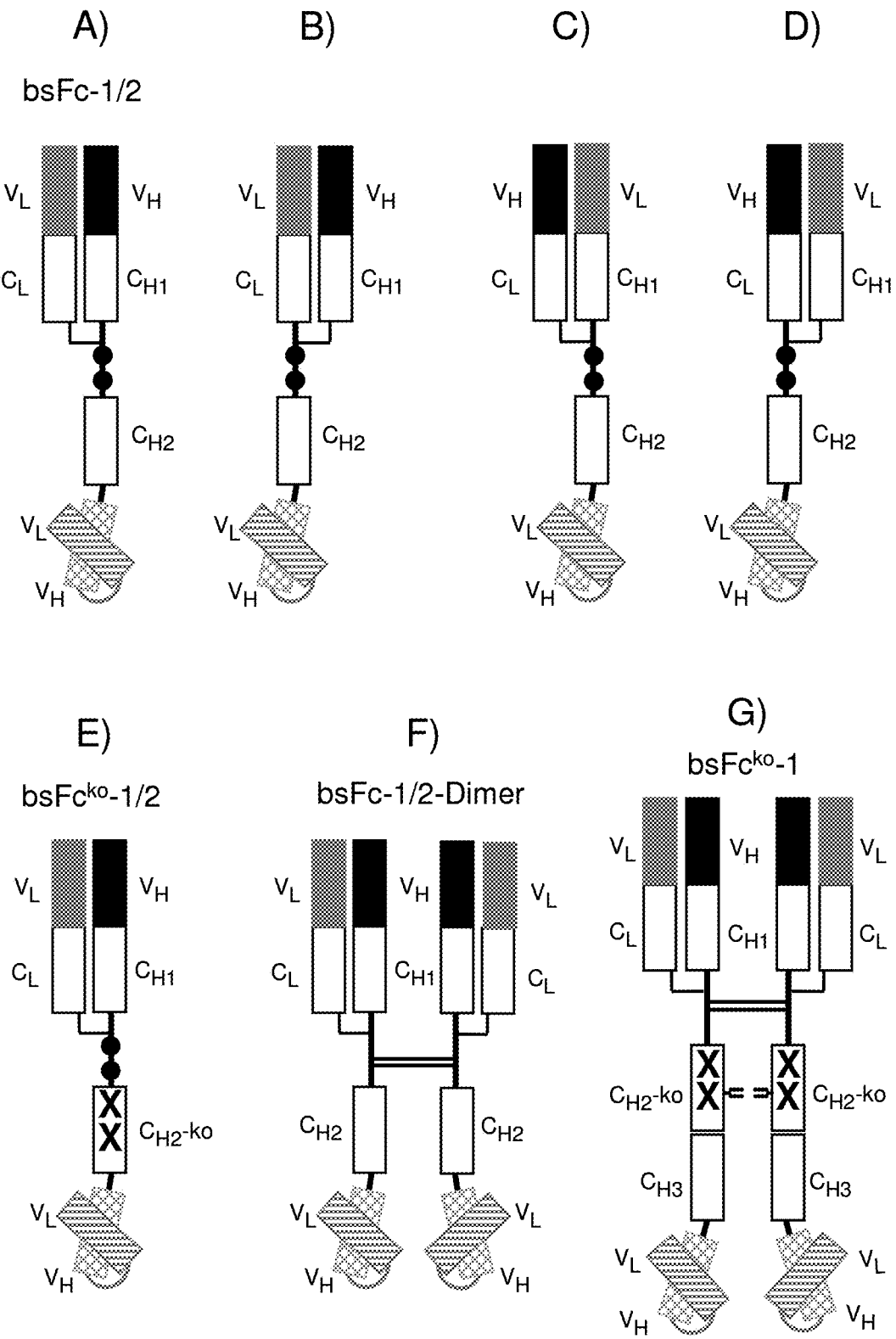
FIG. 1 schematically depicts embodiments of bispecific antibody molecules according to the invention.
Figure 1:
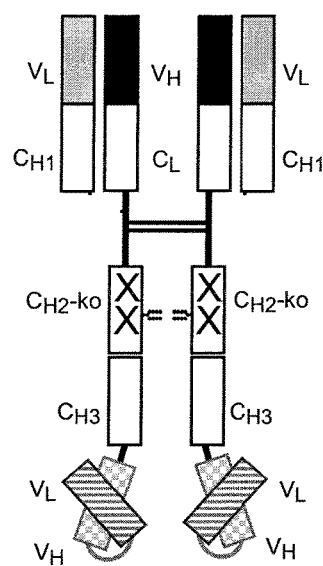
Figure 1:
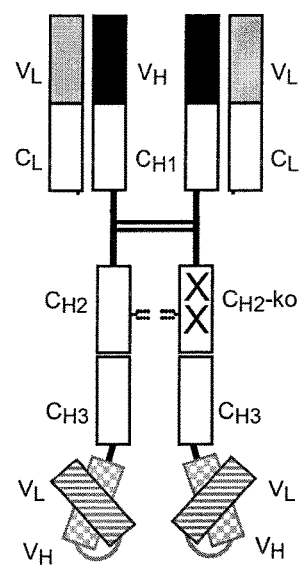
Figure 1:
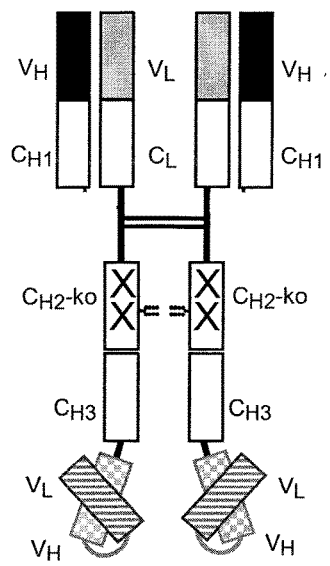
Figure 1:
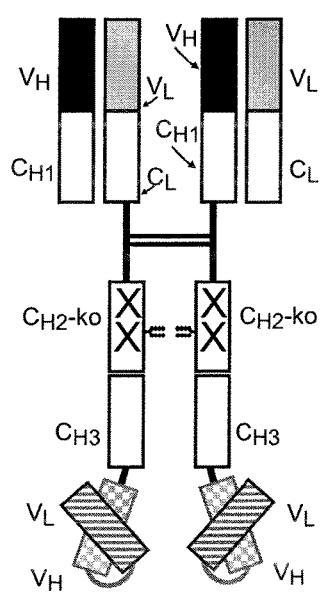
Figure 1:
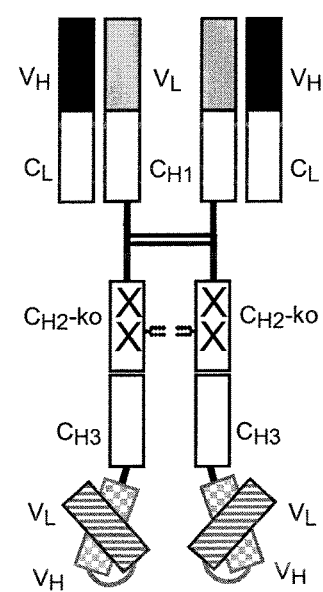
Figure 1:
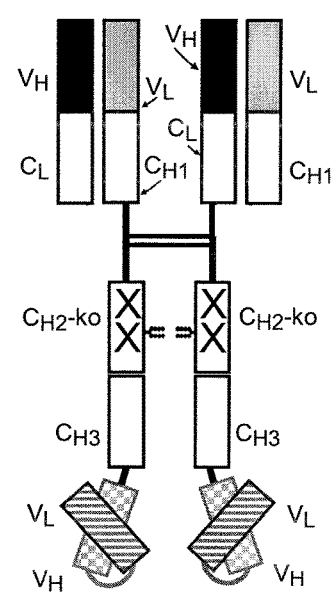
Figure 1:
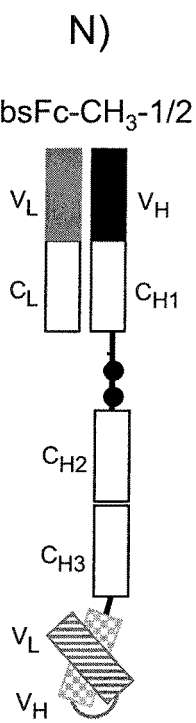

Further illustrative embodiments not depicted in FIG. 1A-1N include molecules where, relative to the depicted embodiments, the C-terminal single chain Fv-part may be in a VL-VH- rather than the depicted VH-VL-orientation, meaning that the VL domain is fused to the respective constant domain.

FIG. 1O lists illustrative modifications that can be introduced into the bivalent antibody variants depicted in FIGS. 1A-D and FIG. 1N to obtain Fc deficient derivatives as exemplified in FIG. 1E. Modifications are identical to those shown in FIG. 1P with the exception of the preserved cysteines (C226 and C229 in human IgG-antibodies). The numbering of amino acids is in line with the Kabat numbering [EU-Index]. wt=IgG1 humane wild type sequence (SEQ ID NO: 51 shows the amino acid positions corresponding to positions 213 to 242 according to Kabat numbering); bsFc-1/2 (SEQ ID NO: 52 shows the the amino acid positions corresponding to positions 213 to 242 according to Kabat numbering of bsFc-1/2); Δ1=knock-out (SEQ ID NO: 53 shows the amino acid positions corresponding to positions 213 to 242 according to Kabat numbering of Δ1); Glycan=Δ1-knock-out with deletion of saccharide moieties N297 (SEQ ID NO: 54 shows the amino acid positions corresponding to positions 213 to 242 according to Kabat numbering of Glycan); Δ2-5 further knock-out variants in continuation of Δ1 (SEQ ID NO: 55 shows the amino acid positions corresponding to positions 213 to 242 according to Kabat numbering of Δ2; SEQ ID NO: 56 shows the amino acid positions corresponding to positions 213 to 242 according to Kabat numbering of Δ3; SEQ ID NO: 57 shows the amino acid positions corresponding to positions 213 to 242 according to Kabat numbering of Δ4; SEQ ID NO: 58 shows the amino acid positions corresponding to positions 213 to 242 according to Kabat numbering of Δ5); —=the amino acid has been deleted.

FIG. 1P lists illustrative modifications that can be used to obtain a tetravalent molecule as depicted in FIG. 1F-M. The numbering of amino acids is in line with the Kabat numbering [EU-Index]. wt=IgG1 humane wild type sequence (SEQ ID NO: 51 shows the amino acid positions corresponding to positions 213 to 242 according to Kabat numbering); bsFc-1 (SEQ ID NO: 52 shows the the amino acid positions corresponding to positions 213 to 242 according to Kabat numbering of bsFc-1); Δ1=knock-out (SEQ ID NO: 60 shows the amino acid positions corresponding to positions 213 to 242 according to Kabat numbering of Δ1); Glycan=Δ1−knock-out with deletion of saccharide moieties N297 (SEQ ID NO: 61 shows the amino acid positions corresponding to positions 213 to 242 according to Kabat numbering of Glycan); 42-5 further knock-out variants in continuation of Δ1 (SEQ ID NO: 62 shows the amino acid positions corresponding to positions 213 to 242 according to Kabat numbering of Δ2; SEQ ID NO: 63 shows the amino acid positions corresponding to positions 213 to 242 according to Kabat numbering of Δ3; SEQ ID NO: 64 shows the amino acid positions corresponding to positions 213 to 242 according to Kabat numbering of Δ4, SEQ ID NO: 65 shows the amino acid positions corresponding to positions 213 to 242 according to Kabat numbering of Δ5); —=the amino acid has been deleted.

FIGS. 2A to 2C depict a schematic representation of the cloning procedure for the generation of an optimized heavy chain (main chain) for the antibodies depicted in FIG. 1, either as bivalent or tetravalent bispecific antibodies with modified ADCC-attenuated Fc-parts.
  i) The original vector, based on the plasmid-backbone of pcDNA3 (Invitrogen; CMV promoter and bovine growth hormone termination signal are deleted), is depicted. This plasmid contains the human γ1 isotype Ig heavy chain with regulatory elements of the immunoglobulin heavy chain locus.
  ii) The exchange of a VDJ (variable domain of the heavy chain) or VJ (variable domain of the light chain) element via the restriction endonuclease site AatII and ClaI is indicated.
  iii) the simple exchange (via restriction sites MluI and SpeI) of the complete human γ1 isotype Ig heavy chain against the coding sequence for a scFv fragment, a CH3-deleted and hinge and CH2 modified DNA element resulting in a bivalent bispecific antibody heavy chain is shown. For certain antibody variants, e.g. those depicted in FIG. 1D, the CH1 domain may be replaced by a CL-domain.
  iv) Exchanging the modified CH1-H—CH2 fragment (via restriction sites MluI and BspEI) against a hinge and CH2 modified CH1-H—CH2-CH3 element results in a tetravalent bispecific antibody heavy chain or as shown in v). If, in addition, or only as such the cysteines at position C226 and C229 are exchanged the resulting molecules are bivalent bispecific antibody molecules as depicted in FIG. 1N.
  v) Exchanging the scFv fragment (via restriction sites BspEI and SpeI) against a scFv-fragment of any other antigen specificity or of different VH and VL orientation. Substitutions iv) and v) can be combined.

In FIGS. 2B and 2C) the regions adjacent to the inserted VDJ-CH1 and scFv-elements, respectively, are shown in detail. SEQ ID NO: 66 shows the amino acids of the region spanning from position −19 of the L1 region to the first amino acid of the VDJ region (MGWSWIFLFLLSGTAGVLSQ). SEQ ID NO: 67 shows the amino acids of the region spanning from the last amino acid of the VDJ region to the third amino acid of the CH1 region (SASTK). SEQ ID NO: 68 shows the amino acids of the region between the CH3 region and the scFv fragment (QPSGDI).

FIGS. 2D-F depicts a schematic representation of the cloning procedure for the generation of the light chain of human monospecific antibodies.
  i) The parental vector, based on the plasmid backbone of pCR-Script (Stratagene; lacZ promoter and termination signal are deleted) contains the VJ region and the C region of human κ-gene as well as regulatory elements of the immunoglobulin light chain locus.
  ii) Exchange of a VJ (variable domain of the light chain) element or VDJ (variable domain of the heavy chain) element via the restriction endonucleases XhoI and SpeI.
  iii) Exchange of CL (constant light chain) element via the restriction endonucleases PmII and BsmBI.

In FIGS. 2E and 2F the regions adjacent to the inserted VJ and CL elements are shown in detail. SEQ ID NO: 69 shows the amino acids of the region spanning from position −20 of the L1 region to the first amino acid of the VJ region (MVFTPQILGLMLFWISGARGD). SEQ ID NO: 70 shows the amino acids of the region spanning from the last amino acid of the VJ region to the third amino acid of the CL region (KRTVA).

Boxes represent exons, circles enhancer elements and thin lines UT regions and intron sequences. $L_1$ and $L_2$, leader sequences encoded by two different exons (also shown in FIGS. 2B and 2E); V, variable regions; D, diversity region; J, joining regions; CH1, CH2, CH3, CL exons of constant heavy and light chains, respectively, H, hinge region, scFv single-chain Fv-fragment; X=amino acid modifications. NotI, AatII, ClaI, MluI, BspEI, SpeI, XhoI, KpnI, XhoI, SpeI, PmII, BsmBI, SalI, restriction endonucleases used for cloning; Amp$^R$ and Neo$^R$ represent the coding regions for Ampicillin and Neomycin resistance respectively.

The cleavage sites for secretory signal peptides are indicated by |; and exon-intron boundaries by [,].

FIG. 3A illustrates target cell restricted T cell activation ($^3$H-thymidine incorporation) by two bispecific antibodies of different format according to the invention, having FLT3× CD3 specificity. The antibodies are used on cells that do not (empty symbols) and that do (filled symbols) include FLT3/CD19-positive REH cells. ○,●: bivalent antibody molecule as depicted in FIG. 1A with the sequence "Glycan" as depicted in FIG. 1E and FIG. 1O (bsFc$^{ko}$-1/2-format) Fab fragment with FLT3 binding site, scFv fragment with CD3 binding site. □, ■: tetravalent antibody molecule as depicted in FIG. 1G with the sequence Δ1 as depicted in FIG. 1P, (bsFc$^{ko}$-1-format). Fab$_2$ fragment with FLT3 binding site, scFv fragment with CD3 binding site. *: intact monospecific anti-CD3 antibody without target cells. In the absence of target cells, intact monospecific CD3 antibodies effectively activate T cells in an Fc/FcR dependent manner whereas the bispecific antibodies are ineffective. This demonstrates that the bispecific format of the invention lack Fc/FcR binding as good as entirely. FIG. 3B illustrates target cell restricted T cell activation (TNF release) by different bivalent bispecific antibodies according to the invention, used on cells that do not (empty symbols) and that do (filled symbols) include FLT3/CD19-positive REH cells. ○, ●: bivalent antibody molecule as depicted in FIG. 1A with the sequence "Glycan" as depicted in FIG. 1E and FIG. 1O, Fab fragment with FLT3 binding site, scFv fragment with CD3 binding site; ◊, ♦: bivalent antibody molecule as depicted in 1E with the sequence "Glycan" as depicted in FIG. 1O, Fab fragment with CD19 binding site, scFv fragment with TCR binding site; ∇,▼: bivalent antibody molecule as depicted in FIG. 1E with the sequence "Glycan" as depicted in FIG. 1O, Fab fragment with CSPG4 binding site, scFv fragment with CD3 binding site. The chondroitinsulfate proteoglycan CSPG4 is a target antigen of melanoma cells and is not expressed on REH cells.

Figure 4:
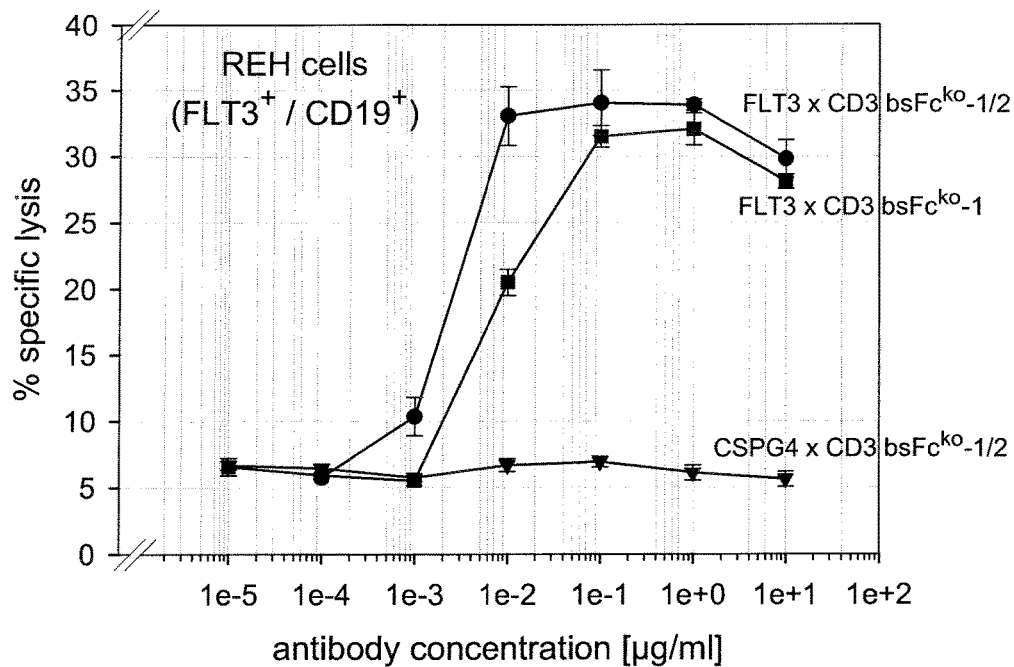
Figure 4:
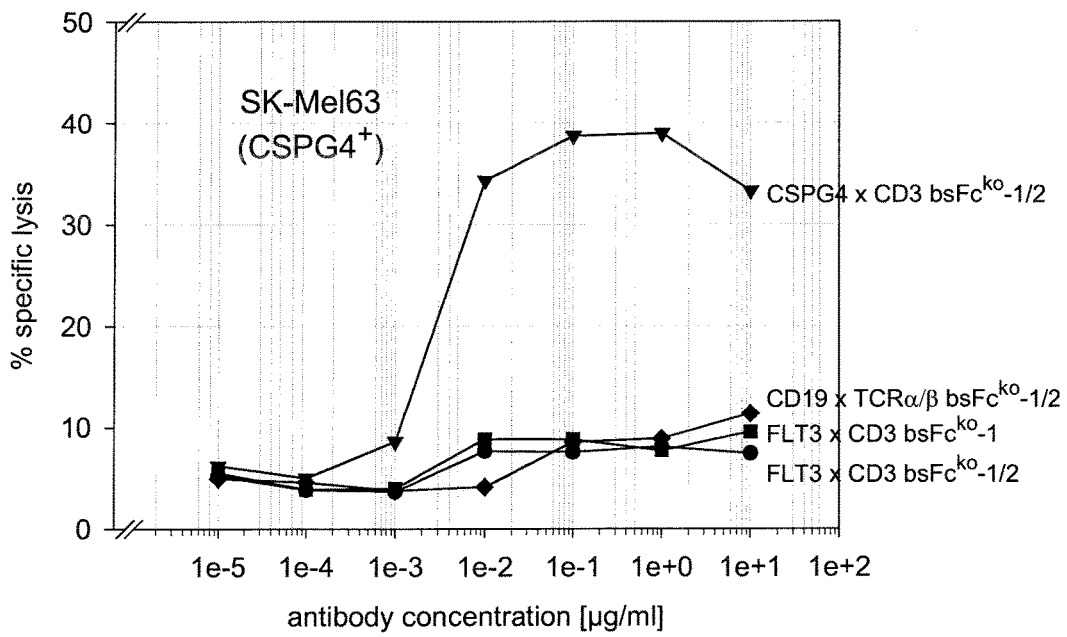

FIG. 4 depicts the specific lysis of FLT3/CD19 expressing REH cells (A) and CSPG expressing SKMel63 cells (B), respectively, by means of bispecific antibodies according to the invention and by activated CD8 positive T killer cells in a 4 hr $^{51}$chromium release test. ●: FLT3×CD3, bsFc$^{ko}$-1/2 format as depicted in FIG. 1E; ■: FLT3×CD3, bsFc$^{ko}$-1 format as depicted in FIG. 1G; ▼: CSPG4×CD3, bsFc$^{ko}$-1/2 format as depicted in FIG. 1E; ♦: CD19×TCR, bsFc$^{ko}$-1/2 format as depicted in FIG. 1E.

Figure 5:
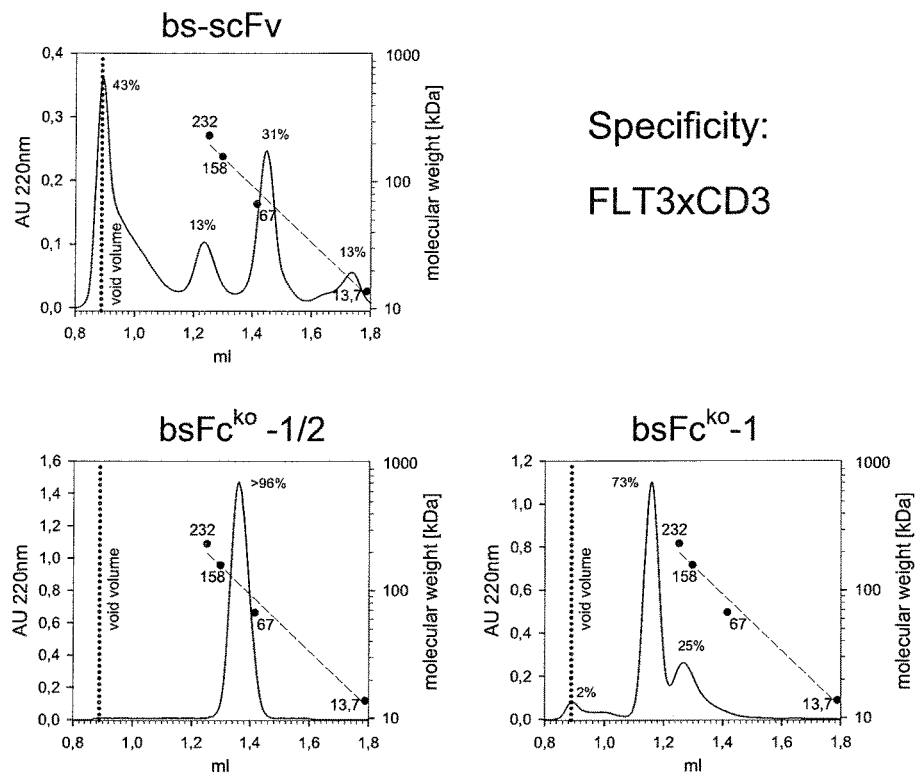
Figure 5:
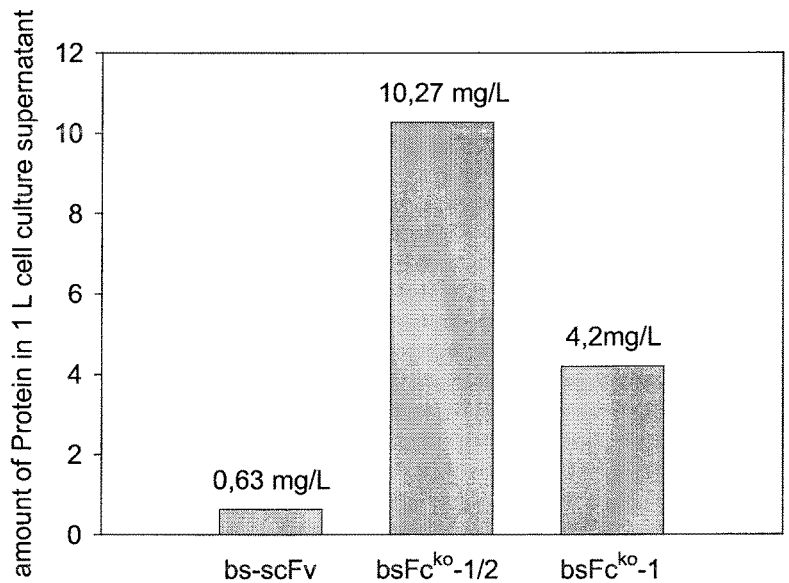

FIG. 5 shows a comparison of FLT3×CD3 antibodies of identical specificity in three different formats: bispecific single-chain format (bs-scFv), bsFc$^{ko}$-1/2 format as depicted in FIG. 1E, and bsFc$^{ko}$-1 format as depicted in FIG. 1G. A: determination of aggregation (values in percent) by means of gel filtration. Aggregates are migrating close to the void volume and are 43%, 0%, 2% for bs-scFv, bsFcko-1/2, bsFcko-1, respectively. It is concluded that formation of aggregates is considerably more pronounced if the antibody is expressed as bs-scFv rather than bsFcko-1/2 or bsFcko-1. B: production rate following transfection of antibody genes into production cells and purification via affinity chromatography. As can be seen, the formation of aggregates is significantly reduced for the two Fc$^{ko}$ formats according to the invention, and production rates are substantially higher than with the bispecific single chain format (bs-scFv).

FIG. 6A shows the sequences of illustrative light chains that may be included in an antibody of the invention. The respective peptide chains correspond to the mature protein without the corresponding leader peptide sequence. The sequences contain an N-terminal variable domain represented in bold and a C-terminal constant domain depicted in italic. The complementarity determining regions (CDRs) of the variable domain are underlined.

FIG. 6B depicts the sequences of illustrative main chains, which can in the present case also be addressed as heavy chains that may be included in an antibody of the invention. This particular main chain for the bsFc-1/2 format (FIG. 1E) includes a VH domain, a CH1 domain, a hinge region, a modified CH2 domain, a VL domain and a VH domain of a scFv fragment. In sequence example 21) (SEQ ID NO: 26) the main chain contains a CH3 domain as depicted in the example FIG. 1G-M (bsFc$^{ko}$-1-format).

The VH domains are depicted in bold the CH1 domain in regular, and the hinge, CH2 and CH3 regions in regular, underlined text. The main chain further includes a VL domain, which is depicted in bold, italic text, and a VH domain (bold) of a scFv fragment. The VH and the VL domains are coupled to each other via a linker, which is represented in italic, underlined text. The complementarity determining residues (CDRs) of the respective VL and VH regions are underlined. The CH2 domain and the scFv fragment are coupled to each other via a small linker (GQPSG), which is represented in italic.

DETAILED DESCRIPTION

The present invention relates to a recombinant bispecific antibody molecule. This antibody molecule is composed of elements that are also found in native, i.e. naturally occurring, immunoglobulins, namely domains of heavy chains and light chains of immunoglobulins.

The term "antibody" generally refers to a proteinaceous binding molecule with immunoglobulin-like functions. Typical examples of an antibody are immunoglobulins, as well as derivatives or functional fragments thereof which still retain the binding specificity. Techniques for the production of antibodies are well known in the art. The term "antibody" also includes immunoglobulins (Ig's) of different classes (i.e. IgA, IgG, IgM, IgD and IgE) and subclasses (such as IgG1, IgG2 etc.). Illustrative examples of an antibody are F$_{ab}$ fragments, F(ab')$_2$, F$_V$ fragments, single-chain F$_V$ fragments (scF$_V$), diabodies or domain antibodies (Holt L J et al., Trends Biotechnol. 21(11), 2003, 484-490). Domain antibodies may be single domain antibodies, single variable domain antibodies or immunoglobulin single variable domain having only one variable domain, which may be VH or VL, that specifically bind an antigen or epitope independently of other V regions or domains. Such an immunoglobulin single variable domain may not only encompass an isolated antibody single variable domain polypeptide, but also a larger polypeptide that includes or consists of one or more monomers of an antibody single variable domain polypeptide sequence. The definition of the term "antibody" thus also includes embodiments such as chimeric, single chain and humanized antibodies.

An antibody molecule according to the invention may carry one or more domains that have a sequence with at least about 60%, at least about 70%, at least about 75%, at least about 80%, at least about 85%, at least about 90%, at least about 92%, at least about 95%, at least about 96%, at least about 97%, at least about 98% or at least about 99% sequence identity with a corresponding naturally occurring domain of an immunoglobulin M, an immunoglobulin G, an immunoglobulin A, an immunoglobulin D or an immunoglobulin E. It is noted in this regard, the term "about" or "approximately" as used herein means within a deviation of 20%, such as within a deviation of 10% or within 5% of a given value or range.

Accordingly, the main chain (longer polypeptide chain) of an antibody molecule of the invention may include, including consist of, domains with the above sequence identity with a corresponding domain of an immunoglobulin mu heavy chain, of an immunoglobulin gamma heavy chain, of an immunoglobulin alpha heavy chain, of an immunoglobulin delta heavy chain or of an immunoglobulin epsilon heavy chain. Further, an antibody molecule of the invention may include, including consist of, domains with the above sequence identity with a corresponding domain of an immunoglobulin lambda light chain or of an immunoglobulin kappa light chain. In some embodiments the entire heavy chain domains of an antibody molecule according to the invention have at least about 60%, at least about 70%, at least about 75%, at least about 80%, at least about 85%, at least about 90%, at least about 92%, at least about 95%, at least about 97%, at least about 98% or at least about 99% sequence identity with the corresponding regions of an immunoglobulin mu heavy chain, of an immunoglobulin gamma heavy chain (such as gamma 1, gamma 2, gamma 3 or gamma 4 heavy chains), of an immunoglobulin alpha heavy chain (such as alpha 1 or alpha 2 heavy chains), of an immunoglobulin delta heavy chain or of an immunoglobulin epsilon heavy chain. In some embodiments all light chain domains present in an antibody molecule according to the invention have at least about 60%, at least about 70%, at least about 75%, at least about 80%, at least about 85%, at least about 90%, at least about 92%, at least about 95%, at least about 97%, at least about 98% or at least about 99% sequence identity with the corresponding regions of an immunoglobulin lambda light chain (such as lambda 1, lambda 2, lambda 3 or lambda 4 light chains) or of an immunoglobulin kappa light chain.

"Percent (%) sequence identity" with respect to amino acid sequences disclosed herein is defined as the percentage of amino acid residues in a candidate sequence that are pair-wise identical with the amino acid residues in a reference sequence, i.e. an antibody molecule of the present disclosure, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publically available computer software such as BLAST, ALIGN, or Megalign (DNASTAR) software. Those skilled in the art can determine appropriate parameters for measuring alignment, including any algorithms needed to achieve maximum alignment over the full length of the sequences being compared. The same is true for nucleotide sequences disclosed herein.

The term "variable" refers to the portions of the immunoglobulin domains that exhibit variability in their sequence and that are involved in determining the specificity and binding affinity of a particular antibody (i.e., the "variable domain(s)"). Variability is not evenly distributed throughout the variable domains of antibodies; it is concentrated in sub-domains of each of the heavy and light chain variable regions. These sub-domains are called "hypervariable regions", "HVR," or "HV," or "complementarity determining regions" (CDRs). The more conserved (i.e., non-hypervariable) portions of the variable domains are called the "framework" regions (FR). The variable domains of naturally occurring heavy and light chains each include four FR regions, largely adopting a β-sheet configuration, connected by three hypervariable regions, which form loops connecting, and in some cases forming part of, the β-sheet structure. The hypervariable regions in each chain are held together in close proximity by the FR and, with the hypervariable regions from the other chain, contribute to the formation of the antigen-binding site (see Kabat et al., see below). Generally, naturally occurring immunoglobulins include six CDRs (see below); three in the VH (H1, H2, H3), and three in the VL (L1, L2, L3). In naturally occurring immunoglobulins, H3 and L3 display the most diversity of the six CDRs, and H3 in particular is believed to play a unique role in conferring fine specificity to immunoglobulins. The constant domains are not directly involved in antigen binding, but exhibit various effector functions, such as, for example, antibody-dependent, cell-mediated cytotoxicity and complement activation.

The corresponding immunoglobulin mu heavy chain, gamma heavy chain, alpha heavy chain, delta heavy chain, epsilon heavy chain, lambda light chain or kappa light chain may be of any species, such as a mammalian species, including a rodent species, an amphibian, e.g. of the subclass Lissamphibia that includes e.g. frogs, toads, salamanders or newts or an invertebrate species. Examples of mammals include, but are not limited to, a rat, a mouse, a rabbit, a guinea pig, a squirrel, a hamster, a hedgehog, a platypus, an American pika, an armadillo, a dog, a lemur, a goat, a pig, a cow, an opossum, a horse, a bat, a woodchuck, an orang-utan, a rhesus monkey, a woolly monkey, a macaque, a chimpanzee, a tamarin (saguinus oedipus), a marmoset or a human.

The term "immunoglobulin" refers to a glycoprotein that includes at least two heavy (H) chains and two light (L) chains linked by disulfide bonds, or an antigen binding portion thereof. Each heavy chain has a heavy chain variable region (abbreviated herein as $V_H$) and a heavy chain constant region. In some embodiments the heavy chain constant region includes three domains, $C_{H1}$, $C_{H2}$ and $C_{H3}$. Each light chain has a light chain variable region (abbreviated herein as $V_L$) and a light chain constant region. The light chain constant region includes one domain, $C_L$. The $V_H$ and $V_L$ regions can be further subdivided into regions of hypervariability, termed complementarity determining regions (CDR), interspersed with regions that are more conserved, termed framework regions (FR). The CDRs contain most of the residues responsible for specific interactions of the antibody with the antigen. Each $V_H$ and $V_L$ has three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an epitope of an antigen.

Each light chain of an immunoglobulin includes an N-terminal variable (V) domain (VL) and a constant (C) domain (CL). Each heavy chain includes an N-terminal V domain (VH), three or four C domains (CHs), and a hinge region. An antibody molecule according to the invention likewise contains these domains and regions (even though one binding site of the bispecific antibody molecule is only formed by a single chain Fv fragment).

An immunoglobulin when used herein, is typically a tetrameric glycosylated protein composed of two light (L) chains of approximately 25 kDa each and two heavy (H) chains of approximately 50 kDa each. Two types of light chain, termed lambda and kappa, may be found in immunoglobulins. Depending on the amino acid sequence of the constant domain of heavy chains, immunoglobulins can be assigned to five major classes: A, D, E, G, and M, and several of these may be further divided into subclasses (isotypes), e.g., IgG1, IgG2, IgG3, IgG4, IgA1, and IgA2. An IgM immunoglobulin consists of 5 of the basic heterotetramer unit along with an additional polypeptide called a J chain, and contains 10 antigen binding sites, while IgA immunoglobulins contain from 2-5 of the basic 4-chain units which can polymerize to form polyvalent assemblages in combination with the J chain. In the case of IgGs, the 4-chain unit is generally about 150,000 daltons.

The term "amino acid" or "amino acid residue" refers to an α- or β-amino carboxylic acid.

When used in connection with a protein or peptide, the term "amino acid" or "amino acid residue" typically refers to an α-amino carboxylic acid having its art recognized definition such as an amino acid selected from the group consisting of: L-alanine (Ala or A); L-arginine (Arg or R); L-asparagine (Asn or N); L-aspartic acid (Asp or D); L-cysteine (Cys or C); L-glutamine (Gln or Q); L-glutamic acid (Glu or E); glycine (Gly or G); L-histidine (His or H); L-isoleucine (ILE or I): L-leucine (Leu or L); L-lysine (Lys or K); L-methionine (Met or M); L-phenylalanine (Phe or F); L-proline (Pro or P); L-serine (Ser or S); L-threonine (Thr or T); L-tryptophan (Trp or W); L-tyrosine (Tyr or Y); and L-valine (Val or V), although modified, synthetic, or rare amino acids such as e.g. taurine, ornithine, selenocysteine, homocystine, hydroxyproline, thioproline, iodo-tyrosine, 3-nitro-tyrosine, ornithine, citrulline, canavanine, 5-hydroxytryptophane, carnosine, cycloleucine, 3,4-dihydroxyphenylalanine, N-acetylcysteine, prolinol, allylglycine or acetidine-2-carboxylic acid may be used as desired. Generally, amino acids can be grouped as having a nonpolar side chain (e.g., Ala, Cys, ILE, Leu, Met, Phe, Pro, Val); a negatively charged side chain (e.g., Asp, Glu); a positively charged sidechain (e.g., Arg, His, Lys); or an uncharged polar side chain (e.g., Asn, Cys, Gln, Gly, His, Met, Phe, Ser, Thr, Trp, and Tyr).

The term "epitope", also known as the "antigenic determinant", refers to the portion of an antigen to which an antibody or T-cell receptor specifically binds, thereby forming a complex. Thus, the term "epitope" includes any molecule or protein determinant capable of specific binding to an immunoglobulin or T-cell receptor. The binding site(s) (paratope) of an antibody molecule described herein may specifically bind to/interact with conformational or continuous epitopes, which are unique for the target structure. Epitopic determinants usually consist of chemically active surface groupings of molecules such as amino acids or sugar side chains and usually have specific three dimensional structural characteristics, as well as specific charge characteristics. In some embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. With regard to polypeptide antigens a conformational or discontinuous epitope is characterized by the presence of two or more discrete amino acid residues, separated in the primary sequence, but assembling to a consistent structure on the surface of the molecule when the polypeptide folds into the native protein/antigen (Sela, M., Science (1969) 166, 1365-1374; Laver, W. G., et al. Cell (1990) 61, 553-556). The two or more discrete amino acid residues contributing to the epitope may be present on separate sections of one or more polypeptide chain(s). These residues come together on the surface of the molecule when the polypeptide chain(s) fold(s) into a three-dimensional structure to constitute the epitope. In contrast, a continuous or linear epitope consists of two or more discrete amino acid residues, which are present in a single linear segment of a polypeptide chain. As an illustrative example, a "context-dependent" CD3 epitope refers to the conformation of said epitope. Such a context-dependent epitope, localized on the epsilon chain of CD3, can only develop its correct conformation if it is embedded within the rest of the epsilon chain and held in the right position by heterodimerization of the epsilon chain with either CD3 gamma or delta chain. In contrast thereto, a context-independent CD3 epitope may be an N-terminal 1-27 amino acid residue polypeptide or a functional fragment thereof of CD3 epsilon. Generally, epitopes can be linear in nature or can be a discontinuous epitope. Thus, as used herein, the term "conformational epitope" refers to a discontinuous epitope formed by a spatial relationship between amino acids of an antigen other than an unbroken series of amino acids. The term "epitope" also includes an antigenic determinant of a hapten, which is known as a small molecule that can serve as an antigen by displaying one or more immunologically recognized epitopes upon binding to larger matter such as a larger molecule e.g. a protein.

An antibody or antibody molecule/fragment is said to specifically bind to an antigen when it recognizes its target antigen in a complex mixture of proteins and/or macromolecules. Antibodies are said to "bind to the same epitope" if the antibodies cross-compete so that only one antibody can bind to the epitope at a given point of time, i.e. one antibody prevents the binding or modulating effect of the other.

The term "specific" in this context, or "specifically recognizing", also used as "directed to", means in accordance with this invention that the antibody molecule is capable of specifically interacting with and/or binding to at least two, e.g. at least three or at least four amino acids of an epitope but does not essentially bind to another epitope or antigen. Such binding may be exemplified by the specificity of a "lock-and-key-principle". Specific binding is believed to be effected by specific motifs in the amino acid sequence of the binding region of the antibody, and the antibody and the epitope or the antigen bind to each other as a result of their primary, secondary or tertiary structure as well as the result of secondary modifications of said structure. The specific interaction of the epitope/antigen-interaction-site with its specific epitope/antigen may result as well in a simple binding of said site to the antigen. Moreover, the specific interaction of the antigen-interaction-site with its specific epitope/antigen may alternatively result in the initiation of a signal, such as for instance due to the induction of a change of the conformation of the antigen or an oligomerization of the antigen.

Typically, binding is considered specific when the binding affinity is higher than $10^{-6}$ M. In particular, binding is considered specific when binding affinity is about $10^{-8}$ to $10^{-11}$ M ($K_D$), or of about $10^{-9}$ to $10^{-11}$ M or even higher. Thus, antibody molecules with an affinity of the first binding site and/or the second binding site in the picomolar range (with a $K_D$ of $10^{-12}$M) are also encompassed in the present invention. If necessary, nonspecific binding of a binding site can be reduced without substantially affecting specific binding by varying the binding conditions.

In some embodiments an antigen to which an antibody according to the invention binds is an antigen that is included in the extracellular matrix or it is a cell surface antigen. In some embodiments an antigen to which an antibody according to the invention binds is a tumor associated antigen. It is understood that such a tumour associated antigen may be included in the extracellular matrix or be a cell surface antigen.

The term "extracellular matrix" refers to the tissue region of a multicellular animal, including a human that is found in the intercellular space, i.e. between the cells of the respective tissue. The extracellular matrix is largely a network of proteins such as fibrillar and non-fibrillar collagens or elastin, of glycoproteins such as laminin or fibronectin, of proteoglycans, such as chondroitin sulfate or keratan sulphate and of polysaccharides such as Hyaluronic acid. The extracellular matrix serves inter alia in segregating different tissues from each other or in regulating intercellular communication. In some embodiments a tumor associated antigen may be expressed partly or exclusively at the extracellular matrix of a tumor.

The term "cell surface antigen" as used herein refers to a molecule that is displayed on the surface of a cell. Typically such a molecule is located in or on the plasma membrane of the cell such that at least part of this molecule remains accessible from the ambience, i.e. from outside the cell. A respective molecule consists of or includes typically amino acid and/or saccharide moieties. An illustrative example of a cell surface molecule, which is located in the plasma membrane, is a transmembrane protein that, in its three-dimensional conformation, has regions of hydrophilicity and hydrophobicity. One or more hydrophobic region(s) allow(s) the cell surface molecule to be embedded, or inserted in the hydrophobic plasma membrane of the cell whereas hydrophilic regions of the protein extend on either side of the plasma membrane into the cytoplasm and extracellular space, respectively. Examples of a cell surface molecule located on the plasma membrane include, but are not limited to, a protein with a posttranslationally modified cysteine residue carrying a palmitoyl group, a protein modified at a C-terminal cysteine residue carrying a farnesyl group or a protein modified at the C-terminus carrying a glycosyl phosphatidyl inositol ("GPI") anchor. These groups allow covalent attachment of proteins to the outer surface of the plasma membrane, where they remain accessible for recognition by extracellular molecules such as antibodies. Examples of cell surface antigens include a cell surface receptor molecule such as a G protein coupled receptor (e.g. the β adrenergic receptor), a tyrosin kinase receptor (such as EGFR, EGFRvIII, Her2/neu, HER2/c-neu, PDGFRα, ILR-1, TNFR, CD30, CD33 or GMCSFR), a membrane receptor with associated tyrosin kinase activity (such as IL6R or LIFR) or a membrane receptor with Ser/Thr kinase activity (such as TGFβR), to name only a few examples.

Examples of a tumor associated antigen that is included in the extracellular matrix include, but are not limited to, a proteoglycan such as Melanoma-associated Chondroitin Sulfate Proteoglycan (CSPG4) or CD44v6, including a mucin such as Muc-1 or a membrane-bound enzyme such as Carbonic anhydrase IX (CAIX). Examples for such antigens are tenascin and the fibroblast activating protein (FAP).

The term "isolated antibody molecule" as used herein refers to an antibody molecule that has been identified and separated and/or recovered from a component of its natural environment. Contaminant components of its natural environment are matter that would interfere with diagnostic or therapeutic uses for the antibody, and may include enzymes, hormones, and other proteinaceous or nonproteinaceous solutes. In some embodiments the antibody molecule is purified to greater than 95% by weight of antibody as determined by the Lowry method, such as more than 99% by weight. In some embodiments the antibody molecule is purified to a degree sufficient to obtain at least 15 residues of N-terminal or internal amino acid sequence by use of a spinning cup sequenator. In some embodiments the antibody is purified to homogeneity as judged by SDS-PAGE under reducing or nonreducing conditions using Coomassie blue or, preferably, silver stain. An isolated antibody molecule may in some embodiments be present within recombinant cells with one or more component(s) of the antibody's natural environment not being present. Typically an isolated antibody is prepared by at least one purification step.

The terms "$V_H$" and "$V_L$" are used herein to refer to the heavy chain variable domain and light chain variable domain respectively of an immunoglobulin. An immunoglobulin light or heavy chain variable region consists of a "framework" region interrupted by three hypervariable regions. Thus, the term "hypervariable region" refers to the amino acid residues of an antibody which are responsible for antigen binding. The hypervariable region includes amino acid residues from a "Complementarity Determining Region" or "CDR". There are three heavy chains and three light chain CDRs (or CDR regions) in the variable portion of an immunoglobulin. Thus, "CDRs" as used herein refers to all three heavy chain CDRs (CDRH1, CDRH2 and CDRH3), or all three light chain CDRs (CDRL1, CDRL2 and CDRL3) or both all heavy and all light chain CDRs, if appropriate. Three CDRs make up the binding character of a light chain variable region and three make up the binding character of a heavy chain variable region. CDRs determine the antigen specificity of an immunoglobulin molecule and are separated by amino acid sequences that include scaffolding or framework regions. The exact definitional CDR boundaries and lengths are subject to different classification and numbering systems. The structure and protein folding of the antibody may mean that other residues are considered part of the antigen binding region and would be understood to be so by a skilled person. CDRs provide the majority of contact residues for the binding of the immunoglobulin to the antigen or epitope.

CDR3 is typically the greatest source of molecular diversity within the antibody-binding site. H3, for example, can be as short as two amino acid residues or greater than 26 amino acids. The subunit structures and three-dimensional configurations of different classes of immunoglobulins are well known in the art. For a review of the antibody structure, see Antibodies: A Laboratory Manual, Cold Spring Harbor Laboratory, eds. Harlow et al., 1988. One of skill in the art will recognize that each subunit structure, e.g., a CH, VH, CL, VL, CDR, FR structure, includes active fragments, e.g., the portion of the VH, VL, or CDR subunit binds to the antigen, i.e., the antigen-binding fragment, or, e.g., the portion of the CH subunit that binds to and/or activates, e.g., an Fc receptor and/or complement. The CDRs typically refer to the Kabat CDRs, as described in Sequences of Proteins of immunological Interest, US Department of Health and Human Services (1991), eds. Kabat et al. Another standard for characterizing the antigen binding site is to refer to the hypervariable loops as described by Chothia. See, e.g., Chothia, et al. (1992; J. Mol. Biol. 227:799-817; and Tomlinson et al. (1995) EMBO J. 14:4628-4638. Still another standard is the AbM definition used by Oxford Molecular's AbM antibody modelling software. See, generally, e.g., Protein Sequence and Structure Analysis of Antibody Variable Domains. In: Antibody Engineering Lab Manual (Ed.: Duebel, S. and Kontermann, R., Springer-Verlag, Heidelberg). Embodiments described with respect to Kabat CDRs can alternatively be implemented using similar described relationships with respect to Chothia hypervariable loops or to the AbM-defined loops.

"Framework Region" or "FR" residues are those variable domain residues other than the hypervariable region. The sequences of the framework regions of different light or heavy chains are relatively conserved within a species. Thus, a "human framework region" is a framework region that is substantially identical (about 85% or more, usually 90-95% or more) to the framework region of a naturally occurring human immunoglobulin. The framework region of an antibody, that is the combined framework regions of the constituent light and heavy chains, serves to position and align the CDR's. The CDR's are primarily responsible for binding to an epitope of an antigen.

The terms "Fab", "Fab region", "Fab portion" or "Fab fragment" are understood to define a polypeptide that includes a $V_H$, a $C_H1$, a $V_L$, and a $C_L$ immunoglobulin domain. Fab may refer to this region in isolation, or this region in the context of an antibody molecule according to the invention, as well as a full length immunoglobulin or immunoglobulin fragment. Typically a Fab region contains an entire light chain of an antibody. A Fab region can be taken to define "an arm" of an immunoglobulin molecule. It contains the epitope-binding portion of that Ig. The Fab region of a naturally occurring immunoglobulin can be obtained as a proteolytic fragment by a papain-digestion. A "F(ab')$_2$ portion" is the proteolytic fragment of a pepsin-digested immunoglobulin. A "Fab' portion" is the product resulting from reducing the disulfide bonds of an F(ab')$_2$ portion. As used herein the terms "Fab", "Fab region", "Fab portion" or "Fab fragment" may further include a hinge region that defines the C-terminal end of the antibody arm (cf. above). This hinge region corresponds to the hinge region found C-terminally of the $C_H1$ domain within a full length immunoglobulin at which the arms of the antibody molecule can be taken to define a Y. The term hinge region is used in the art because an immunoglobulin has some flexibility at this region.

An "Fv" or "Fv fragment" consists of only the $V_L$ and $V_H$ domains of a "single arm" of an immunoglobulin. Thus an "Fv" is the minimum antibody fragment which contains a complete antigen-recognition and binding site. A "two-chain" Fv fragment consists of a dimer of one heavy- and one light-chain variable domain in tight, non-covalent association. A single-chain Fv species (scFv) includes a $V_H$ and a $V_L$ domain of an immunoglobulin, with these domains being present in a single polypeptide chain in which they are covalently linked to each other by a flexible peptide linker. Typically, in a scFv fragment the variable domains of the light and heavy chain associate in a dimeric structure analogous to that in a two-chain Fv species. In single chain Fv fragments, it is possible to either have the variable domain of the light chain arranged at the N-terminus of the single polypeptide chain, followed by the linker and the variable domain of the heavy chain arranged at the C-terminus of the polypeptide chain or vice versa, having the variable domain of the heavy chain arranged on the N-terminus and the variable domain of the light chain at the C-terminus with the peptide linker arranged inbetween. The peptide linker can be any flexible linker known in the art, for example, made from glycine and serine residues. It is also possible to additionally stabilize the domain association between the $V_H$ and the $V_L$ domain by introducing disulfide bonds into conserved framework regions (see Reiter et al. Stabilization of the Fv fragments in recombinant immunotoxins by disulfide bonds engineered into conserved framework regions, Biochemistry 1994, 33, 6551-5459). Such scFv fragments are also known as disulfide-stabilized scFv fragments (ds-scFv).

The term "Fc region" or "Fc fragment" is used herein to define a C-terminal region of an immunoglobulin heavy chain, including native-sequence Fc regions and variant Fc regions. The Fc part mediates the effector function of antibodies, e.g. the activation of the complement system and of Fc-receptor bearing immune effector cells, such as NK cells. In human IgG molecules, the Fc region is generated by papain cleavage N-terminal to Cys226. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody molecule, or by recombinantly engineering the nucleic acid encoding a heavy chain of the antibody antibody molecule. Accordingly, a composition of intact antibodies may include antibody populations with all K447 residues removed, antibody populations with no K447 residues removed, and antibody populations having a mixture of antibodies with and without the K447 residue. Suitable native-sequence Fc regions for use in the antibodies of the invention include mammalian, e.g. human or murine, IgG1, IgG2 (IgG2A, IgG2B), IgG3 and IgG4. The Fc region contains two or three constant domains, depending on the class of the antibody. In embodiments where the immunoglobulin is an IgG the Fc region has a $C_H2$ and a $C_H3$ domain.

An antibody molecule according to the invention has two chains, a shorter chain, which may in some embodiments be a light chain, and a main chain, which may in some embodiments also be addressed as the heavy chain. The antibody molecule is usually a dimer of these two chains. On the basis of the domains included in an antibody molecule of the invention the antibody molecule can be taken to have a Fab fragment, which generally includes a hinge region, a $C_H2$ domain and a single chain Fv fragment. In some embodiments the antibody molecule also has a $C_H3$ domain, generally arranged C-terminally of the $C_H2$ domain. In some embodiments the arrangement of the domains of an antibody of the invention corresponds to the arrangement of domains in an immunoglobulin. As two examples, the shorter chain of an antibody molecule of the invention may have a VL domain at the N-terminus and a CL domain at the C-terminus of the shorter chain, and the main chain may have a VH domain at the N-terminus and a CH1 domain C-terminally thereto. In some embodiments the shorter chain may have a VL domain at the N-terminus and a CH1 domain at the C-terminus of the shorter chain. In some embodiments the shorter chain may have a VH domain at the N-terminus and a CH1 domain at the C-terminus of the shorter chain. In some embodiments the shorter chain may have a VH domain at the N-terminus and a CL domain at the C-terminus of the shorter chain. In some embodiments the main chain may have a VL domain at the N-terminus and a CH1 domain C-terminally thereto. In some embodiments the main chain may have a VH domain at the N-terminus and a CL domain C-terminally thereto. In some embodiments the main chain may have a VL domain at the N-terminus and a CL domain C-terminally thereto.

The shorter chain of the antibody may be linked to the main chain of the antibody by means of one or more, including two or three, disulphide bonds. A respective disulphide bond may define a bridge between a C-terminal cysteine residue of the smaller chain and a cysteine residue within the hinge region of the main chain of the antibody.

In an antibody molecule according to the invention the C-terminal region of the main chain may be defined by a single chain Fv fragment. The C-terminus of the main chain may in some embodiments be defined by the VH domain of the scFv fragment. In some embodiments the C-terminus of the main chain may be defined by the VL domain of the scFv fragment. Accordingly, the scFv fragment may in some embodiments be coupled to the CH2 domain or to the CH3 domain, if present, of the main chain via the VH domain, e.g. the N-terminal end of the VH domain. In some embodiments the scFv fragment may be coupled to the CH2 domain or to the CH3 domain, if present, of the main chain via the VL domain, e.g. the N-terminal end of the VL domain. In some embodiments the CH2 domain of the antibody molecule or the CH3 domain, if present, is linked to the scFv fragment via the variable domain of the light chain (VL domain) of the scFv fragment. In some embodiments the CH2 domain is linked to the scFv fragment via the variable domain of the heavy chain (VH domain) of the scFv fragment.

The Fab fragment of an antibody molecule according to the invention is in some embodiments linked to the CH2 domain via a heavy chain domain of the Fab fragment. Accordingly, the main chain of the antibody may have a heavy chain domain such as a CH1 domain (supra), which is coupled to the CH2 domain. As explained above, a respective CH1 domain may be coupled to the CH2 domain via a hinge region. The respective heavy chain domain of the Fab fragment may in some embodiments be arranged at the N-terminus of the polypeptide chain of the main chain of the antibody. In some embodiments the Fab fragment of an antibody molecule according to the invention is linked to the CH2 domain via a light chain domain of the Fab fragment. Accordingly, the main chain of the antibody molecule may have a light chain domain such as a CL domain, which is coupled to the CH2 domain. Again, a respective CL domain may be coupled to the CH2 domain via a hinge region. The respective light chain domain of the Fab fragment may in some embodiments be arranged at the N-terminus of the polypeptide chain of the main chain of the antibody molecule. To prevent dimerization of the molecules in bivalent embodiments (FIG. 1A-E and 1 N) the cysteine residues in the hinge region providing inter-chain disulfide bonds may be exchanged. In tetravalent embodiments (FIGS. 1F-M) these cysteine residues are preserved. In these embodiments the antibody molecule can accordingly be taken to define a dimer of a bivalent, dimeric antibody molecule as described above and each main chain and each shorter chain can be individually selected. As an example, the first of the shorter chains may have a VH domain at the N-terminus and a CL domain at the C-terminus. The first main chain may have a VL domain at the N-terminus and a CH1 domain C-terminally thereto. Further, the first main chain may have a CH2 and a CH3 domain, as well as a C-terminal scFv fragment. The scFv fragment may be coupled to the CH3 domain via the VL domain. The second of the shorter chains may have a VH domain at the N-terminus and a CH1 domain at the C-terminus. The second main chain may have a VL domain at the N-terminus and a CL domain C-terminally thereto. The second main chain may also have a CH2 and a CH3 domain, as well as a C-terminal scFv fragment. The scFv fragment may be coupled to the CH3 domain via the VL domain.

A respective tetrameric antibody molecule may be composed of two dimeric antibody molecules that are linked to each other via one or more, such as two, disulphide bonds. Such a disulphide bond may define a bridge between a cysteine residue of the main chain of a first dimeric antibody molecule and a cysteine residue of the main chain of a second dimeric antibody molecule. Typically, the respective cysteine residues are positioned within the hinge region of the corresponding main chain of each dimeric antibody molecule. In some embodiments one or both of the two main chains, i.e. the main chain of the first dimeric molecule and the main chain of the second dimeric molecule of a tetrameric antibody molecule, have a cysteine residue at sequence position 226 and/or at sequence position 229 of one of the respective hinge domain, in line with the Kabat numbering [EU-Index]. In one embodiment a disulphide bond between the hinge domain of the first main chain and a hinge domain of the second main chain is defined by at least one of a cysteine residue at sequence position 226 and a cysteine residue at sequence position 229 of one of the hinge domains, according to the Kabat numbering [EU-Index]. In some embodiments a tetrameric antibody molecule may have one or more disulphide bonds linking the hinge regions of the two main chains of the dimeric antibody molecules and a disulphide bond linking the hinge regions of the two main chains of the dimeric antibody molecules. In some embodiments two dimeric antibody molecules of a tetrameric antibody molecule according to the invention may be linked by means of a disulphide bond that is defined by a cysteine residue that is included in the CH2 domain of the main chain of a first dimeric antibody molecule and a cysteine residue that is included in the CH2 domain of the main chain of a second dimeric antibody molecule.

As a further example, the first of the shorter chains may have a VL domain at the N-terminus and a CH1 domain at the C-terminus. The first main chain may have a VH domain at the N-terminus and C-terminally linked thereto a CL domain. Further, the first main chain may have a CH2 and a CH3 domain, as well as a C-terminal scFv fragment. The scFv fragment may be coupled to the CH3 domain via the VH domain. The second of the shorter chains may have a VL domain at the N-terminus and a CL domain at the C-terminus. The second main chain may have a VH domain at the N-terminus and a CH1 domain C-terminally thereto. The second main chain may also have a CH2 and a CH3 domain, as well as a C-terminal scFv fragment. The scFv fragment may be coupled to the CH3 domain via the VH domain.

A "bispecific" or "bifunctional" antibody molecule is an antibody molecule that has two different epitope/antigen binding sites, and accordingly has binding specificities for two different target epitopes. These two epitopes may be epitopes of the same antigen or of different antigens. In contrast thereto a "bivalent antibody" may have binding sites of identical antigenic specificity.

A "bispecific antibody" may be an antibody molecule that binds one antigen or epitope on one of two or more binding arms, defined by a first pair of heavy and light chain or of main and shorter/smaller chain (supra), and binds a different antigen or epitope on a second arm, defined by a second pair of heavy and light chain or of main and smaller chain. Such an embodiment of a bispecific antibody has two distinct antigen binding arms, in both specificity and CDR sequences. Typically, a bispecific antibody is monovalent for each antigen it binds to. A bispecific antibody is a hybrid antibody molecule, which may have a first binding region that is defined by a first light chain variable region and a first heavy chain variable region, and a second binding region that is defined by a second light chain variable region and a second heavy chain variable region. In some embodiments one of these binding regions may be defined by a heavy/light chain pair. As explained above, in the context of the present invention the bispecific antibody molecule has a first binding site, defined by variable regions of a main chain and a smaller chain, and a second, different binding site defined by a variable region of a scFv fragment that is included in the main chain of the antibody molecule.

Methods of making a bispecific antibody molecule are known in the art, e.g. chemical conjugation of two different monoclonal antibodies or for example, also chemical conjugation of two antibody fragments, for example, of two Fab fragments. Alternatively, bispecific antibody molecules are made recombinantly. Traditionally, the recombinant production of bispecific antibodies is based on the co-expression of two immunoglobulin H chain-L chain pairs, where the two H chains have different binding specificities. Because of the random assortment of H and L chains, a potential mixture of ten different antibody structures are produced of which only one has the desired binding specificity. An alternative approach involves fusing the variable domains with the desired binding specificities to heavy chain constant region including at least part of the hinge region, CH2 and CH3 regions. In one embodiment the CH1 region containing the site necessary for light chain binding is present in at least one of the fusions. DNA encoding these fusions, and if desired the L chain are inserted into separate expression vectors and are then co-transfected into a suitable host organism. It is possible though to insert the coding sequences for two or all three chains into one expression vector.

The bispecific antibody molecule of the invention can act as a monoclonal antibody (MAb) with respect to each target. In some embodiments the antibody is chimeric, humanized or fully human.

A "dual-specific antibody", which may for instance be a full-length immunoglobulin or a construct with immunoglobulin like binding properties, is generally understood to have two binding arms, in particular arms defined by a pair of HC/LC, that can bind two different antigens or epitopes in each of its (see PCT publication WO 02/02773). Accordingly a dual-specific binding protein has two identical antigen binding arms, with identical specificity and identical CDR sequences, and is bivalent for each antigen it binds to.

The T cell receptor (TCR) is a particular receptor that is present on the cell surface of T cells, i.e. T lymphocytes. In vivo the T cell receptor exists as a complex of several proteins. The T cell receptor generally has two separate peptide chains, typically T cell receptor alpha and beta (TCRα and TCRβ) chains, on some T cells T cell receptor gamma and delta (TCRγ and TCRδ). The other proteins in the complex are the CD3 proteins: CD3εγ and CD3εδ heterodimers and, most important, a CD3ζ homodimer, which has a total of six ITAM motifs. The ITAM motifs on the CD3ζ can be phosphorylated by Lck and in turn recruit ZAP-70. Lck and/or ZAP-70 can also phosphorylate the tyrosines on many other molecules, not least CD28, LAT and SLP-76, which allows the aggregation of signalling complexes around these proteins.

An antibody molecule according to the invention includes a light chain with a VL domain and a CL domain. The antibody molecule further includes a main chain that includes a VH domain, a CH1 domain and a hinge region. The VH domain is arranged at the N-terminus of the main chain, and the VH domain is linked to the CH1 domain, either directly linked thereto or coupled via a linking peptide of typically 20 or less, including 10 or less amino acid residues. The hinge region is linked to the C-terminal end of the CH1 domain. Accordingly, the portion of the antibody molecule that is defined by the adjacent arrangement of the VL, the CL, the VH and the CH1 domain as well as the hinge region, can be taken to define a Fab fragment and is accordingly referred to also as such herein. As in a naturally occurring immunoglobulin the pairing of the VH and the VL domain together defines a single antigen-binding site. Hence, the Fab fragment of an antibody of the invention includes the binding site for a first antigen. In a respective antibody molecule the light chain is linked to the main chain by a disulfide bond. In some embodiments an antibody molecule according to the invention is a dimer that includes two main chains and two light chains as described above (cf. also below).

In some embodiments the sequence of a recombinant bispecific antibody molecule according to the invention can be compared against the sequence of IgG1, since the sequence of the antibody molecule according to the invention has a certain degree of similarity with the sequence of IgG1, as illustrated further below. In comparison to the amino acid sequence of IgG1 according to Kabat et al. (1991, Sequences of Proteins of Immunological Interest, 5th Ed., United States Public Health Service, National Institutes of Health, Bethesda) a main chain of an antibody molecule according to the invention in some embodiments includes a $V_H$ domain at amino acid positions 1 to 117, a $C_H1$ domain at positions 118 to 215, a hinge region at positions 216 to 230 and a $C_H2$ domain at positions 231 to 340.

In accordance with the amino acid sequence of the main chain of an antibody of the invention the Fab fragment, consisting of the $V_H$ domain, the $C_H1$ domain and the hinge region, in these embodiments typically spans amino acids 1 to 230. Within this Fab fragment the $V_H$ domain is typically defined by amino acids 1 to 118, the $C_H1$ domain is defined by amino acids 119 to 216, and the hinge region is defined by amino acids 217 to 231, according to the Kabat numbering. The antibody chain with the sequence of SEQ ID NO: 6 may serve as an example of a respective embodiment. In some embodiments the antibody molecule according to the invention has, at the positions 342 et sqq of the main chain, a chimeric sequence composed of a $V_H$ domain and a $V_L$ domain. In some embodiments the $V_L$ domain is arranged to define the C-terminal domain of this chimeric sequence. In some embodiments the antibody according to the invention has, in comparison to the amino acid sequence of IgG1 according to Kabat et al., a $C_H3$ domain at positions 342 to 447, followed by a chimeric sequence composed of a $V_H$ domain and a C-terminal $V_L$ domain. In such embodiments where a $C_H3$ domain is included in the antibody according to the invention, this $C_H3$ domain is defined by amino acids 342 to 448 in accordance with the amino acid sequence of the main chain of the antibody molecule. The chimeric sequence composed of a $V_H$ domain and a $V_L$ domain, which may in some embodiments be C-terminal (supra), is in these embodiments located at the positions 449 et sqq of the amino acid sequence of the main chain of the antibody molecule.

A bispecific antibody molecule according to the invention may have two binding sites of any desired specificity. In some embodiments one of the binding sites is capable of binding a tumour associated antigen. In some embodiments the binding site included in the Fab fragment is a binding site specific for a tumour associated surface antigen. In some embodiments the binding site included in the single chain Fv fragment is a binding site specific for a tumour associated antigen such as a tumour associated surface antigen.

The term "tumour associated surface antigen" as used herein refers to an antigen that is or can be presented on a surface that is located on or within tumour cells. These antigens can be presented on the cell surface with an extracellular part, which is often combined with a transmembrane and cytoplasmic part of the molecule. These antigens can in some embodiments be presented only by tumour cells and not by normal, i.e. non-tumour cells. Tumour antigens can be exclusively expressed on tumour cells or may represent a tumour specific mutation compared to non-tumour cells. In such an embodiment a respective antigen may be referred to as a tumour-specific antigen. Some antigens are presented by both tumour cells and non-tumour cells, which may be referred to as tumour-associated antigens. These tumour-associated antigens can be overexpressed on tumour cells when compared to non-tumour cells or are accessible for antibody binding in tumour cells due to the less compact structure of the tumour tissue compared to non-tumour tissue. In some embodiments the tumour associated surface antigen is located on the vasculature of a tumour.

Illustrative examples of a tumor associated surface antigen are CD10, CD19, CD20, CD22, CD33, Fms-like tyrosine kinase 3 (FLT-3, CD135), chondroitin sulfate proteoglycan 4 (CSPG4, melanoma-associated chondroitin sulfate proteoglycan), Epidermal growth factor receptor (EGFR), Her2neu, Her3, IGFR, CD133, IL3R, fibroblast activating protein (FAP), CDCP1, Derlin1, Tenascin, frizzled 1-10, the vascular antigens VEGFR2 (KDR/FLK1), VEGFR3 (FLT4, CD309), PDGFR-α (CD140a), PDGFR-β (CD140b) Endoglin, CLEC14, Tem1-8, and Tie2. Further examples may include A33, CAMPATH-1 (CDw52), Carcinoembryonic antigen (CEA), Carboanhydrase IX (MN/CA IX), CD21, CD25, CD30, CD34, CD37, CD44v6, CD45, CD133, de2-7 EGFR, EGFRvIII, EpCAM, Ep-CAM, Folate-binding protein, G250, Fms-like tyrosine kinase 3 (FLT-3, CD135), c-Kit (CD117), CSF1R (CD115), HLA-DR, IGFR, IL-2 receptor, IL3R, MCSP (Melanoma-associated cell surface chondroitin sulphate proteoglycane), Muc-1, Prostate-specific membrane antigen (PSMA), Prostate stem cell antigen (PSCA), Prostate specific antigen (PSA), and TAG-72. Examples of antigens expressed on the extracellular matrix of tumors are tenascin and the fibroblast activating protein (FAP).

In some embodiments one of the binding sites of an antibody molecule according to the invention is able to bind a T-cell specific receptor molecule and/or a natural killer cell (NK cell) specific receptor molecule. A T-cell specific receptor is the so called "T-cell receptor" (TCRs), which allows a T cell to bind to and, if additional signals are present, to be activated by and respond to an epitope/antigen presented by another cell called the antigen-presenting cell or APC. The T cell receptor is known to resemble a Fab fragment of a naturally occurring immunoglobulin. It is generally monovalent, encompassing α- and β-chains, in some embodiments it encompasses γ-chains and δ-chains (supra). Accordingly, in some embodiments the TCR is TCR (alpha/beta) and in some embodiments it is TCR (gamma/delta). The T cell receptor forms a complex with the CD3 T-Cell co-receptor. CD3 is a protein complex and is composed of four distinct chains. In mammals, the complex contains a CD3γ chain, a CD3δ chain, and two CD3ε chains. These chains associate with a molecule known as the T cell receptor (TCR) and the ζ-chain to generate an activation signal in T lymphocytes. Hence, in some embodiments a T-cell specific receptor is the CD3 T-Cell co-receptor. In some embodiments a T-cell specific receptor is CD28, a protein that is also expressed on T cells. CD28 can provide co-stimulatory signals, which are required for T cell activation. CD28 plays important roles in T-cell proliferation and survival, cytokine production, and T-helper type-2 development. Yet a further example of a T-cell specific receptor is CD134, also termed Ox40. CD134/OX40 is being expressed after 24 to 72 hours following activation and can be taken to define a secondary costimulatory molecule. Another example of a T-cell receptor is 4-1 BB capable of binding to 4-1 BB-Ligand on antigen presenting cells (APCs), whereby a costimulatory signal for the T cell is generated. Another example of a receptor predominantly found on T-cells is CD5, which is also found on B cells at low levels. A further example of a receptor modifying T cell functions is CD95, also known as the Fas receptor, which mediates apoptotic signaling by Fas-ligand expressed on the surface of other cells. CD95 has been reported to modulate TCR/CD3-driven signaling pathways in resting T lymphocytes.

An example of a NK cell specific receptor molecule is CD16, a low affinity Fc receptor and NKG2D. An example of a receptor molecule that is present on the surface of both T cells and natural killer (NK) cells is CD2 and further members of the CD2-superfamily. CD2 is able to act as a co-stimulatory molecule on T and NK cells.

In some embodiments the first binding site of the antibody molecule binds a tumour associated surface antigen and the second binding site binds a T cell specific receptor molecule and/or a natural killer (NK) cell specific receptor molecule. In some embodiments the first binding site of the antibody molecule binds one of A33, CAMPATH-1 (CDw52), Carcinoembryonic antigen (CEA), Carboanhydrase IX (MN/CA IX), CD10, CD19, CD20, CD21, CD22, CD25, CD30, CD33, CD34, CD37, CD44v6, CD45, CD133, CDCP1, Her3, chondroitin sulfate proteoglycan 4 (CSPG4, melanoma-associated chondroitin sulfate proteoglycan), CLEC14, Derlin1, Epidermal growth factor receptor (EGFR), de2-7 EGFR, EGFRvIII, EpCAM, Endoglin, Ep-CAM, Fibroblast activation protein (FAP), Folate-binding protein, G250, Fms-like tyrosine kinase 3 (FLT-3, CD135), c-Kit (CD117), CSF1R (CD115), frizzled 1-10, Her2/neu, HLA-DR, IGFR, IL-2 receptor, IL3R, MCSP (Melanoma-associated cell surface chondroitin sulphate proteoglycane), Muc-1, Prostate-specific membrane antigen (PSMA), Prostate stem cell antigen (PSCA), Prostate specific antigen (PSA), TAG-72, Tenascin, Tem1-8, Tie2 and VEGFR2 (KDR/FLK1), VEGFR3 (FLT4, CD309), PDGFR-α (CD140a), PDGFR-β (CD140b), and the second binding site binds a T cell specific receptor molecule and/or a natural killer (NK) cell specific receptor molecule. In some embodiments the first binding site of the antibody molecule binds a tumour associated surface antigen and the second binding site binds one of CD3, the T cell receptor (TCR), CD28, CD16, NKG2D, Ox40, 4-1BB, CD2, CD5 and CD95.

In some embodiments the first binding site of the antibody molecule binds a T cell specific receptor molecule and/or a natural killer (NK) cell specific receptor molecule and the second binding site binds a tumour associated surface antigen. In some embodiments the first binding site of the antibody binds a T cell specific receptor molecule and/or a natural killer (NK) cell specific receptor molecule and the second binding site binds one of A33, CAMPATH-1 (CDw52), Carcinoembryonic antigen (CEA), Carboanhydrase IX (MN/CA IX), CD10, CD19, CD20, CD21, CD22, CD25, CD30, CD33, CD34, CD37, CD44v6, CD45, CD133, CDCP1, Her3, chondroitin sulfate proteoglycan 4 (CSPG4, melanoma-associated chondroitin sulfate proteoglycan), CLEC14, Derlin1, Epidermal growth factor receptor (EGFR), de2-7 EGFR, EGFRvIII, EpCAM, Endoglin, Ep-CAM, Fibroblast activation protein (FAP), Folate-binding protein, G250, Fms-like tyrosine kinase 3 (FLT-3, CD135), frizzled 1-10, Her2/neu, HLA-DR, IGFR, IL-2 receptor, IL3R, MCSP (Melanoma-associated cell surface chondroitin sulphate proteoglycane), Muc-1, Prostate-specific membrane antigen (PSMA), Prostate specific antigen (PSA), TAG-72, Tenascin, Tem1-8, Tie2 and VEGFR. In some embodiments the first binding site of the antibody binds one of CD3, the T cell receptor (TCR), CD28, CD16, NKG2D, Ox40, 4-1BB, CD2, CD5 and CD95, and the second binding site binds a tumour associated surface antigen.

The term "glycosylation" means the attachment of oligosaccharides (carbohydrates containing two or more simple sugars linked together e.g. from two to about twelve simple sugars linked together) to a glycoprotein. The oligosaccharide side chains are typically linked to the backbone of the glycoprotein through either N- or O-linkages. The oligosaccharides of antibodies disclosed herein occur generally are attached to a CH2 domain of an Fc region as N-linked oligosaccharides. "N-linked glycosylation" refers to the attachment of the carbohydrate moiety to an asparagine residue in a glycoprotein chain. The skilled artisan will recognize that, for example, each of murine IgG1, IgG2a, IgG2b and IgG3 as well as human IgG1, IgG2, IgG3, IgG4, IgA and IgD CH2 domains have a single site for N-linked glycosylation at residue 297.

Sequences of domains or regions included in an antibody molecule according to the invention may be sequences of any desired species. Depending on the subsequent use of the antibody molecule it may, nevertheless, be desirable in some embodiments, to introduce alterations that prevent undesired side effects caused by the antibody. The use of intact non-human antibodies in the treatment of human diseases or disorders carries with it the potential for the now well established problems of immunogenicity, which means that the immune system of the patient may recognise the non-human intact antibody as non-self and mount a neutralising response. This is particularly evident upon multiple administration of the non-human antibody to a human patient. Various techniques have been developed over the years to overcome these problems and generally involve reducing the composition of non-human amino acid sequences in the intact antibody whilst retaining the relative ease in obtaining non-human antibodies from an immunised animal e.g. mouse, rat or rabbit. Broadly two approaches have been used to achieve this. The first are chimeric antibodies, which generally have a non-human (e.g. rodent such as mouse) variable domain fused to a human constant region. Because the antigen-binding site of an antibody is defined by residues within the variable domains the chimeric antibody retains its binding affinity for the antigen but acquires the effector functions of the human constant region and are therefore able to perform effector functions such as described supra. Chimeric antibodies are typically produced using recombinant DNA methods. DNA encoding the antibodies (e.g. cDNA) is isolated and sequenced using conventional procedures (e.g. by using oligonucleotide probes that are capable of binding specifically to genes encoding the H and L chains of the antibody of the invention. Hybridoma cells serve as a typical source of such DNA. Once isolated, the DNA is placed into expression vectors which are then transfected into host cells such as E. coli, COS cells, CHO cells or myeloma cells that do not otherwise produce immunoglobulin protein to obtain synthesis of the antibody. The DNA may be modified by substituting the coding sequence for human L and H chains for the corresponding non-human, e.g. murine, H and L constant regions (see e.g. Morrison; PNAS [1984] 81, 6851).

The second approach involves the generation of humanised antibodies wherein the non-human content of the antibody is reduced by humanizing the variable domains. Two techniques for humanisation have gained popularity. The first is humanisation by CDR grafting. CDRs define loops (supra) and antigen-binding specificity of an antibody is mainly defined by the topography and by the chemical characteristics of its CDR surface. These features are in turn determined by the conformation of the individual CDRs, by the relative disposition of the CDRs, and by the nature and disposition of the side chains of the residues including the CDRs. A large decrease in immunogenicity can be achieved by grafting only the CDRs of a non-human, e.g. murine, antibodies ("donor" antibodies) onto human framework ("acceptor framework") and constant regions (see Jones et al (1986) Nature 321, 522-525 and Verhoeyen M et al (1988) Science 239, 1534-1536). However, CDR grafting per se may not result in the complete retention of antigen-binding properties and it is frequently found that some framework residues (sometimes referred to as "back mutations") of the donor antibody need to be preserved in the humanised molecule if significant antigen-binding affinity is to be recovered (see Queen C et al (1989) PNAS 86, 10,029-10, 033, Co, M et al (1991) Nature 351, 501-502). In this case, human variable domains showing the greatest sequence homology to the non-human donor antibody are chosen from a database in order to provide the human framework (FR). The selection of human FRs can be made either from human consensus or individual human antibodies. Where necessary key residues from the donor antibody are substituted into the human acceptor framework to preserve CDR conformations, computer modelling of the antibody may be used to help identify such structurally important residues. See WO99/48523, for example.

Alternatively, humanisation maybe achieved by a process of "veneering". A statistical analysis of unique human and murine immunoglobulin heavy and light chain variable domains revealed that the precise patterns of exposed residues are different in human and murine antibodies, and most individual surface positions have a strong preference for a small number of different residues (see Padlan E. A. et al; (1991) Mol. Immunol. 28, 489-498 and Pedersen J. T. et al (1994) J. Mol. Biol. 235; 959-973). Therefore it is possible to reduce the immunogenicity of a non-human Fv by replacing exposed residues in its framework regions that differ from those usually found in human antibodies. Because protein antigenicity may be correlated with surface accessibility, replacement of the surface residues may be sufficient to render the mouse variable domain "invisible" to the human immune system (see also Mark G. E. et al (1994) in Handbook of Experimental Pharmacology vol. 113: The pharmacology of monoclonal Antibodies, Springer-Verlag, pp 105-134). This procedure of humanisation is referred to as "veneering" because only the surface of the antibody is altered, the supporting residues remain undisturbed.

An antibody molecule of the invention may be produced using any known and well-established expression system and recombinant cell culturing technology, for example, by expression in bacterial hosts (prokaryotic systems), or eukaryotic systems such as yeasts, fungi, insect cells or mammalian cells. An antibody molecule of the present invention may be produced in transgenic organisms such as a goat, a plant or a XENOMOUSE transgenic mouse, an engineered mouse strain that has large fragments of the human immunoglobulin loci and is deficient in mouse antibody production. An antibody may also be produced by chemical synthesis.

For recombinant production of an antibody molecule of the invention typically a polynucleotide encoding the antibody is isolated and inserted into a replicable vector such as a plasmid for further cloning (amplification) or expression. An illustrative example of a suitable expression system is a glutamate synthetase system (such as sold by Lonza Biologics), with the host cell being for instance CHO or NS0. A polynucleotide encoding the antibody is readily isolated and sequenced using conventional procedures. Vectors that may be used include plasmid, virus, phage, transposons, minichromsomes of which plasmids are a typical embodiment. Generally such vectors further include a signal sequence, origin of replication, one or more marker genes, an enhancer element, a promoter and transcription termination sequences operably linked to the light and/or heavy chain polynucleotide so as to facilitate expression. Polynucleotides encoding the light and heavy chains may be inserted into separate vectors and transfected into the same host cell or, if desired both the heavy chain and light chain can be inserted into the same vector for transfection into the host cell. Both chains can, for example, be arranged, under the control of a dicistronic operon and expressed to result in the functional and correctly folded antibody molecule as described in Skerra, A. (1994) Use of the tetracycline promoter for the tightly regulated production of a murine antibody fragment in *Escherichia coli*, Gene 151, 131-135, or Skerra, A. (1994) A general vector, pASK84, for cloning, bacterial production, and single-step purification of antibody Fab fragments, Gene 141, 79-8. Thus according to one aspect of the present invention there is provided a process of constructing a vector encoding the light and/or heavy chains of an antibody or antigen binding fragment thereof of the invention, which method includes inserting into a vector, a polynucleotide encoding either a light chain and/or heavy chain of an antibody molecule of the invention.

When using recombinant techniques, the antibody molecule can be produced intracellularly, in the periplasmic space, or directly secreted into the medium (cf. also Skerra 1994, supra). If the antibody is produced intracellularly, as a first step, the particulate debris, either host cells or lysed fragments, are removed, for example, by centrifugation or ultrafiltration. Carter et al., Bio/Technology 10: 163-167 (1992) describe a procedure for isolating antibodies which are secreted to the periplasmic space of *E coli*. The antibody can also be produced in any oxidizing environment. Such an oxidizing environment may be provided by the periplasm of Gram-negative bacteria such as *E. coli*, in the extracellular milieu of Gram-positive bacteria or in the lumen of the endoplasmatic reticulum of eukaryotic cells (including animal cells such as insect or mammalian cells) and usually favors the formation of structural disulfide bonds. It is, however, also possible to produce an antibody molecule of the invention in the cytosol of a host cell such as *E. coli*. In this case, the polypeptide can either be directly obtained in a soluble and folded state or recovered in form of inclusion bodies, followed by renaturation in vitro. A further option is the use of specific host strains having an oxidizing intracellular milieu, which may thus allow the formation of disulfide bonds in the cytosol (Venturi M, Seifert C, Hunte C. (2002) "High level production of functional antibody Fab fragments in an oxidizing bacterial cytoplasm." J. Mol. Biol. 315, 1-8).

The antibody molecule produced by the cells can be purified using any conventional purification technology, for example, hydroxylapatite chromatography, gel electrophoresis, dialysis, and affinity chromatography, with affinity chromatography being one preferred purification technique.

Antibody molecules may be purified via affinity purification with proteins/ligands that specifically and reversibly bind constant domains such as the CH1 or the CL domains. Examples of such proteins are immunoglobulin-binding bacterial proteins such as Protein A, Protein G, Protein NG or Protein L, wherein Protein L binding is restricted to antibody molecules that contain kappa light chains. An alternative method for purification of antibodies with K-light chains is the use of bead coupled anti kappa antibodies (KappaSelect). The suitability of protein A as an affinity ligand depends on the species and isotype of any immunoglobulin Fc domain that is present in the antibody. Protein A can be used to purify antibodies (Lindmark et al., J. Immunol. Meth. 62: 1-13 (1983)). Protein G is recommended for all mouse isotypes and for human gamma3 (Guss et al., EMBO J. 5: 15671575 (1986)). The choice of the purification method that is used for a particular antibody molecule of the invention is within the knowledge of the person of average skill in the art.

It is also possible to equip one of the chains of the antibody molecule of the invention with an affinity tag. Affinity tags such as the Strep-Tag® or Strep-Tag® II (Schmidt, T. G. M. et al. (1996) J. Mol. Biol. 255, 753-766), the myc-tag, the FLAG™-tag, the His6-tag or the HA-tag allow easy detection and also simple purification of the recombinant antibody molecule.

The terms "mutated", "mutant" and "mutation" in reference to a nucleic acid or a polypeptide refers to the exchange, deletion, or insertion of one or more nucleotides or amino acids, respectively, compared to the naturally occurring nucleic acid or polypeptide, i.e. to a reference sequence that can be taken to define the wild-type.

It is understood in this regard that the term "position", when used in accordance with the present invention, means the position of an amino acid within an amino acid sequence depicted herein. This position may be indicated relative to a resembling native sequence, e.g. a sequence of a naturally occurring IgG domain or chain. The term "corresponding" as used herein also includes that a position is not necessarily, or not only, determined by the number of the preceding nucleotides/amino acids. Thus, the position of a given amino acid in accordance with the present invention which may be substituted may vary due to deletion or addition of amino acids elsewhere in the antibody chain.

Thus, under a "corresponding position" in accordance with the present invention it is to be understood that amino acids may differ in the indicated number but may still have similar neighbouring amino acids. Said amino acids which may be exchanged, deleted or added are also encompassed by the term "corresponding position". In order to determine whether an amino acid residue in a given amino acid sequence corresponds to a certain position in the amino acid sequence of a naturally occurring immunoglobuline domain or chain, the skilled person can use means and methods well-known in the art, e.g., alignments, either manually or by using computer programs such as BLAST2.0, which stands for Basic Local Alignment Search Tool or ClustalW or any other suitable program which is suitable to generate sequence alignments.

In some embodiments a substitution (or replacement) is a conservative substitution. Conservative substitutions are generally the following substitutions, listed according to the amino acid to be mutated, each followed by one or more replacement(s) that can be taken to be conservative: Ala→Gly, Ser, Val; Arg→Lys; Asn→Gln, His; Asp→Glu; Cys→Ser; Gln→Asn; Glu→Asp; Gly→Ala; His→Arg, Asn, Gln; Ile→Leu, Val; Leu→Ile, Val; Lys→Arg, Gln, Glu;

Met→Leu, Tyr, Ile; Phe→Met, Leu, Tyr; Ser→Thr; Thr→Ser; Trp→Tyr; Tyr→Trp, Phe; Val→Ile, Leu. Other substitutions are also permissible and can be determined empirically or in accord with other known conservative or non-conservative substitutions. As a further orientation, the following eight groups each contain amino acids that can typically be taken to define conservative substitutions for one another:

1) Alanine (Ala), Glycine (Gly);
2) Aspartic acid (Asp), Glutamic acid (Glu);
3) Asparagine (Asn), Glutamine (Gln);
4) Arginine (Arg), Lysine (Lys);
5) Isoleucine (Ile), Leucine (Leu), Methionine (Met), Valine (Val);
6) Phenylalanine (Phe), Tyrosine (Tyr), Tryptophan (Trp);
7) Serine (Ser), Threonine (Thr); and
8) Cysteine (Cys), Methionine (Met)

If such substitutions result in a change in biological activity, then more substantial changes, such as the following, or as further described below in reference to amino acid classes, may be introduced and the products screened for a desired characteristic. Examples of such more substantial changes are: Ala→Leu, Ile; Arg→Gln; Asn→Asp, Lys, Arg, His; Asp→Asn; Cys→Ala; Gln→Glu; Glu→Gln; His→Lys; Ile→Met, Ala, Phe; Leu→Ala, Met, Norleucine; Lys→Asn; Met→Phe; Phe→Val, Ile, Ala; Trp→Phe; Tyr→Thr, Ser; Val→Met, Phe, Ala.

In some embodiments an antibody molecule according to the invention includes one or more amino acid residues, including two, three, four, five, six, seven, eight, nine, ten, eleven, twelve, thirteen, fourteen, fifteen, sixteen, seventeen or eighteen amino acid residues, that are mutated to prevent dimerization via cystein residues or to modulate Fc-function. In some of these embodiments one or more amino acid residue(s) of the CH2 domain and/or of the hinge region that is able to mediate binding to Fc receptors are mutated. If present, the one or more amino acid residue(s) able to mediate binding to Fc receptors may be an amino acid residue that is able to activate antibody dependent cellular cytotoxicity (ADCC) or complement-mediated cytotoxicity (CDC). In some embodiments a respective amino acid residue capable of mediating binding to Fc receptors is substituted by another amino acid, generally when comparing the sequence to the sequence of a corresponding naturally occurring domain in an immunoglobulin, such as an IgG. In some embodiments such an amino acid residue capable of mediating binding to Fc receptors is deleted, generally relative to the sequence of a corresponding naturally occurring domain in an immunoglobulin, such as an IgG. However, in other embodiments of the invention that relate to a bispecific antibody molecule consisting of a Fab fragment, a single chain Fv fragment and an immunoglobulin CH2 domain, it is within the scope of the invention to introduce mutations in the CH2 domain of human γ1, for example, that optimize antibody dependent cytotoxicity (ADCC). Such mutations are described in the international patent applications WO2011/076922 and WO2011/089211, for example.

In some embodiments the one or more mutated, e.g. substituted or deleted, amino acid residues is/are an amino acid located at one of the positions 226, 228, 229, 230, 231, 232, 233, 234, 235, 236, 237, 238, 265, 297, 327, and 330. Again, the numbering of amino acids used corresponds to the sequence positions according to the Kabat numbering [EU-Index]. A corresponding deletion of an amino acid may for example be a deletion of amino acid 228, generally a proline in IgG, a deletion of amino acid 229, generally a cysteine in IgG, a deletion of amino acid 230, generally a proline in IgG, a deletion of amino acid 231, generally an alanine in IgG, a deletion of amino acid 232, generally a proline in IgG, a deletion of amino acid 233, generally a glutamic acid in IgG, a deletion of amino acid 234, generally a leucine in IgG, a deletion of amino acid 235, generally a leucine in IgG, a deletion of amino acid 236, generally a glycine in IgG, a deletion of amino acid 237, generally a glycine in IgG, a deletion of amino acid 238, generally a proline in IgG and a deletion of amino acid 265, generally an aspartic acid in IgG. A corresponding substitution of an amino acid may for example be a substitution of amino acid 226, generally a cysteine in IgG, a substitution of amino acid 228, generally a proline in IgG, a substitution of amino acid 229, generally a cysteine in IgG, a substitution of amino acid 230, generally a proline in IgG, a substitution of amino acid 231, generally an alanine in IgG, a substitution of amino acid 232, generally a proline in IgG, a substitution of amino acid 233, generally a glutamic acid in IgG, a substitution of amino acid 234, generally a leucine in IgG, a substitution of amino acid 235, generally a leucine in IgG, a substitution of amino acid 265, generally an aspartic acid in IgG, a substitution of amino acid 297, generally an asparagine in IgG, a substitution of amino acid 327, generally an alanine in IgG, and a substitution of amino acid 330, generally an alanine in IgG. A respective substitution may be one of substitution Cys226→Ser, substitution Cys229→Ser, substitution Glu233→Pro, substitution Leu234→Val, substitution Leu235→Ala, substitution Asp265→Gly, substitution Asn297→Gln, substitution Ala327→Gln, substitution Ala327→Gly, and substitution Ala330→Ser. As can be taken from the above, in some embodiments one or two of the cysteine residues at positions 226 and 229 in the hinge region are being substituted for another amino acid, for instance substituted for a serine residue. Thereby the formation of a disulphide bond with another main chain can be prevented. Further, and as also explained below, deleting and/or substituting (mutating) selected amino acid residues in the CH2 domain that is able to mediate binding to Fc-receptors can cause an antibody molecule of the invention to have less or no activity in terms of antibody-dependent cell-mediated cytotoxicity and fixation of complement.

Another type of amino acid variant of an antibody alters the original glycosylation pattern (if any) of the antibody molecule. By altering is meant deleting one or more carbohydrate moieties found in the antibody, and/or adding one or more glycosylation sites that are not present in the antibody. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

In the context of the present invention in some embodiments the portion of the main chain of the antibody molecule of the invention, which represents the Fc region of an immunoglobulin, is typically inert, or at least essentially of low influence, with regard to binding to Fc receptors. As said, this is achieved by deleting and/or substituting (mutating) at least one of selected amino acid residues in the CH2 domain that are able to mediate binding to an Fc-receptor. Such molecules are also referred to herein as "Fc-attenuated" antibody molecules or "Fc$^{ko}$" antibody molecules. The portion of an antibody chain according to the invention that can be taken to represent a portion of an Fc fragment, i.e. the CH2 domain, and, where present, the CH3 domain, thus might define a "scaffold" without providing a particular biological function such as an effector function, for example. However, it has been found in the present invention, that this scaffold may provide significant advantages in terms of purification, production efficiency and/or stability of the antibody molecules of the invention compared to known antibody molecules (cf. the Examples).

In some embodiments the recognition, and accordingly binding, of this Fc-corresponding portion to a given Fc receptor is of about 2-fold, about 5-fold, about 8-fold, about 10-fold, about 12-fold, about 15-fold, about 20-fold or lower than the Fc region of a naturally occurring immunoglobulin. In some embodiments this Fc-corresponding portion is entirely void of its ability of binding to Fc receptors. The binding of an antibody to Fc receptors, including determining a dissociation constant, can easily be determined by the skilled artisan using standard techniques such as surface plasmon resonance, e.g. using a Biacore™ measurement. Any other method of measuring biomolecular binding may likewise be used, which may for instance rely on spectroscopical, photochemical, photometric or radiological means. Examples for the corresponding detection methods are fluorescence correlation spectroscopy, photochemical cross-linking and the use of photoactive or radioactive labels respectively. Some of these methods may include additional separation techniques such as electrophoresis or HPLC.

Where required, a substitution or deletion of amino acid residues, as explained above, may be carried out to this effect. Suitable mutations can be taken from Armour et al. (Eur. J. Immunol. [1999] 29, 2613-2624), for example. Further suitable positions for mutations to a sequence of an antibody chain can be taken from the crystal structure data published on the complex between FcγRIII and the human IgG1 Fc fragment (Sondermann et al., Nature [2000] 406, 267-273). In addition to measuring the binding affinity as described above in order to assess the level of "Fc attenuation" or loss of binding affinity, it is also possible to functionally assess the (lack of the) ability to mediate binding to an Fc-receptor. In the case of antibody molecules which bind CD3 as one target, it is for example possible to assess the binding through the mitogenity of such CD3 binding antibody molecules on cells. The mitogenity is mediated by binding of CD3 antibodies to the Fc-receptors on accessory cells, such as monocytes. If an antibody molecule of the invention that has one binding site for CD3 does not show any mitogenic effect whereas the parent monoclonal anti-CD3 antibody that has a functional Fc part induces strong mitosis in T cells, it is clear that, due to the lack of mitosis, the antibody molecule of the invention lacks the ability for Fc binding and can thus be considered as a "Fc knock-out" molecule. Illustrative examples of a method of assessing anti-CD3 mediated mitogenity have been described by Davis, Vida & Lipsky (J. Immunol (1986) 137, 3758), and by Ceuppens, J L, & van Vaeck, F, (see J. Immunol. (1987) 139, 4067, or Cell. Immunol. (1989) 118, 136). Further illustrative suitable examples of an assay for assessing mitogenity of an antibody have been described by Rosenthal-Allieri et al. (Rosenthal-Allieri M A, Ticcioni M, Deckert M, Breittmeyer J P, Rochet N, Rouleaux M, and Senik A, Bernerd A, Cell Immunol. 1995 163(1):88-95) and Grosse-Hovest et al. (Grosse-Hovest L, Hartlapp I, Marwan W, Brem G, Rammensee H-G, and Jung G, Eur J Immunol. [2003] May; 33(5):1334-1340). In addition, the lack of Fc binding can be assessed by the ability of an antibody molecule of the invention to mediate one or more of the well-known effector functions of the Fc part.

As noted above, substitutions or deletions of cysteine residues may be carried out in order to introduce or to remove one or more disulphide bonds, including introducing or removing a potential or a previously existing disulphide bond. Thereby linkage between a main chain and a chain of lower weight/shorter length of an antibody molecule according to the invention may be controlled including established, strengthened or abolished. By introducing or removing one or more cysteine residues a disulphide bridge may be introduced or removed. As an illustrative example, a tetrameric antibody molecule according to the invention generally has one or more disulphide bonds that link two dimeric antibody molecules. One such disulphide bond is typically defined by a cysteine in the main chain of a first dimeric antibody molecule and a cysteine in the hinge region of a second dimeric antibody molecule. In this regard, in some embodiments an antibody according to the invention may include an amino acid substitution of a native cysteine residue at positions 226 and/or 229, relative to the sequence of a human IgG immunoglobulin according to the Kabat numbering [EU-Index], by another amino acid residue.

Substitutions or deletions of amino acid residues such as arginine, asparagine, serine, threonine or tyrosine residues may also be carried out to modify the glycosylation pattern of an antibody. As an illustrative example, an IgG molecule has a single N-linked biantennary carbohydrate at Asn297 of the CH2 domain. For IgG from either serum or produced ex vivo in hybridomas or engineered cells, the IgG are heterogeneous with respect to the Asn297 linked carbohydrate. For human IgG, the core oligosaccharide typically consists of GlcNAc$_2$Man$_3$GlcNAc, with differing numbers of outer residues.

As indicated, besides binding of antigens/epitopes, an immunoglobulin is known to have further "effector functions", biological activities attributable to the Fc region (a native sequence Fc region or amino acid sequence variant Fc region) of an immunoglobulin, and vary with the immunoglobulin isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g., B cell receptors); and B cell activation. Exerting effector functions of an antibody generally involves recruiting effector cells. Several immunoglobulin effector functions are mediated by Fc receptors (FcRs), which bind the Fc region of an antibody. FcRs are defined by their specificity for immunoglobulin isotypes; Fc receptors for IgG antibodies are referred to as FcγR, for IgE as FcεR, for IgA as FcαR and so on. Any of these effector functions (or the loss of such effector functions) such a CDC or ADCC can be used in order to evaluate whether an antibody molecule of the invention lacks the ability of Fc binding.

In this context, it is noted that the term "Fc receptor" or "FcR" defines a receptor, generally a protein that is capable of binding to the Fc region of an antibody. Fc receptors are found on the surface of certain cells of the immune system of an organism, for example natural killer cells, macrophages, neutrophils, and mast cells. In vivo Fc receptors bind to immunoglobulins that are immobilized on infected cells or present on invading pathogens. Their activity stimulates phagocytic or cytotoxic cells to destroy microbes, or infected cells by antibody-mediated phagocytosis or antibody-dependent cell-mediated cytotoxicity. Some viruses such as flaviviruses use Fc receptors to help them infect cells, by a mechanism known as antibody-dependent enhancement of infection. FcRs have been reviewed in Ravetch and Kinet, Annu. Rev. Immunol. 9: 457-92 (1991); Capel et al., Immunomethods 4: 25-34 (1994); and de Haas et al., J. Lab. Clin. Med. 126: 330-41 (1995).

"Complement dependent cytotoxicity" or "CDC" refers to the lysis of a target cell in the presence of complement. Activation of the classical complement pathway is initiated by the binding of the first component of the complement system (Clq) to antibodies (of the appropriate subclass) which are bound to their cognate antigen. To assess complement activation, a CDC assay, e.g., as described in Gazzano-Santoro et al., J. Immunol. Methods 202: 163 (1997) may be performed.

The term "complement system" is used in the art to refer a number of small proteins—called complement factors—found in blood, generally circulating as inactive precursors (pro-proteins). The term refers to the ability of this inalterable and not adaptable system to "complement" the capability of antibodies and phagocytic cells to clear pathogens such as bacteria, as well as antigen-antibody complexes, from an organism. An example of complement factors is the complex C1, which includes C1q and two serine protases, C1r and C1 s. The complex C1 is a component of the CDC pathway. C1q is a hexavalent molecule with a molecular weight of approximately 460,000 and a structure likened to a bouquet of tulips in which six collagenous "stalks" are connected to six globular head regions. To activate the complement cascade, C1q has to bind to at least two molecules of IgG1, IgG2 or IgG3.

"Antibody-dependent cell-mediated cytotoxicity" or ADCC refers to a form of cytotoxicity in which secreted Ig bound onto Fc receptors (FcRs) present on certain cytotoxic cells—such as natural killer (NK) cells, neutrophils and macrophages—enable these cytotoxic effector cells to bind specifically to an antigen-bearing target cell and subsequently kill the target cell with cytotoxins. The antibodies "arm" the cytotoxic cells and are required for killing of the target cell by this mechanism. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol. 9: 457-92 (1991). To assess ADCC activity of a molecule of interest, an in vitro ADCC assay, such as described in U.S. Pat. Nos. 5,500,362 or 5,821,337 may be carried out. Useful effector cells for such assays include, but are not limited to, peripheral blood mononuclear cells (PBMC) and natural killer (NK) cells. In some embodiments ADCC activity of the molecule of interest may be assessed in vivo, e.g., in an animal model such as disclosed in Clynes et al., PNAS USA 95: 652-656 (1998).

Several antibody effector functions are mediated by Fc receptors (FcRs), which bind the Fc region of an antibody. FcRs are defined by their specificity for immunoglobulin isotypes; Fc receptors for IgG antibodies are referred to as FcγR, for IgE as FcεR, for IgA as FcαR and so on. Three subclasses of FcγR have been identified: FcγRI (CD64), FcγRII (CD32) and FcγRIII (CD16).

Turning now to nucleic acids of the invention, a nucleic acid molecule encoding one or more chains of an antibody according to the invention may be any nucleic acid in any possible configuration, such as single stranded, double stranded or a combination thereof. Nucleic acids include for instance DNA molecules, RNA molecules, analogues of the DNA or RNA generated using nucleotide analogues or using nucleic acid chemistry, locked nucleic acid molecules (LNA), and protein nucleic acids molecules (PNA). DNA or RNA may be of genomic or synthetic origin and may be single or double stranded. Such nucleic acid can be e.g. mRNA, cRNA, synthetic RNA, genomic DNA, cDNA synthetic DNA, a copolymer of DNA and RNA, oligonucleotides, etc. A respective nucleic acid may furthermore contain non-natural nucleotide analogues and/or be linked to an affinity tag or a label.

In some embodiments a nucleic acid sequence encoding a chain, such as a main chain and/or a smaller chain of an antibody according to the invention is included in a vector such as a plasmid. Where a substitution or deletion is to be included in an antibody chain, when compared to a naturally occurring domain or region of an antibody, the coding sequence of the respective native domain/region, e.g. included in the sequence of an immunoglobulin, can be used as a starting point for the mutagenesis. For the mutagenesis of selected amino acid positions, the person skilled in the art has at his disposal the various established standard methods for site-directed mutagenesis. A commonly used technique is the introduction of mutations by means of PCR (polymerase chain reaction) using mixtures of synthetic oligonucleotides, which bear a degenerate base composition at the desired sequence positions. For example, use of the codon NNK or NNS (wherein N=adenine, guanine or cytosine or thymine; K=guanine or thymine; S=adenine or cytosine) allows incorporation of all 20 amino acids plus the amber stop codon during mutagenesis, whereas the codon WS limits the number of possibly incorporated amino acids to 12, since it excludes the amino acids Cys, Ile, Leu, Met, Phe, Trp, Tyr, Val from being incorporated into the selected position of the polypeptide sequence; use of the codon NMS (wherein M=adenine or cytosine), for example, restricts the number of possible amino acids to 11 at a selected sequence position since it excludes the amino acids Arg, Cys, Gly, Ile, Leu, Met, Phe, Trp, Val from being incorporated at a selected sequence position. In this respect it is noted that codons for other amino acids (than the regular 20 naturally occurring amino acids) such as selenocystein or pyrrolysine can also be incorporated into a nucleic acid of a antibody molecule. It is also possible, as described by Wang, L., et al. (2001) Science 292, 498-500, or Wang, L., and Schultz, P. G. (2002) Chem. Comm. 1, 1-11, to use "artificial" codons such as UAG which are usually recognized as stop codons in order to insert other unusual amino acids, for example o-methyl-L-tyrosine or p-aminophenylalanine.

The use of nucleotide building blocks with reduced base pair specificity, as for example inosine, 8-oxo-2'deoxyguanosine or 6(2-deoxy-β-D-ribofuranosyl)-3,4-dihydro-8H-pyrimin-do-1,2-oxazine-7-one (Zaccolo et al. (1996) J. Mol. Biol. 255, 589-603), is another option for the introduction of mutations into a chosen sequence segment. A further possibility is the so-called triplet-mutagenesis. This method uses mixtures of different nucleotide triplets, each of which codes for one amino acid, for incorporation into the coding sequence (Virnekas B, et al., 1994 Nucleic Acids Res 22, 5600-5607).

A nucleic acid molecule encoding a chain, such as a main chain and/or a smaller chain of an antibody according to the invention can be expressed using any suitable expression system, for example in a suitable host cell or in a cell-free system. The obtained antibody molecule is enriched by means of selection and/or isolation.

As explained above, an antibody molecule according to the invention may be directed against any desired target epitopes/antigens. Depending on the selected epitopes/antigens the antibody may be suitable in the treatment or prevention of disease. Accordingly, in some embodiments an antibody according to the invention may be used in a method of treating and/or preventing a medical condition such as a disorder or disease. In embodiments where one of the antibodies incorporated in a bispecific molecule is capable of activating immune cells in an FcR-dependent manner it may be particularly useful to select an antibody molecule that has an Fc-corresponding portion that shows reduced binding to Fc-receptors. By this means an undesired immune activation mediated by FcR binding is prevented. In some embodiments a disease to be treated or prevented may be a proliferatory disease. Examples of a proliferative disease include, but are not limited to, hemopoetic malignancies, such as acute and chronic myeloic and lymphatic leukemias, as well as lymphomas, or solid tumors. Examples of solid tumors include, but are not limited to, tumors of the gastrointestinal tract, bone, lung, kidney, prostate, breast, brain, ovary, uterus, testis, mesenchymal tumors and skin, such as melanoma.

The invention also provides a pharmaceutical composition that includes an antibody molecule of the invention and, optionally a pharmaceutically acceptable excipient.

The antibody molecule according to the invention can be administered via any parenteral or non-parenteral (enteral) route that is therapeutically effective for proteinaceous drugs. Parenteral application methods include, for example, intracutaneous, subcutaneous, intramuscular, intratracheal, intranasal, intravitreal or intravenous injection and infusion techniques, e.g. in the form of injection solutions, infusion solutions or tinctures, as well as aerosol installation and inhalation, e.g. in the form of aerosol mixtures, sprays or powders. An overview about pulmonary drug delivery, i.e. either via inhalation of aerosols (which can also be used in intranasal administration) or intracheal instillation is given by J. S. Patton et al. The lungs as a portal of entry for systemic drug delivery. Proc. Amer. Thoracic Soc. 2004 Vol. 1 pages 338-344, for example). Non-parenteral delivery modes are, for instance, orally, e.g. in the form of pills, tablets, capsules, solutions or suspensions, or rectally, e.g. in the form of suppositories. Antibody molecules of the invention can be administered systemically or topically in formulations containing conventional non-toxic pharmaceutically acceptable excipients or carriers, additives and vehicles as desired.

In one embodiment of the present invention the pharmaceutical is administered parenterally to a mammal, and in particular to humans. Corresponding administration methods include, but are not limited to, for example, intracutaneous, subcutaneous, intramuscular, intratracheal or intravenous injection and infusion techniques, e.g. in the form of injection solutions, infusion solutions or tinctures as well as aerosol installation and inhalation, e.g. in the form of aerosol mixtures, sprays or powders. A combination of intravenous and subcutaneous infusion and/or injection might be most convenient in case of compounds with a relatively short serum half life. The pharmaceutical composition may be an aqueous solution, an oil-in water emulsion or a water-in-oil emulsion.

In this regard it is noted that transdermal delivery technologies, e.g. iontophoresis, sonophoresis or microneedle-enhanced delivery, as described in Meidan V M and Michniak B B 2004 Am. J. Ther. 11(4): 312-316, can also be used for transdermal delivery of an antibody molecule described herein. Non-parenteral delivery modes are, for instance, oral, e.g. in the form of pills, tablets, capsules, solutions or suspensions, or rectal administration, e.g. in the form of suppositories. The antibody molecules of the invention can be administered systemically or topically in formulations containing a variety of conventional non-toxic pharmaceutically acceptable excipients or carriers, additives, and vehicles.

The dosage of the antibody molecule applied may vary within wide limits to achieve the desired preventive effect or therapeutic response. It will, for instance, depend on the affinity of the antibody molecule for a chosen target as well as on the half-life of the complex between the antibody molecule and the ligand in vivo. Further, the optimal dosage will depend on the biodistribution of the antibody molecule or a conjugate thereof, the mode of administration, the severity of the disease/disorder being treated as well as the medical condition of the patient. For example, when used in an ointment for topical applications, a high concentration of the antibody molecule can be used. However, if wanted, the antibody molecule may also be given in a sustained release formulation, for example liposomal dispersions or hydrogel-based polymer microspheres, like PolyActive™ or OctoDEX™ (cf. Bos et al., Business Briefing: Pharmatech 2003: 1-6). Other sustained release formulations available are for example PLGA based polymers (PR pharmaceuticals), PLA-PEG based hydrogels (Medincell) and PEA based polymers (Medivas).

Accordingly, the antibody molecules of the present invention can be formulated into compositions using pharmaceutically acceptable ingredients as well as established methods of preparation (Gennaro, A. L. and Gennaro, A. R. (2000) Remington: The Science and Practice of Pharmacy, 20th Ed., Lippincott Williams & Wilkins, Philadelphia, Pa.). To prepare the pharmaceutical compositions, pharmaceutically inert inorganic or organic excipients can be used. To prepare e.g. pills, powders, gelatine capsules or suppositories, for example, lactose, talc, stearic acid and its salts, fats, waxes, solid or liquid polyols, natural and hardened oils can be used. Suitable excipients for the production of solutions, suspensions, emulsions, aerosol mixtures or powders for reconstitution into solutions or aerosol mixtures prior to use include water, alcohols, glycerol, polyols, and suitable mixtures thereof as well as vegetable oils.

The pharmaceutical composition may also contain additives, such as, for example, fillers, binders, wetting agents, glidants, stabilizers, preservatives, emulsifiers, and furthermore solvents or solubilizers or agents for achieving a depot effect. The latter is that fusion proteins may be incorporated into slow or sustained release or targeted delivery systems, such as liposomes and microcapsules.

The formulations can be sterilized by numerous means, including filtration through a bacteria-retaining filter, or by incorporating sterilizing agents in the form of sterile solid compositions which can be dissolved or dispersed in sterile water or other sterile medium just prior to use.

Numerous possible applications for the inventive antibody molecule exist in medicine. In addition to their use in in vitro diagnostics or drug delivery, an antibody molecule of the invention, which binds, for example, tissue- or tumor-specific cellular surface molecules can be generated.

The invention is further illustrated by the following non-limiting Examples.

Example I

A bispecific Fc-attenuated bivalent molecule, also designated to be of the bsFc$^{ko}$-1/2-format, with tumour×CD3 specificity, as schematically depicted in FIG. 1E, was generated. Modifications of amino acids of the hinge region and of the $C_H2$ domain were introduced as shown in FIG. 1O. Bispecific Fc-attenuated tetravalent molecules, also designated to be of the bsFc$^{ko}$-1-format, with tumour×CD3 specificity, as schematically depicted in FIG. 1G, were generated. Modifications of amino acids of the hinge region and of the $C_H2$ domain were introduced as shown in FIG. 1P.

Figure 2:
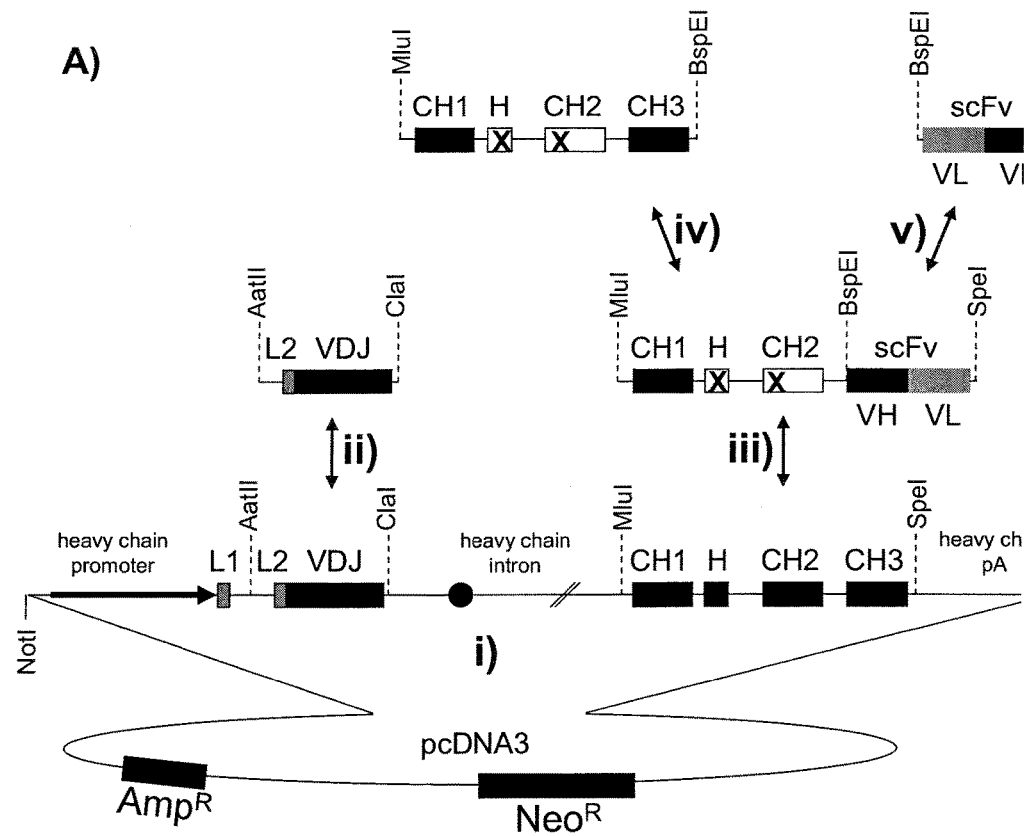
Figure 2:
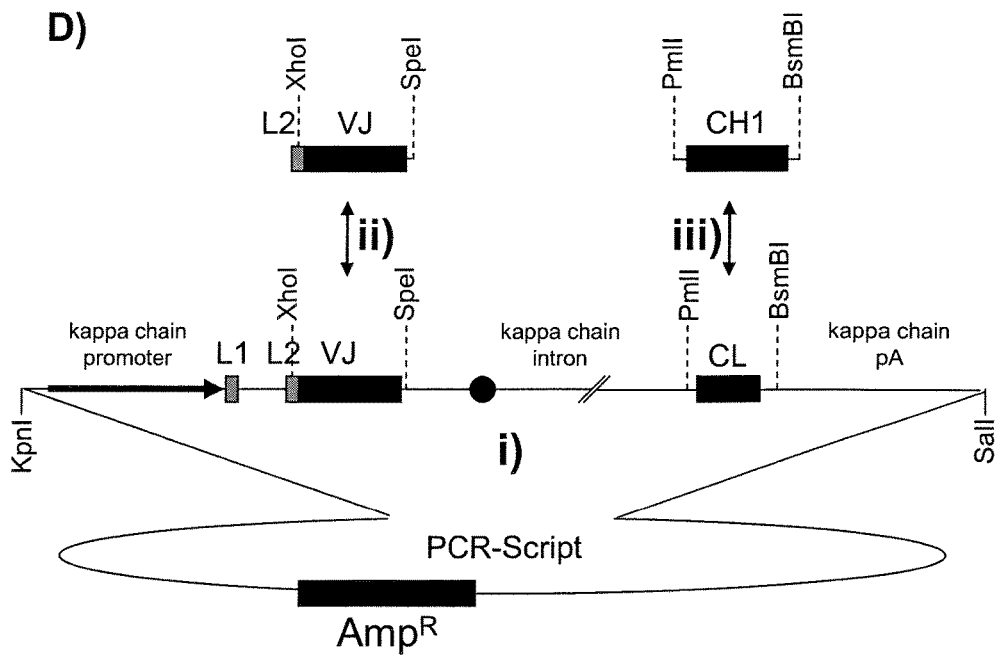
Figure 2:
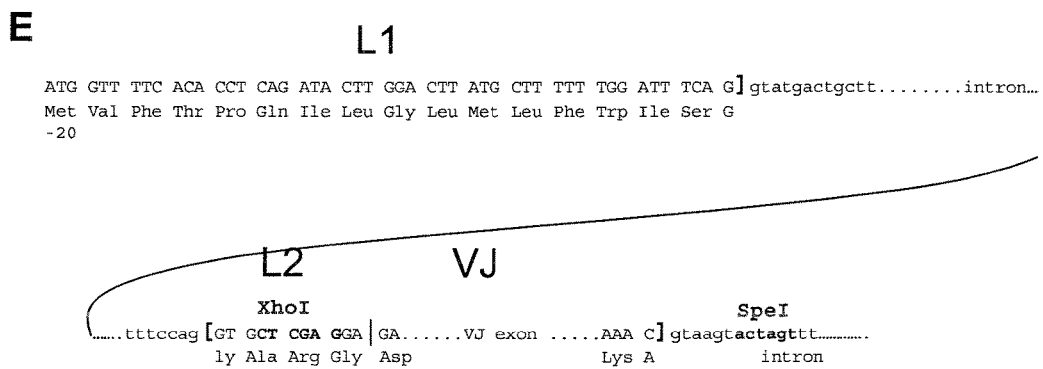
Figure 2:
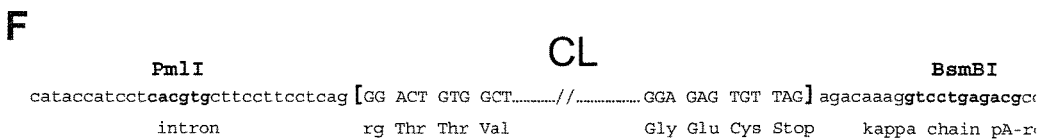

Cloning and amplification of plasmids was carried out using *Escherichia coli* DH5α (Invitrogen, Karlsruhe, Germany). The build-up of the respective vectors is depicted in FIG. 2.

Cotransfection of expression vectors encoding main and smaller chains, which can also be referred to as heavy and light chains, of indicated specificities was done in Sp2/0 plasmocytoma cells, obtained from the American Type Culture Collection (ATCC, Manassas, Va.). For the build-up of the respective vectors reference is made to FIG. 2 (see also Example II below). Cells were cultured in IMDM media, supplemented with 10% fetal calf serum (PAN-Biotech, Aidenbach, Germany), 1% penicillin and streptomycin (Lonza, Basel, Switzerland). Stable transfectants were selected by adding 1 mg/ml G418 (Invitrogen, Karlsruhe, Germany).

Bispecific antibodies were purified from supernatants of cultures of stably transfected cells via affinity chromatography using protein A for the Fc$^{ko}$-1 format and KappaSelect for the bsFc$^{ko}$-1/2 format (both chromatography media were obtained from GE Healthcare, Munich, Germany).

Example II

Immunoglobulin V regions were combined with the desired constant C regions in an expression vector. The cloning procedure indicated here allows the introduction of complete Ig V regions and their expression in lymphoid cells without any alterations of their amino acid sequence. To this end, the nucleotide sequence of a VDJ and VJ fragment of a monospecific antibody was used to design primer pairs (C C'; D D'; Table 1). The reamplified DNA fragments of the V segments were digested (VJ directly and VDJ after reamplification with primer pair E E' Table 1) with appropriate restriction nucleases (summarized in Table 1) and then ligated into the expression vectors. Alternatively, the V domains were synthezised as DNA fragments at GeneArt, Regensburg, Germany. This method was used for genes coding for the V regions of the antibody directed to EGFR (clone C225). The vectors (FIG. 2) contain human heavy and human light constant region genes. Thus, insertion of the amplified and digested V segments reconstitutes the original genomic organisation of the Ig genes in the vectors without altering any amino acid of the V regions.

The original vector for the heavy chain contains the human γ1 isotype Ig heavy chain (FIG. 2A). Restriction sites were introduced at the required positions in introns in order to exchange the AatII-ClaI fragment with the VDJ fragment of the heavy chain of monoclonal antibodies 4G8 (anti-Flt3), BV10 (anti-FLT3), 4G7 (anti-CD19), C225 (anti-EGFR) and 9.2.27 (anti-CSPG4) or any other monoclonal antibody. The region relevant for cloning the VDJ fragment is shown enlarged in FIG. 2B. The fragment to be exchanged contains parts of the first intron with an AatII restriction site, the second exon of the leader sequence, the VDJ region and part of the heavy chain intron with the restriction site ClaI. For the substitution of all exons of the constant region of the human γ1 heavy chain restriction sites were introduced at the required position in the heavy chain intron (MluI) and in the 5'-UTR heavy chain polyA-region (pA-region; SpeI), as shown in FIGS. 2A and 2C.

Furthermore, with the expression vectors constructed, it is possible to exchange the entire constant region of the human Igγ1 isotype (MluI-SpeI fragment; see FIG. 2A) either against constant regions of all other antibody isotypes or against Fc parts with optimized or reduced effector function. In the case of antibodies optimized for triggering ADCC amino acid substitutions were introduced in the CH2 domain of human γ1 constant region as shown in International patent applications WO2011/076922 and WO2011/089211. In order to generate bispecific antibodies as depicted in FIGS. 1A-N MluI and SpeI flanked DNA fragments containing either exons coding for wildtype or modified constant domains of the Ig heavy chain can be inserted. The MluI-SpeI fragment to be exchanged is shown enlarged in FIG. 2C. Adding the second antigen specificity of a bispecific antibody, scFv-fragments either in VH-VL or VL-VH orientation can be included via the restriction enzyme sites BspEI and SpeI, as also shown in FIG. 2A. The region relevant for cloning of a scFv fragment in VL-VH orientation is shown enlarged in FIG. 2C. ScFv fragments with the specificity for CD3 (clone humanized UCHT1; VL-VH orientation), CD28 (clone 9.3; VL-VH orientation), TCRα/β (clone BMA031; VH-VL orientation) were generated by PCR with oligonucleotides F and F' listed in Table 2. Alternatively, they were synthesized as DNA-fragments at GeneArt, Regensburg, Germany. This method was used for genes coding for the antibodies directed to CD16 (clone 3G8; VL-VH orientation). The DNA fragment of the scFv segments in VH-VL and VL-VH orientation, respectively, was digested with the appropriate restriction nucleases (summerized in Table 2) and was then ligated into the expression vector.

The original vector for the light chain contains the VJ region of the light chain and the C region of human κ gene (FIG. 2D). Restriction sites were introduced at the required locations (XhoI and SpeI) in order to substitute the light chain XhoI-SpeI fragment with the appropriate VJ fragment of the light chain of monoclonal antibodies 4G8 (anti-FLT3), BV10 (anti-FLT3), 4G7 (anti-CD19), C225 (anti-EGFR) or 9.2.27 (anti-CSPG4) or any other monoclonal antibody. The region adjacent to the fragment to be exchanged is shown in FIG. 2E. This region contains parts of the second exon of the leader sequence, a suitable restriction site (XhoI) for in frame fusion, the VJ region and parts of the kappa chain intron with restriction site SpeI. In order to replace the constant domain of the light chain (CL) restriction sites were introduced at the required locations (PmII and BsmBI). The region adjacent to the fragment to be exchanged is shown enlarged in FIG. 2F. This region contains parts of the kappa chain intron, a suitable restriction site (PmII), the CL region and parts of the 3'-UTR region kappa chain polyA-region (pA-region) with restriction site (BsmBI).

TABLE 1

Oligonucleotides used for amplification of VDJ and VJ segments for the insertion into expression vectors Oligonucleotides used for the heavy chain VDJ segment

| | | |
|---|---|---|
| C | 4G7-H-for | 5'-ctc ttc aca ggt gtc ctc tct gag gtc cag ctg cag cag tct gga cct g-3' (SEQ ID NO: 27) |
| C' | 4G7-H-rev | 5'-ggg aga agg tag gac tca cct gag gag act gtg aga gtg gtg cct ggc ccc cag tag tc-3' (SEQ ID NO: 28) |
| C | 9.2.27-H-for | 5'-tct tca cag gtg tcc tct ccc agg tga agc tgc agc aat ctg gac ctg agc-3' (SEQ ID NO: 29) |
| C' | 9.2.27-H-rev | 5'-aat ggg aga agg tag gac tca cct gag gag acg gtg acc gtg gtc cct tgg-3' (SEQ ID NO: 30) |
| C | 4G8-H-for | 5'-tct ctt cac agg tgt cct ctc cag gtc caa ctg ca gca gcc tgg ggc tga gc-3' (SEQ ID NO: 31) |
| C' | 4G8-H-rev | 5'-gag aag gta gga ctc acc tga gga gac tgt gag agt ggt gcc ttg gcc cca g-3' (SEQ ID NO: 32) |
| C | BV10-H-for | 5'-aga cgt cca ctc tgt ctt tct ctt cac agg tgt cct ctc cag gtc agc tga agc agt c-3'(SEQ ID NO: 33) |
| C' | BV10-H-rev | 5'-gag aag gta gga ctc acc tga gga gac ggt gac tga ggt tcc ttg acc c-3' (SEQ ID NO: 34) |
| E | universal for (AatII) | 5'-aga cgt cca ctc tgt ctt tct ctt cac agg tgt cct ctc c-3' (SEQ ID NO: 35) |
| E' | universal rev (ClaI) | 5'-tat cga ttt aga atg gga gaa ggt agg act cac-3' (SEQ ID NO: 36) |

Oligonucleotides used for the light chain VJ segment

| | | |
|---|---|---|
| D | 4G7-L-for (XhoI) | 5'-act cga gga gat att gtg atg act cag gct gca ccc tct ata c-3' (SEQ ID NO: 37) |
| D' | 4G7-L-rev (SpeI) | 5'-aac tag tac tta cgt ttc agc tcc agc ttg gtc cca gca ccg aac gt-3' (SEQ ID NO: 38) |
| D | 9.2.27-L-for (XhoI) | 5'-tct cga gga gac atc gag ctc act cag tct cca gct tct ttg-3' (SEQ ID NO: 39) |
| D' | 9.2.27-L-rev (SpeI) | 5'-aac tag tac tta cgt ttg atc tcc agc ttg gtg ccc ctc caa ag-3' (SEQ ID NO: 40) |
| D | 4G8-L-for (XhoI) | 5'-act cga gga gat att gtg cta act cag tct cca gcc acc ctg-3' (SEQ ID NO: 41) |
| D' | 4G8-L-rev (SpeI) | 5'-tac tag tac tta cgt ttt att tcc agc ttg gtc ccc ctc c-3' (SEQ ID NO: 42) |
| D | BV10-L-for (XhoI) | 5'-act cga gga gac att gtg atg aca cag tct cca tcc tcc c-3' (SEQ ID NO: 43) |
| D' | BV10-L-rev (SpeI) | 5'-act agt act tac gtt tca gct cca gct tgg tcc agc acc gaa cgt g-3' (SEQ ID NO: 44) |

Restriction sites are shown in bold and indicated by letters in parentheses.

TABLE 2

Oligonucleotides used for amplification of scFv segments for the insertion into expression vectors
Oligonucleotides used for the scFv segment

| | | |
|---|---|---|
| F | UCHT1-for (BspEI) | 5'-atc cgg aga tat cca gat gac cca gtc ccc gag ctc cct g-3' (SEQ ID NO: 45) |
| F' | UCHT1-rev (SpeI) | 5'-tac tag tta tca cga gga gac ggt gac cag ggt tcc ttg acc cca-3' (SEQ ID NO: 46) |
| F | BMA031-for (BspEI) | 5'-atc cgg aga gt gca gct gca gca gtc cgg ccc tga gct-3' (SEQ ID NO: 47) |
| F' | BMA031-rev (SpeI) | 5'-tac tag tta tca ctt cag ttc agc tt ggt gcc agc gcc gaa ggt-3' (SEQ ID NO: 48) |

TABLE 2-continued

Oligonucleotides used for amplification of scFv
segments for the insertion into expression vectors
Oligonucleotides used for the scFv segment

| F | 9.3-for (BspEI) | 5'-atc cgg aga cat tgt gct gac cca gtc ccc tgc ctc cct gg-3' (SEQ ID NO: 49) |
|---|---|---|
| F' | 9.3-rev (SpeI) | 5'-tac tag tta tca aga gct cac agt cac tgt ggt gcc ctg gcc cca-3' (SEQ ID NO: 50) |

Restriction sites are shown in bold and indicated by letters in parentheses.

Thus, bispecific antibody molecules with FLT3×CD3 (4G8×UCHT1, BV10×UCHT1), FLT3×TCRα/β (4G8×BMA031, BV10×BMA031), FLT3×CD28 (4G8×9.3, BV10×9.3), FLT3×CD16 (4G8×3G8, BV10×3G8), CD19×CD3 (4G7×UCHT1), CD19×TCRα/β (4G7×BMA031), CD19×CD28 (4G7×9.3), CD19×CD16 (4G7×3G8), CSPG4×CD3 (9.2.27×UCHT1), CSPG4×TCRα/β (9.2.27×BMA031), CSPG4×CD28 (9.2.27×9.3), CSPG4×CD16 (9.2.27×3G8), EGFR×CD3 (C225×UCHT1), EGFR×TCRα/β (C225×BMA031), EGFR×CD28 (C225×9.3), EGFR×CD16 (C225×3G8) as tetravalent bsFc$^{-KO}$-1 and bivalent bsFc$^{-KO}$-1/2 were obtained. Sequences of the corresponding chains are depicted as SEQ ID NO: 1 to SEQ ID NO: 26 and in FIG. 6.

Cotransfection of the expression vectors encoding the chimeric heavy and light chain (IgG1/κ) or modified heavy chains into the non-Ig-producing myeloma cell line Sp2/0 yielded stable transfectomas secreting bispecific monoclonal antibodies which are able to bind specifically to the desired antigen. The functional characterisation of these antibody molecules is illustrated in the following experiments using FLT3×CD3, CD19×TCRα/β and CSPG×CD3 bispecific antibody molecules.

Example III

Figure 3:
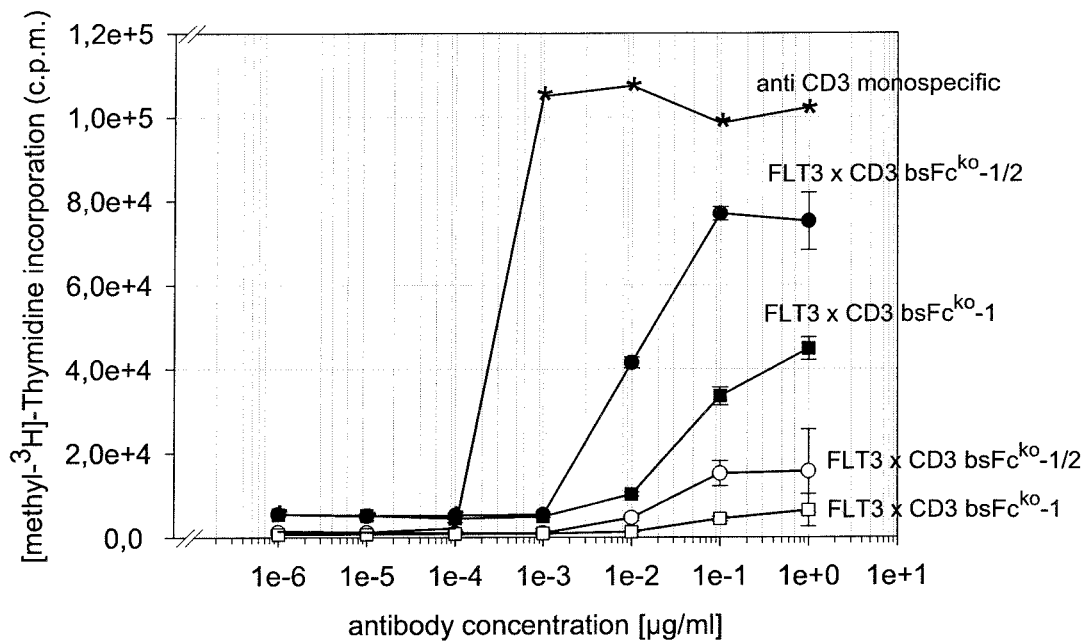
Figure 3:
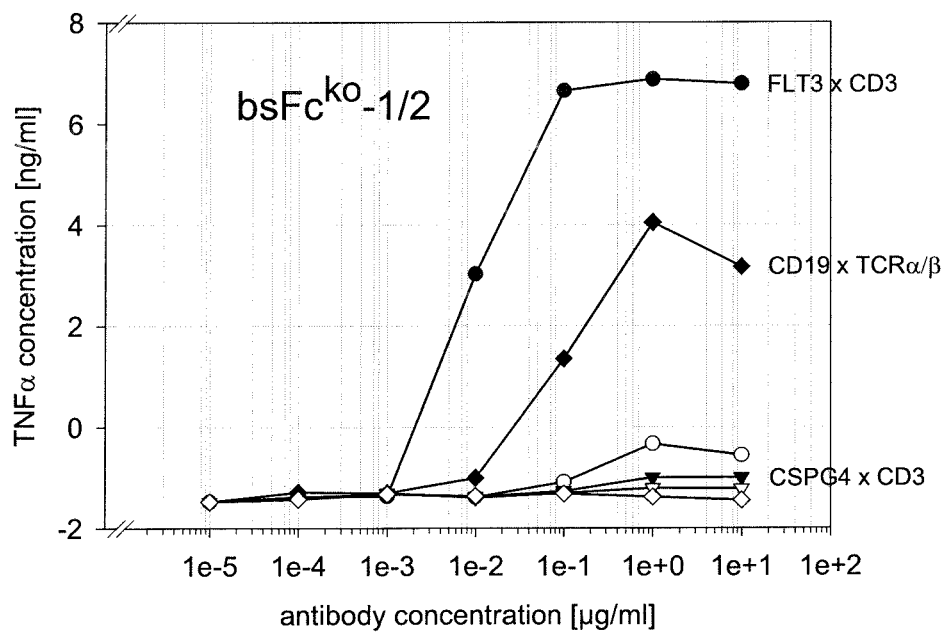

T cell activation by the two antibody formats of Example I, the bsFc$^{ko}$-1/2-format and the bsFc$^{ko}$-1-format, with and without FLT3/CD19 positive REH cells was determined. Data are shown in FIG. 3. The bispecific antibody molecules used had the FLT3 binding site (first binding site) of clone 4G8 and a CD3 binding site (second binding site) of clone UCHT1. The "bsFc$^{ko}$-1/2-format" molecule was comprised of the chains of SEQ ID NO: 1 and SEQ ID NO: 6) and the "bsFc$^{ko}$-1-format" molecule was comprised of the chains of SEQ ID NO: 1 and SEQ ID NO: 26. The bispecific antibody molecule that binds CSPG4 and CD3 was in the "bsFc$^{ko}$-1/2 format" and was comprised of the chains of SEQ ID NO: 3 and SEQ ID NO: 18. In addition a bispecific antibody molecule in the "bsFc$^{ko}$-1/2 format" binding CD19 and TCRα/β comprised of the chains of SEQ ID NO: 4 and SEQ ID NO: 15 was used.

A) Human mononuclear cells (PBMCs) were obtained from peripheral blood of healthy donors and isolated using density gradient centrifugation. PBMCs were transferred to 96 well plates (100,000/well). Subsequently, either irradiated FLT3/CD19 positive REH cells (50,000/well) or medium were added, and finally antibodies were added at concentrations as indicated (FIG. 3A). After 24 hours cells were incubated with $^3$H tymidine (0.5 μCi/well). After a further 24 hours cells were applied onto glass fiber filters using a cell harvester. Radioactivity was subsequently detected by means of a scintillation counter.

B) Heparinized whole blood (50 μl/well) was incubated in 96 well plates with and without FLT3/CD19 positive REH cells (50,000/well) and with antibodies at the concentrations indicated in FIG. 3B. After 24 hours the concentration of TNF in the supernatant was determined by ELISA.

REH cells (Deutsche Sammlung für Mikroorganismen and Zellkulturen, DSMZ, Braunschweig, Germany) and PBMCs were cultured in RPMI 1640 medium, supplemented with 10% fetal calf serum (PAN-Biotech, Aidenbach, Germany), 1% penicillin and streptomycin (Lonza, Basel, Switzerland).

Example IV

The lysis of FLT3/CD19 expressing REH cells (FIG. 4A) and CSPG expressing SKMel63 cells (FIG. 4B) by bispecific antibodies and activated CD8+ T killer cells was determined.

Human mononuclear cells (PBMCs) were stimulated using the monospecific CD3 antibody UCHT1 (10 ng/ml) for three days. Subsequently activated CD8+ T cells were isolated by positive selection using magnetic cell sorting. The cells were added to $^{51}$Cr labelled FLT3/CD19 positive REH cells (FIG. 4A) or CSPG4-positive SKMel63 cells (FIG. 4B), and incubated with antibodies at the concentrations as indicated. After 4 hours cell supernatants were harvested onto scintillation plates and radioactivity was determined in a scintillation counter.

Specific lysis in percent was analysed under defined experimental conditions as follows: cpm(exp)−cpm(bg)/cpm(100)−cpm(bg), wherein cpm(bg) corresponds to the chromium release without antibody and effector cells, and cpm(100) corresponds to the chromium release after incubation of target cells with a detergent.

SKMel63 cells were obtained from Dr. B. Gückel, Klinik für Gynakologie, University of Tübingen, Germany.

Example V

Aggregation and production rate of FLT3×CD3 antibodies (FLT binding site: clone 4G8, CD3 binding site: clone UCHT1) having identical specificity was compared between three different formats: bispecific single-chain format (bs-scFv), bsFc$^{ko}$-1/2-Format, bsFc$^{ko}$-1-Format. The antibody molecule of the "bsFc$^{ko}$-1/2-format" was comprised of the chains of SEQ ID NO: 1 and SEQ ID NO: 6 and the antibody molecule of the "bsFc$^{ko}$-1-format" was comprised of the chains of SEQ ID NO: 1 and SEQ ID NO: 26.

Bispecific single chain molecules were purified by affinity chromatography using protein L.

Gelfiltration was performed using a superdex 200 PC3.2/30 column and a SMARTSystem (GE-Healthcare, Munich, Germany). Standard proteins used were katalase (232 kDa, from bovine liver), aldolase (158 kDa; from rabbit muscle), albumin (67 kDa; from bovine serum) and ribonuclease A (13.7 kDa; from bovine pancreas). Results are shown in FIG. 5A. It is evident from FIG. 5A that formation of aggregates is considerably more pronounced if the antibody is expressed as bs-scFv (43% aggregation rate) rather than bsFcko-1/2 (no aggregation detected) or bsFcko-1 (2% aggregration rate), i.e. the bispecific antibody molecules of the present invention remain monomeric molecules with essentially no aggregation tendency.

For comparison of production rates the genes encoding for bispecific molecules containing the 4G8 (anti-FLT3) and the UCHT1 (anti-CD3)-specificity in the depicted formats were introduced into Sp2/0 cells and antibodies were purified using affinity chromatography. The amount of antibody purified from the supernatants of clones selected for maximal production is depicted in FIG. 5B. Antibody concentrations were determined by optical spectroscopy assuming an optical density at 280 nm of 1.4 for an antibody concentration of 1 mg/ml. The production rates for the bsFcko-1/2 and bsFcko-1 antibody molecules of the invention were significantly higher than those for the respective bs-scFv molecule.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The compositions, methods, procedures, treatments, molecules and specific compounds described herein are presently representative of certain embodiments are exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

REFERENCE LIST

1. Davis, L., Vida, R. and Lipsky, P. E. Regulation of human T lymphocyte mitogenesis by antibodies to CD3, J. Immunol., 137: 3758-3767, 1986.
2. Jung, G., Ledbetter, J. A. and Muller-Eberhard, H. J. Induction of cytotoxicity in resting human T lymphocytes bound to tumor cells by antibody heteroconjugates, Proc. Natl. Acad. Sci. U.S.A, 84: 4611-4615, 1987.
3. Jung, G. and Eberhard, H. J. An in-vitro model for tumor immunotherapy with antibody heteroconjugates, Immunol. Today, 9: 257-260, 1988.
4. Staerz, U. D., Kanagawa, O. and Bevan, M. J. Hybrid antibodies can target sites for attack by T cells, Nature, 314: 628-631, 1985.
5. Perez, P., Hoffman, R. W., Shaw, S., Bluestone, J. A. and Segal, D. M. Specific targeting of cytotoxic T cells by anti-T3 linked to anti-target cell antibody, Nature, 316: 354-356, 1985.
6. Jung, G., Honsik, C. J., Reisfeld, R. A. and Muller-Eberhard, H. J. Activation of human peripheral blood mononuclear cells by anti-T3: killing of tumor target cells coated with anti-target-anti-T3 conjugates, Proc. Natl. Acad. Sci. U.S.A, 83: 4479-4483, 1986.
7. Jung, G. and Eberhard, H. J. An in-vitro model for tumor immunotherapy with antibody heteroconjugates, Immunol. Today, 9: 257-260, 1988.
8. Jung, G., Freimann, U., Von, M. Z., Reisfeld, R. A. and Wilmanns, W. Target cell-induced T cell activation with bi- and trispecific antibody fragments, Eur. J. Immunol., 21: 2431-2435, 1991.
9. Rosenberg, S. A., Lotze, M. T., Yang, J. C., Aebersold, P. M., Linehan, W. M., Seipp, C. A. and White, D. E. Experience with the use of high-dose interleukin-2 in the treatment of 652 cancer patients, Ann. Surg., 210: 474-484, 1989.
10. Tibben, J. G., Boerman, O. C., Massuger, L. F., Schijf, C. P., Claessens, R. A. and Corstens, F. H. Pharmacokinetics, biodistribution and biological effects of intravenously administered bispecific monoclonal antibody OC/TR F(ab')2 in ovarian carcinoma patients, Int. J. Cancer, 66: 477-483, 1996.
11. Kroesen, B. J., Buter, J., Sleijfer, D. T., Janssen, R. A., van der Graaf, W. T., The, T. H., de, L. L. and Mulder, N. H. Phase I study of intravenously applied bispecific antibody in renal cell cancer patients receiving subcutaneous interleukin 2, Br. J. Cancer, 70: 652-661, 1994.
12. Jung, G. and Eberhard, H. J. An in-vitro model for tumor immunotherapy with antibody heteroconjugates, Immunol. Today, 9: 257-260, 1988.
13. Jung, G., Freimann, U., Von, M. Z., Reisfeld, R. A. and Wilmanns, W. Target cell-induced T cell activation with bi- and trispecific antibody fragments, Eur. J. Immunol., 21: 2431-2435, 1991.
14. Bargou, R., Leo, E., Zugmaier, G., Klinger, M., Goebeler, M., Knop, S., Noppeney, R., Viardot, A., Hess, G., Schuler, M., Einsele, H., Brandl, C., Wolf, A., Kirchinger, P., Klappers, P., Schmidt, M., Riethmuller, G., Reinhardt, C., Baeuerle, P. A. and Kufer, P. Tumor regression in cancer patients by very low doses of a T cell-engaging antibody, Science, 321: 974-977, 2008.
15. Topp, M. S., Kufer, P., Gokbuget, N., Goebeler, M., Klinger, M., Neumann, S., Horst, H. A., Raff, T., Viardot, A., Schmid, M., Stelljes, M., Schaich, M., Degenhard, E., Kohne-Volland, R., Bruggemann, M., Ottmann, O., Pfeifer, H., Burmeister, T., Nagorsen, D., Schmidt, M., Lutterbuese, R., Reinhardt, C., Baeuerle, P. A., Kneba, M., Einsele, H., Riethmuller, G., Hoelzer, D., Zugmaier, G. and Bargou, R. C. Targeted therapy with the T-cell-engaging antibody blinatumomab of chemotherapy-refractory minimal residual disease in B-lineage acute lymphoblastic leukemia patients results in high response rate and prolonged leukemia-free survival, J. Clin. Oncol., 29: 2493-2498, 2011.
16 Brischwein, K., Parr, L., Pflanz, S., Volkland, J., Lumsden, J., Klinger, M., Locher, M., Hammond, S. A., Kiener, P., Kufer, P., Schlereth, B. and Baeuerle, P. A. Strictly target cell-dependent activation of T cells by bispecific single-chain antibody constructs of the BiTE class, J. Immunother., 30: 798-807, 2007.
17 Bargou, R., Leo, E., Zugmaier, G., Klinger, M., Goebeler, M., Knop, S., Noppeney, R., Viardot, A., Hess, G., Schuler, M., Einsele, H., Brandl, C., Wolf, A., Kirchinger, P., Klappers, P., Schmidt, M., Riethmuller, G., Reinhardt, C., Baeuerle, P. A. and Kufer, P. Tumor regression in cancer patients by very low doses of a T cell-engaging antibody, Science, 321: 974-977, 2008.
18 Topp, M. S., Kufer, P., Gokbuget, N., Goebeler, M., Klinger, M., Neumann, S., Horst, H. A., Raff, T., Viardot, A., Schmid, M., Stelljes, M., Schaich, M., Degenhard, E., Kohne-Volland, R., Bruggemann, M., Ottmann, O., Pfeifer, H., Burmeister, T., Nagorsen, D., Schmidt, M., Lutterbuese, R., Reinhardt, C., Baeuerle, P. A., Kneba, M., Einsele, H., Riethmuller, G., Hoelzer, D., Zugmaier, G. and Bargou, R. C. Targeted therapy with the T-cell-engaging antibody blinatumomab of chemotherapy-refractory minimal residual disease in B-lineage acute lymphoblastic leukemia patients results in high response rate and prolonged leukemia-free survival, J. Clin. Oncol., 29: 2493-2498, 2011.
19 Grosse-Hovest, L., Hartlapp, I., Marwan, W., Brem, G., Rammensee, H. G. and Jung, G. A recombinant bispecific single-chain antibody induces targeted, supra-agonistic CD28-stimulation and tumor cell killing, Eur. J. Immunol., 33: 1334-1340, 2003.
20 Grosse-Hovest, L., Muller, S., Minoia, R., Wolf, E., Zakhartchenko, V., Wenigerkind, H., Lassnig, C., Besenfelder, U., Muller, M., Lytton, S. D., Jung, G. and Brem, G. Cloned transgenic farm animals produce a bispecific antibody for T cell-mediated tumor cell killing, Proc. Natl. Acad. Sci. U.S.A, 101: 6858-6863, 2004.
21 Marvin, J. S. and Zhu, Z. Recombinant approaches to IgG-like bispecific antibodies, Acta Pharmacol. Sin., 26: 649-658, 2005.
22 Mabry, R., Lewis, K. E., Moore, M., McKernan, P. A., Bukowski, T. R., Bontadelli, K., Brender, T., Okada, S., Lum, K., West, J., Kuijper, J. L., Ardourel, D., Franke, S., Lockwood, L., Vu, T., Frank, A., Appleby, M. W., Wolf, A., Reardon, B., Hamacher, N. B., Stevens, B., Lewis, P., Lewis, K. B., Gilbertson, D. G., Lantry, M., Julien, S. H., Ostrander, C., Chan, C., Byrnes-Blake, K., Brody, J., Presnell, S., Meengs, B., Levin, S. D. and Snavely, M. Engineering of stable bispecific antibodies targeting IL-17A and IL-23, Protein Eng Des Sel, 23: 115-127, 2010.
23 Marvin, J. S. and Zhu, Z. Recombinant approaches to IgG-like bispecific antibodies, Acta Pharmacol. Sin., 26: 649-658, 2005.
24 Mabry, R., Lewis, K. E., Moore, M., McKernan, P. A., Bukowski, T. R., Bontadelli, K., Brender, T., Okada, S., Lum, K., West, J., Kuijper, J. L., Ardourel, D., Franke, S., Lockwood, L., Vu, T., Frank, A., Appleby, M. W., Wolf, A., Reardon, B., Hamacher, N. B., Stevens, B., Lewis, P., Lewis, K. B., Gilbertson, D. G., Lantry, M., Julien, S. H., Ostrander, C., Chan, C., Byrnes-Blake, K., Brody, J., Presnell, S., Meengs, B., Levin, S. D. and Snavely, M. Engineering of stable bispecific antibodies targeting IL-17A and IL-23, Protein Eng Des Sel, 23: 115-127, 2010.
25. Dall'Aqua et al. "Contribution of domain interface residues to the stability of antibody CH3 domain homodimers" Biochemistry (1998) Volume: 37, Issue: 26, Pages: 9266-9273.
26 S. Miller Protein-Protein Recognition and the Association of Immunoglobulin Constant Domains. J. Mol. Biol. (1990) Volume 216 pp 965-973
27 J. Deisenhofer, Crystallographic refinement and atomic models of a human Fc fragment and its complex with fragment B of protein A from *Staphylococcus aureus* at 2.9- and 2.8-A resolution. Biochemistry (1981) Volume 20 pp 2361-2370
28 Roopenian & Akilesh; FcRn: the neonatal Fc receptor comes of age. Nature Reviews Immunology (2007) Volume 7 pp: 715-725.
29 Reiter Y., Brinkmann U., Kreitman R. J., Jung S-H., Lee B and Pastan I., Stabilization of the Fv fragments in recombinant immunotoxins by disulfide bonds engineered into conserved framework regions, Biochemistry 1994, 33, 6551-5459.
30 International Patent Application WO2011/076922
31 International Patent Application WO2011/089211

What is claimed is:

1. A recombinant bispecific antibody molecule consisting of a Fab fragment comprising a first binding site for a first antigen, a single chain Fv fragment comprising a second binding site for a second antigen and an immunoglobulin IgG1 CH2 domain,
wherein the Fab fragment and the single chain Fv fragment are linked via the CH2 domain,
wherein at least three amino acid residues of the CH2 domain that are able to mediate binding to Fc receptors are deleted or mutated by substitution with a different amino acid, thereby attenuating the binding of the CH2 domain to Fc receptors, wherein the at least three amino acid residues of the CH2 domain consist of sequence position 233 and at least two amino acids selected from the group consisting of sequence position 228, 230, 231, 232, 234, 235, 236, 237, 238, 265, 297, 327, and 330 (numbering of sequence positions according to the EU-index), and
wherein further the amino acid residues of sequence positions 226 and 229 are deleted or mutated by substitution with a different amino acid,
wherein either the first binding site or the second binding site binds a tumor associated antigen, and
wherein the other of the first binding site or the second binding site binds a T cell or NK (natural killer) cell specific receptor molecule.

2. The antibody molecule of claim 1, wherein the tumor associated antigen is selected from the group consisting of CD10, CD19, CD20, CD21, CD22, CD25, CD30, CD33, CD34, CD37, CD44v6, CD45, CDw52, Fms-like tyrosine kinase 3 (FLT-3, CD135), c-Kit (CD117), CSF1R, (CD115), CD133, PDGFR-α (CD140a), PDGFR-β (CD 140b), chondroitin sulfate proteoglycan 4 (CSPG4, melanoma-associated chondroitin sulfate proteoglycan), Muc-1, EGFR, de2-7-EGFR, EGFRvIII, Folate binding protein, Her2neu, Her3, PSMA, PSCA, PSA, TAG-72, HLA-DR, IGFR, CD133, IL3R, fibroblast activating protein (FAP), Carboanhydrase IX (MN/CA IX), Carcinoembryonic antigen (CEA), EpCAM, CDCP1, Derlin1, Tenascin, frizzled 1-10, VEGFR2 (KDR/FLK1), VEGFR3 (FLT4, CD309), Endoglin, CLEC14, Tem1-8, and Tie2.

3. The antibody molecule of claim 1, wherein the T-cell or NK cell specific receptor molecule is one of CD3, the T cell receptor (TCR), CD28, CD16, NKG2D, Ox40, 4-1BB, CD2, CD5 and CD95.

4. The antibody molecule of claim 3, wherein the TCR is TCR (alpha/beta) or TCR (gamma/delta).

5. The antibody molecule of claim 1, wherein the Fab fragment is linked to the CH2 domain via the heavy chain CH1 and VH domains of the Fab fragment or via the CL and VL light chain domains of the Fab fragment.

6. The antibody molecule of claim 5, wherein the heavy chain domains of the Fab fragment or the light chain domains of the Fab fragment are arranged at the N-terminus of the antibody molecule.

7. The antibody molecule of claim 6, wherein the CH2 domain is linked to the scFv fragment via the variable domain of the light chain (VL domain) of the scFv fragment that comprises the second binding site.

8. The antibody molecule of claim 6, wherein the CH2 domain is linked to the scFv fragment via the variable domain of the heavy chain (VH domain) of the scFv fragment that comprises the second binding site.

9. The antibody molecule of claim 1, wherein the Fab fragment that comprises the first binding site for the first antigen consists of the VL domain fused to the CH1 domain and the VH domain fused to the CL domain.

10. The antibody molecule of claim 9, wherein the CH1 domain of the Fab fragment is fused to the CH2 domain.

11. The antibody molecule of claim 9, wherein the VL-CH1 chain of the Fab fragment is arranged at the N-terminus of the antibody molecule.

12. The antibody molecule of claim 1, wherein the first binding site binds a tumor associated surface antigen and the second binding site binds one of CD3, the T cell receptor (TCR), CD28, CD16, NKG2D, Ox40, 4-1BB, CD2, CD5 and CD95.

13. A pharmaceutical composition comprising an antibody molecule as defined in claim 1.

* * * * *

SEQUENCE LISTING

```
<160> NUMBER OF SEQ ID NOS: 50

<210> SEQ ID NO 1
<211> LENGTH: 214
<212> TYPE: PRT
<213> ORGANISM: Artificial Sequence
<220> FEATURE:
<223> OTHER INFORMATION: light chain sequence, anti-FLT3 chimeric light
      chain (clone 4G8)

<400> SEQUENCE: 1

Asp Ile Val Leu Thr Gln Ser Pro Ala Thr Leu Ser Val Thr Pro
1               5                   10                  15

Gly Asp Ser Val Ser Leu Ser Cys Arg Ala Ser Gln Ser Ile Ser
                20                  25                  30

Asn Asn Leu His Trp Tyr Gln Gln Lys Ser His Glu Ser Pro Arg
                35                  40                  45
```

```
Leu Leu Ile Lys Tyr Ala Ser Gln Ser Ile Ser Gly Ile Pro Ser
             50                  55                  60

Arg Phe Ser Gly Ser Gly Ser Gly Thr Asp Phe Thr Leu Ser Ile
             65                  70                  75

Asn Ser Val Glu Thr Glu Asp Phe Gly Val Tyr Phe Cys Gln Gln
             80                  85                  90

Ser Asn Thr Trp Pro Tyr Thr Phe Gly Gly Thr Lys Leu Glu
             95                 100                 105

Ile Lys Arg Thr Val Ala Ala Pro Ser Val Phe Ile Phe Pro Pro
            110                 115                 120

Ser Asp Glu Gln Leu Lys Ser Gly Thr Ala Ser Val Val Cys Leu
            125                 130                 135

Leu Asn Asn Phe Tyr Pro Arg Glu Ala Lys Val Gln Trp Lys Val
            140                 145                 150

Asp Asn Ala Leu Gln Ser Gly Asn Ser Gln Glu Ser Val Thr Glu
            155                 160                 165

Gln Asp Ser Lys Asp Ser Thr Tyr Ser Leu Ser Ser Thr Leu Thr
            170                 175                 180

Leu Ser Lys Ala Asp Tyr Glu Lys His Lys Val Tyr Ala Cys Glu
            185                 190                 195

Val Thr His Gln Gly Leu Ser Ser Pro Val Thr Lys Ser Phe Asn
            200                 205                 210

Arg Gly Glu Cys

<210> SEQ ID NO 2
<211> LENGTH: 220
<212> TYPE: PRT
<213> ORGANISM: Artificial Sequence
<220> FEATURE:
<223> OTHER INFORMATION: light chain sequence, anti-FLT3 chimeric light
      chain (clone BV10)

<400> SEQUENCE: 2

Asp Ile Val Met Thr Gln Ser Pro Ser Ser Leu Ser Val Ser Ala
1               5                  10                  15

Gly Glu Lys Val Thr Met Ser Cys Lys Ser Ser Gln Ser Leu Leu
             20                  25                  30

Asn Ser Gly Asn Gln Lys Asn Tyr Met Ala Trp Tyr Gln Gln Lys
             35                  40                  45

Pro Gly Gln Pro Pro Lys Leu Leu Ile Tyr Gly Ala Ser Thr Arg
             50                  55                  60

Glu Ser Gly Val Pro Asp Arg Phe Thr Gly Ser Gly Ser Gly Thr
             65                  70                  75

Asp Phe Thr Leu Thr Ile Ser Ser Val Gln Ala Glu Asp Leu Ala
             80                  85                  90

Val Tyr Tyr Cys Gln Asn Asp His Ser Tyr Pro Leu Thr Phe Gly
             95                 100                 105

Ala Gly Thr Lys Leu Glu Leu Lys Arg Thr Val Ala Ala Pro Ser
            110                 115                 120

Val Phe Ile Phe Pro Pro Ser Asp Glu Gln Leu Lys Ser Gly Thr
            125                 130                 135

Ala Ser Val Val Cys Leu Leu Asn Asn Phe Tyr Pro Arg Glu Ala
            140                 145                 150

Lys Val Gln Trp Lys Val Asp Asn Ala Leu Gln Ser Gly Asn Ser
            155                 160                 165
```

```
Gln Glu Ser Val Thr Glu Gln Asp Ser Lys Asp Ser Thr Tyr Ser
                170                 175                 180

Leu Ser Ser Thr Leu Thr Leu Ser Lys Ala Asp Tyr Glu Lys His
                185                 190                 195

Lys Val Tyr Ala Cys Glu Val Thr His Gln Gly Leu Ser Ser Pro
                200                 205                 210

Val Thr Lys Ser Phe Asn Arg Gly Glu Cys
                215                 220

<210> SEQ ID NO 3
<211> LENGTH: 218
<212> TYPE: PRT
<213> ORGANISM: Artificial Sequence
<220> FEATURE:
<223> OTHER INFORMATION: light chain sequence, anti-CSPG4 chimeric light
      chain (clone 9.2.27)

<400> SEQUENCE: 3

Asp Ile Glu Leu Thr Gln Ser Pro Ala Ser Leu Ala Val Ser Leu
1               5                   10                  15

Gly Gln Arg Ala Thr Ile Ser Cys Arg Ala Ser Glu Ser Val Asp
                20                  25                  30

Ser Tyr Gly Asn Ser Phe Met His Trp Tyr Gln Gln Lys Pro Gly
                35                  40                  45

Gln Pro Pro Lys Leu Leu Ile Tyr Leu Ala Ser Asn Leu Glu Ser
                50                  55                  60

Gly Val Pro Ala Arg Phe Ser Gly Ser Gly Ser Arg Thr Asp Phe
                65                  70                  75

Thr Leu Thr Ile Asp Pro Val Glu Ala Asp Asp Ala Ala Thr Tyr
                80                  85                  90

Tyr Cys Gln Gln Asn Asn Glu Asp Pro Leu Thr Phe Gly Gly Gly
                95                  100                 105

Thr Lys Leu Glu Ile Lys Arg Thr Val Ala Ala Pro Ser Val Phe
                110                 115                 120

Ile Phe Pro Pro Ser Asp Glu Gln Leu Lys Ser Gly Thr Ala Ser
                125                 130                 135

Val Val Cys Leu Leu Asn Asn Phe Tyr Pro Arg Glu Ala Lys Val
                140                 145                 150

Gln Trp Lys Val Asp Asn Ala Leu Gln Ser Gly Asn Ser Gln Glu
                155                 160                 165

Ser Val Thr Glu Gln Asp Ser Lys Asp Ser Thr Tyr Ser Leu Ser
                170                 175                 180

Ser Thr Leu Thr Leu Ser Lys Ala Asp Tyr Glu Lys His Lys Val
                185                 190                 195

Tyr Ala Cys Glu Val Thr His Gln Gly Leu Ser Ser Pro Val Thr
                200                 205                 210

Lys Ser Phe Asn Arg Gly Glu Cys
                215

<210> SEQ ID NO 4
<211> LENGTH: 219
<212> TYPE: PRT
<213> ORGANISM: Artificial Sequence
<220> FEATURE:
<223> OTHER INFORMATION: light chain sequence, anti-CD19 chimeric light
      chain (clone 4G7)

<400> SEQUENCE: 4
```

-continued

```
Asp Ile Val Met Thr Gln Ala Ala Pro Ser Ile Pro Val Thr Pro Gly
  1               5                  10                  15

Glu Ser Val Ser Ile Ser Cys Arg Ser Ser Lys Ser Leu Leu Asn Ser
             20                  25                  30

Asn Gly Asn Thr Tyr Leu Tyr Trp Phe Leu Gln Arg Pro Gly Gln Ser
         35                  40                  45

Pro Gln Leu Leu Ile Tyr Arg Met Ser Asn Leu Ala Ser Gly Val Pro
     50                  55                  60

Asp Arg Phe Ser Gly Ser Gly Ser Gly Thr Ala Phe Thr Leu Arg Ile
 65                  70                  75                  80

Ser Arg Val Glu Ala Glu Asp Val Gly Val Tyr Tyr Cys Met Gln His
                 85                  90                  95

Leu Glu Tyr Pro Phe Thr Phe Gly Ala Gly Thr Lys Leu Glu Leu Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 5
<211> LENGTH: 214
<212> TYPE: PRT
<213> ORGANISM: Artificial Sequence
<220> FEATURE:
<223> OTHER INFORMATION: light chain sequence, anti-EGFR chimeric light
      chain (clone C225)

<400> SEQUENCE: 5

Asp Ile Leu Leu Thr Gln Ser Pro Val Ile Leu Ser Val Ser Pro
  1               5                  10                  15

Gly Glu Arg Val Ser Phe Ser Cys Arg Ala Ser Gln Ser Ile Gly
             20                  25                  30

Thr Asn Ile His Trp Tyr Gln Gln Arg Thr Asn Gly Ser Pro Arg
         35                  40                  45

Leu Leu Ile Lys Tyr Ala Ser Glu Ser Ile Ser Gly Ile Pro Ser
     50                  55                  60

Arg Phe Ser Gly Ser Gly Ser Gly Thr Asp Phe Thr Leu Ser Ile
                 65                  70                  75

Asn Ser Val Glu Ser Glu Asp Ile Ala Asp Tyr Tyr Cys Gln Gln
             80                  85                  90

Asn Asn Asn Trp Pro Thr Thr Phe Gly Ala Gly Thr Lys Leu Glu
             95                 100                 105

Leu Lys Arg Thr Val Ala Ala Pro Ser Val Phe Ile Phe Pro Pro
         110                 115                 120

Ser Asp Glu Gln Leu Lys Ser Gly Thr Ala Ser Val Val Cys Leu
             125                 130                 135
```

-continued

```
Leu Asn Asn Phe Tyr Pro Arg Glu Ala Lys Val Gln Trp Lys Val
                140                 145                 150

Asp Asn Ala Leu Gln Ser Gly Asn Ser Gln Glu Ser Val Thr Glu
                155                 160                 165

Gln Asp Ser Lys Asp Ser Thr Tyr Ser Leu Ser Ser Thr Leu Thr
                170                 175                 180

Leu Ser Lys Ala Asp Tyr Glu Lys His Lys Val Tyr Ala Cys Glu
                185                 190                 195

Val Thr His Gln Gly Leu Ser Ser Pro Val Thr Lys Ser Phe Asn
                200                 205                 210

Arg Gly Glu Cys

<210> SEQ ID NO 6
<211> LENGTH: 589
<212> TYPE: PRT
<213> ORGANISM: Artificial Sequence
<220> FEATURE:
<223> OTHER INFORMATION: heavy chain/main chain sequence, FLT3 x CD3;
      bsFcko-1/2 [N-terminal anti-FLT3 chimeric heavy chain (clone 4G8)
      and C-terminal CD3 single-chain (clone UCHT1, VL-VH)] chain of a
      glycan-ko-variant-halfmolecule

<400> SEQUENCE: 6

Gln Val Gln Leu Gln Gln Pro Gly Ala Glu Leu Val Lys Pro Gly
1               5                   10                  15

Ala Ser Leu Lys Leu Ser Cys Lys Ser Ser Gly Tyr Thr Phe Thr
                20                  25                  30

Ser Tyr Trp Met His Trp Val Arg Gln Arg Pro Gly His Gly Leu
                35                  40                  45

Glu Trp Ile Gly Glu Ile Asp Pro Ser Asp Ser Tyr Lys Asp Tyr
                50                  55                  60

Asn Gln Lys Phe Lys Asp Lys Ala Thr Leu Thr Val Asp Arg Ser
                65                  70                  75

Ser Asn Thr Ala Tyr Met His Leu Ser Ser Leu Thr Ser Asp Asp
                80                  85                  90

Ser Ala Val Tyr Tyr Cys Ala Arg Ala Ile Thr Thr Thr Pro Phe
                95                  100                 105

Asp Phe Trp Gly Gln Gly Thr Thr Leu Thr Val Ser Ser Ala Ser
                110                 115                 120

Thr Lys Gly Pro Ser Val Phe Pro Leu Ala Pro Ser Ser Lys Ser
                125                 130                 135

Thr Ser Gly Gly Thr Ala Ala Leu Gly Cys Leu Val Lys Asp Tyr
                140                 145                 150

Phe Pro Glu Pro Val Thr Val Ser Trp Asn Ser Gly Ala Leu Thr
                155                 160                 165

Ser Gly Val His Thr Phe Pro Ala Val Leu Gln Ser Ser Gly Leu
                170                 175                 180

Tyr Ser Leu Ser Ser Val Val Thr Val Pro Ser Ser Ser Leu Gly
                185                 190                 195

Thr Gln Thr Tyr Ile Cys Asn Val Asn His Lys Pro Ser Asn Thr
                200                 205                 210

Lys Val Asp Lys Lys Val Glu Pro Lys Ser Cys Asp Lys Thr His
                215                 220                 225

Thr Ser Pro Pro Ser Pro Ala Pro Pro Val Ala Gly Pro Ser Val
                230                 235                 240
```

Phe Leu Phe Pro Pro Lys Pro Lys Asp Thr Leu Met Ile Ser Arg
245                 250                 255

Thr Pro Glu Val Thr Cys Val Val Val Gly Val Ser His Glu Asp
260                 265                 270

Pro Glu Val Lys Phe Asn Trp Tyr Val Asp Gly Val Glu Val His
275                 280                 285

Asn Ala Lys Thr Lys Pro Arg Glu Glu Gln Tyr Gln Ser Thr Tyr
290                 295                 300

Arg Val Val Ser Val Leu Thr Val Leu His Gln Asp Trp Leu Asn
305                 310                 315

Gly Lys Glu Tyr Lys Cys Lys Val Ser Asn Lys Gln Leu Pro Ser
320                 325                 330

Pro Ile Glu Lys Thr Ile Ser Lys Ala Lys Gly Gln Pro Ser Gly
335                 340                 345

Asp Ile Gln Met Thr Gln Ser Pro Ser Ser Leu Ser Ala Ser Val
350                 355                 360

Gly Asp Arg Val Thr Ile Thr Cys Arg Ala Ser Gln Asp Ile Arg
365                 370                 375

Asn Tyr Leu Asn Trp Tyr Gln Gln Lys Pro Gly Lys Ala Pro Lys
380                 385                 390

Leu Leu Ile Tyr Tyr Thr Ser Arg Leu Glu Ser Gly Val Pro Ser
395                 400                 405

Arg Phe Ser Gly Ser Gly Ser Gly Thr Asp Tyr Thr Leu Thr Ile
410                 415                 420

Ser Ser Leu Gln Pro Glu Asp Phe Ala Thr Tyr Tyr Cys Gln Gln
425                 430                 435

Gly Asn Thr Leu Pro Trp Thr Phe Gly Gln Gly Thr Lys Val Glu
440                 445                 450

Ile Lys Gly Gly Gly Gly Ser Gly Gly Gly Ser Gly Gly Gly Gly
455                 460                 465

Gly Ser Glu Val Gln Leu Val Glu Ser Gly Gly Gly Leu Val Gln
470                 475                 480

Pro Gly Gly Ser Leu Arg Leu Ser Cys Ala Ala Ser Gly Tyr Ser
485                 490                 495

Phe Thr Gly Tyr Thr Met Asn Trp Val Arg Gln Ala Pro Gly Lys
500                 505                 510

Gly Leu Glu Trp Val Ala Leu Ile Asn Pro Tyr Lys Gly Val Ser
515                 520                 525

Thr Tyr Asn Gln Lys Phe Lys Asp Arg Phe Thr Ile Ser Val Asp
530                 535                 540

Lys Ser Lys Asn Thr Ala Tyr Leu Gln Met Asn Ser Leu Arg Ala
545                 550                 555

Glu Asp Thr Ala Val Tyr Tyr Cys Ala Arg Ser Gly Tyr Tyr Gly
560                 565                 570

Asp Ser Asp Trp Tyr Phe Asp Val Trp Gly Gln Gly Thr Leu Val
575                 580                 585

Thr Val Ser Ser

<210> SEQ ID NO 7
<211> LENGTH: 594
<212> TYPE: PRT
<213> ORGANISM: Artificial Sequence
<220> FEATURE:
<223> OTHER INFORMATION: FLT3 x CD3; bsFcko-1/2 [N-terminal anti-FLT3
      chimeric heavy chain (clone BV10) and C-terminal CD3 single-chain (clone UCHT1, VL-VH)], chain of a glycan-ko-variant-halfmolecule

<400> SEQUENCE: 7

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Leu His Trp Val Arg Gln Ser Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Ser Ile Ser Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Arg Lys Gly Gly Ile Tyr Tyr Ala Asn His Tyr Tyr Ala Met Asp Tyr
            100                 105                 110

Trp Gly Gln Gly Thr Ser Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Ser Pro Pro Ser Pro Ala Pro Pro Val
225                 230                 235                 240

Ala Gly Pro Ser Val Phe Leu Phe Pro Pro Lys Pro Lys Asp Thr Leu
                245                 250                 255

Met Ile Ser Arg Thr Pro Glu Val Thr Cys Val Val Val Gly Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Gln Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gln Leu Pro Ser Pro
                325                 330                 335

Ile Glu Lys Thr Ile Ser Lys Ala Lys Gly Gln Pro Ser Gly Asp Ile
            340                 345                 350

Gln Met Thr Gln Ser Pro Ser Ser Leu Ser Ala Ser Val Gly Asp Arg
        355                 360                 365

Val Thr Ile Thr Cys Arg Ala Ser Gln Asp Ile Arg Asn Tyr Leu Asn
    370                 375                 380

Trp Tyr Gln Gln Lys Pro Gly Lys Ala Pro Lys Leu Leu Ile Tyr Tyr
385                 390                 395                 400
```

Thr Ser Arg Leu Glu Ser Gly Val Pro Ser Arg Phe Ser Gly Ser Gly
            405                 410                 415

Ser Gly Thr Asp Tyr Thr Leu Thr Ile Ser Ser Leu Gln Pro Glu Asp
        420                 425                 430

Phe Ala Thr Tyr Tyr Cys Gln Gln Gly Asn Thr Leu Pro Trp Thr Phe
            435                 440                 445

Gly Gln Gly Thr Lys Val Glu Ile Lys Gly Gly Gly Ser Gly Gly
        450                 455                 460

Gly Gly Ser Gly Gly Gly Ser Glu Val Gln Leu Val Glu Ser Gly
465                 470                 475                 480

Gly Gly Leu Val Gln Pro Gly Gly Ser Leu Arg Leu Ser Cys Ala Ala
            485                 490                 495

Ser Gly Tyr Ser Phe Thr Gly Tyr Thr Met Asn Trp Val Arg Gln Ala
            500                 505                 510

Pro Gly Lys Gly Leu Glu Trp Val Ala Leu Ile Asn Pro Tyr Lys Gly
            515                 520                 525

Val Ser Thr Tyr Asn Gln Lys Phe Lys Asp Arg Phe Thr Ile Ser Val
            530                 535                 540

Asp Lys Ser Lys Asn Thr Ala Tyr Leu Gln Met Asn Ser Leu Arg Ala
545                 550                 555                 560

Glu Asp Thr Ala Val Tyr Tyr Cys Ala Arg Ser Gly Tyr Tyr Gly Asp
            565                 570                 575

Ser Asp Trp Tyr Phe Asp Val Trp Gly Gln Gly Thr Leu Val Thr Val
            580                 585                 590

Ser Ser

<210> SEQ ID NO 8
<211> LENGTH: 585
<212> TYPE: PRT
<213> ORGANISM: Artificial Sequence
<220> FEATURE:
<223> OTHER INFORMATION: FLT3 x TCR alpha/beta; bsFcko-1/2 [N-terminal
      anti-FLT3 chimeric heavy chain (clone 4G8) and C-terminal TCR
      alpha/beta single-chain (clone BMA031; VH-VL)], chain of a
      glycan-ko-variant-halfmolecule

<400> SEQUENCE: 8

Gln Val Gln Leu Gln Gln Pro Gly Ala Glu Leu Val Lys Pro Gly Ala
1               5                   10                  15

Ser Leu Lys Leu Ser Cys Lys Ser Ser Gly Tyr Thr Phe Thr Ser Tyr
            20                  25                  30

Trp Met His Trp Val Arg Gln Arg Pro Gly His Gly Leu Glu Trp Ile
        35                  40                  45

Gly Glu Ile Asp Pro Ser Asp Ser Tyr Lys Asp Tyr Asn Gln Lys Phe
    50                  55                  60

Lys Asp Lys Ala Thr Leu Thr Val Asp Arg Ser Ser Asn Thr Ala Tyr
65                  70                  75                  80

Met His Leu Ser Ser Leu Thr Ser Asp Asp Ser Ala Val Tyr Tyr Cys
            85                  90                  95

Ala Arg Ala Ile Thr Thr Thr Pro Phe Asp Phe Trp Gly Gln Gly Thr
            100                 105                 110

Thr Leu Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn

```
              145                 150                 155                 160
Ser Gly Ala Leu Thr Ser Gly Val His Thr Phe Pro Ala Val Leu Gln
              165                 170                 175
Ser Ser Gly Leu Tyr Ser Leu Ser Ser Val Val Thr Val Pro Ser Ser
              180                 185                 190
Ser Leu Gly Thr Gln Thr Tyr Ile Cys Asn Val Asn His Lys Pro Ser
              195                 200                 205
Asn Thr Lys Val Asp Lys Lys Val Glu Pro Lys Ser Cys Asp Lys Thr
              210                 215                 220
His Thr Ser Pro Pro Ser Pro Ala Pro Pro Val Ala Gly Pro Ser Val
225                 230                 235                 240
Phe Leu Phe Pro Pro Lys Pro Lys Asp Thr Leu Met Ile Ser Arg Thr
              245                 250                 255
Pro Glu Val Thr Cys Val Val Val Gly Val Ser His Glu Asp Pro Glu
              260                 265                 270
Val Lys Phe Asn Trp Tyr Val Asp Gly Val Glu Val His Asn Ala Lys
              275                 280                 285
Thr Lys Pro Arg Glu Glu Gln Tyr Gln Ser Thr Tyr Arg Val Val Ser
              290                 295                 300
Val Leu Thr Val Leu His Gln Asp Trp Leu Asn Gly Lys Glu Tyr Lys
305                 310                 315                 320
Cys Lys Val Ser Asn Lys Gln Leu Pro Ser Pro Ile Glu Lys Thr Ile
              325                 330                 335
Ser Lys Ala Lys Gly Gln Pro Ser Gly Glu Val Gln Leu Gln Gln Ser
              340                 345                 350
Gly Pro Glu Leu Val Lys Pro Gly Ala Ser Val Lys Met Ser Cys Lys
              355                 360                 365
Ala Ser Gly Tyr Lys Phe Thr Ser Tyr Val Met His Trp Val Lys Gln
              370                 375                 380
Lys Pro Gly Gln Gly Leu Glu Trp Ile Gly Tyr Ile Asn Pro Tyr Asn
385                 390                 395                 400
Asp Val Thr Lys Tyr Asn Glu Lys Phe Lys Gly Lys Ala Thr Leu Thr
              405                 410                 415
Ser Asp Lys Ser Ser Thr Ala Tyr Met Glu Leu Ser Ser Leu Thr
              420                 425                 430
Ser Glu Asp Ser Ala Val His Tyr Cys Ala Arg Gly Ser Tyr Tyr Asp
              435                 440                 445
Tyr Asp Gly Phe Val Tyr Gly Gln Gly Thr Leu Val Thr Val Ser Ser
              450                 455                 460
Gly Gly Gly Gly Ser Gly Gly Gly Ser Gly Gly Gly Gly Ser Gln
465                 470                 475                 480
Ile Val Leu Thr Gln Ser Pro Ala Ile Met Ser Ala Ser Pro Gly Glu
              485                 490                 495
Lys Val Thr Met Thr Cys Ser Ala Thr Ser Ser Val Ser Tyr Met His
              500                 505                 510
Trp Tyr Gln Gln Lys Ser Gly Thr Ser Pro Lys Arg Trp Ile Tyr Asp
              515                 520                 525
Thr Ser Lys Leu Ala Ser Gly Val Pro Ala Arg Phe Ser Gly Ser Gly
              530                 535                 540
Ser Gly Thr Ser Tyr Ser Leu Thr Ile Ser Ser Met Glu Ala Glu Asp
545                 550                 555                 560
Ala Ala Thr Tyr Tyr Cys Gln Gln Trp Ser Ser Asn Pro Leu Thr Phe
              565                 570                 575
```

Gly Ala Gly Thr Lys Leu Glu Leu Lys
            580                 585

<210> SEQ ID NO 9
<211> LENGTH: 590
<212> TYPE: PRT
<213> ORGANISM: Artificial Sequence
<220> FEATURE:
<223> OTHER INFORMATION: FLT3 x TCR alpha/beta; bsFcko-1/2 [N-terminal
      anti-FLT3 chimeric heavy chain (clone BV10) and C-terminal TCR
      alpha/beta single-chain (clone BMA031; VH-VL)], chain of a
      glycan-ko-variant-halfmolecule

<400> SEQUENCE: 9

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Leu His Trp Val Arg Gln Ser Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Ser Ile Ser Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Arg Lys Gly Gly Ile Tyr Tyr Ala Asn His Tyr Tyr Ala Met Asp Tyr
            100                 105                 110

Trp Gly Gln Gly Thr Ser Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Ser Pro Pro Ser Pro Ala Pro Pro Val
225                 230                 235                 240

Ala Gly Pro Ser Val Phe Leu Phe Pro Pro Lys Pro Lys Asp Thr Leu
                245                 250                 255

Met Ile Ser Arg Thr Pro Glu Val Thr Cys Val Val Val Gly Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Gln Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gln Leu Pro Ser Pro
                325                 330                 335

```
Ile Glu Lys Thr Ile Ser Lys Ala Lys Gly Gln Pro Ser Gly Glu Val
            340                 345                 350

Gln Leu Gln Gln Ser Gly Pro Glu Leu Val Lys Pro Gly Ala Ser Val
            355                 360                 365

Lys Met Ser Cys Lys Ala Ser Gly Tyr Lys Phe Thr Ser Tyr Val Met
370                 375                 380

His Trp Val Lys Gln Lys Pro Gly Gln Gly Leu Glu Trp Ile Gly Tyr
385                 390                 395                 400

Ile Asn Pro Tyr Asn Asp Val Thr Lys Tyr Asn Glu Lys Phe Lys Gly
                405                 410                 415

Lys Ala Thr Leu Thr Ser Asp Lys Ser Ser Thr Ala Tyr Met Glu
            420                 425                 430

Leu Ser Ser Leu Thr Ser Glu Asp Ser Ala Val His Tyr Cys Ala Arg
            435                 440                 445

Gly Ser Tyr Tyr Asp Tyr Asp Gly Phe Val Tyr Gly Gln Gly Thr Leu
            450                 455                 460

Val Thr Val Ser Ser Gly Gly Gly Gly Ser Gly Gly Gly Gly Ser Gly
465                 470                 475                 480

Gly Gly Gly Ser Gln Ile Val Leu Thr Gln Ser Pro Ala Ile Met Ser
            485                 490                 495

Ala Ser Pro Gly Glu Lys Val Thr Met Thr Cys Ser Ala Thr Ser Ser
            500                 505                 510

Val Ser Tyr Met His Trp Tyr Gln Gln Lys Ser Gly Thr Ser Pro Lys
            515                 520                 525

Arg Trp Ile Tyr Asp Thr Ser Lys Leu Ala Ser Gly Val Pro Ala Arg
            530                 535                 540

Phe Ser Gly Ser Gly Ser Gly Thr Ser Tyr Ser Leu Thr Ile Ser Ser
545                 550                 555                 560

Met Glu Ala Glu Asp Ala Ala Thr Tyr Tyr Cys Gln Gln Trp Ser Ser
                565                 570                 575

Asn Pro Leu Thr Phe Gly Ala Gly Thr Lys Leu Glu Leu Lys
            580                 585                 590

<210> SEQ ID NO 10
<211> LENGTH: 592
<212> TYPE: PRT
<213> ORGANISM: Artificial Sequence
<220> FEATURE:
<223> OTHER INFORMATION: FLT3 x CD28; bsFcko-1/2 [N-terminal anti-FLT3
      chimeric heavy chain (clone 4G8) and C-terminal CD28 single-chain
      (clone 9.3; VL-VH)], being a chain of a glycan-ko-variant-
      halfmolecule

<400> SEQUENCE: 10

Gln Val Gln Leu Gln Gln Pro Gly Ala Glu Leu Val Lys Pro Gly Ala
1               5                   10                  15

Ser Leu Lys Leu Ser Cys Lys Ser Ser Gly Tyr Thr Phe Thr Ser Tyr
            20                  25                  30

Trp Met His Trp Val Arg Gln Arg Pro Gly His Gly Leu Glu Trp Ile
        35                  40                  45

Gly Glu Ile Asp Pro Ser Asp Ser Tyr Lys Asp Tyr Asn Gln Lys Phe
    50                  55                  60

Lys Asp Lys Ala Thr Leu Thr Val Asp Arg Ser Ser Asn Thr Ala Tyr
65                  70                  75                  80

Met His Leu Ser Ser Leu Thr Ser Asp Asp Ser Ala Val Tyr Tyr Cys
                85                  90                  95
```

```
Ala Arg Ala Ile Thr Thr Thr Pro Phe Asp Phe Trp Gly Gln Gly Thr
            100                 105                 110

Thr Leu Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
            210                 215                 220

His Thr Ser Pro Pro Ser Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Gly Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Gln Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Gln Leu Pro Ser Pro Ile Glu Lys Thr Ile
                325                 330                 335

Ser Lys Ala Lys Gly Gln Pro Ser Gly Asp Ile Glu Leu Thr Gln Ser
            340                 345                 350

Pro Ala Ser Leu Ala Val Ser Leu Gly Gln Arg Ala Thr Ile Ser Cys
            355                 360                 365

Arg Ala Ser Glu Ser Val Glu Tyr Tyr Val Thr Ser Leu Met Gln Trp
            370                 375                 380

Tyr Gln Gln Lys Pro Gly Gln Pro Pro Lys Leu Leu Ile Phe Ala Ala
385                 390                 395                 400

Ser Asn Val Glu Ser Gly Val Pro Ala Arg Phe Ser Gly Ser Gly Ser
                405                 410                 415

Gly Thr Asn Phe Ser Leu Asn Ile His Pro Val Asp Glu Asp Asp Val
            420                 425                 430

Ala Met Tyr Phe Cys Gln Gln Ser Arg Lys Val Pro Tyr Thr Phe Gly
            435                 440                 445

Gly Gly Thr Lys Leu Glu Ile Lys Arg Gly Gly Gly Gly Ser Gly Gly
            450                 455                 460

Gly Gly Ser Gly Gly Gly Gly Ser Gln Val Lys Leu Gln Gln Ser Gly
465                 470                 475                 480

Pro Gly Leu Val Thr Pro Ser Gln Ser Leu Ser Ile Thr Cys Thr Val
                485                 490                 495

Ser Gly Phe Ser Leu Ser Asp Tyr Gly Val His Trp Val Arg Gln Ser
            500                 505                 510
```

Pro Gly Gln Gly Leu Glu Trp Leu Gly Val Ile Trp Ala Gly Gly Gly
            515                 520                 525

Thr Asn Tyr Asn Ser Ala Leu Met Ser Arg Lys Ser Ile Ser Lys Asp
        530                 535                 540

Asn Ser Lys Ser Gln Val Phe Leu Lys Met Asn Ser Leu Gln Ala Asp
545                 550                 555                 560

Asp Thr Ala Val Tyr Tyr Cys Ala Arg Asp Lys Gly Tyr Ser Tyr Tyr
                565                 570                 575

Tyr Ser Met Asp Tyr Trp Gly Gln Gly Thr Thr Val Thr Val Ser Ser
            580                 585                 590

<210> SEQ ID NO 11
<211> LENGTH: 597
<212> TYPE: PRT
<213> ORGANISM: Artificial Sequence
<220> FEATURE:
<223> OTHER INFORMATION: FLT3 x CD28; bsFcko-1/2 [N-terminal anti-FLT3
      chimeric heavy chain (clone BV10) and C-terminal CD28 single-chain
      (clone 9.3, VL-VH)], chain of a glycan-ko-variant-halfmolecule

<400> SEQUENCE: 11

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Leu His Trp Val Arg Gln Ser Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Ser Ile Ser Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Arg Lys Gly Gly Ile Tyr Tyr Ala Asn His Tyr Tyr Ala Met Asp Tyr
            100                 105                 110

Trp Gly Gln Gly Thr Ser Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Val Glu Pro Lys
    210                 215                 220

Ser Cys Asp Lys Thr His Thr Ser Pro Pro Ser Pro Ala Pro Pro Val
225                 230                 235                 240

Ala Gly Pro Ser Val Phe Leu Phe Pro Pro Lys Pro Lys Asp Thr Leu
                245                 250                 255

Met Ile Ser Arg Thr Pro Glu Val Thr Cys Val Val Val Gly Val Ser
            260                 265                 270

His Glu Asp Pro Glu Val Lys Phe Asn Trp Tyr Val Asp Gly Val Glu 275                 280                 285
Val His Asn Ala Lys Thr Lys Pro Arg Glu Glu Gln Tyr Gln Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gln Leu Pro Ser Pro
                325                 330                 335

Ile Glu Lys Thr Ile Ser Lys Ala Lys Gly Gln Pro Ser Gly Asp Ile
            340                 345                 350

Glu Leu Thr Gln Ser Pro Ala Ser Leu Ala Val Ser Leu Gly Gln Arg
        355                 360                 365

Ala Thr Ile Ser Cys Arg Ala Ser Glu Ser Val Glu Tyr Tyr Val Thr
    370                 375                 380

Ser Leu Met Gln Trp Tyr Gln Gln Lys Pro Gly Gln Pro Pro Lys Leu
385                 390                 395                 400

Leu Ile Phe Ala Ala Ser Asn Val Glu Ser Gly Val Pro Ala Arg Phe
                405                 410                 415

Ser Gly Ser Gly Ser Gly Thr Asn Phe Ser Leu Asn Ile His Pro Val
            420                 425                 430

Asp Glu Asp Asp Val Ala Met Tyr Phe Cys Gln Gln Ser Arg Lys Val
        435                 440                 445

Pro Tyr Thr Phe Gly Gly Gly Thr Lys Leu Glu Ile Lys Arg Gly Gly
    450                 455                 460

Gly Gly Ser Gly Gly Gly Gly Ser Gly Gly Gly Gly Ser Gln Val Lys
465                 470                 475                 480

Leu Gln Gln Ser Gly Pro Gly Leu Val Thr Pro Ser Gln Ser Leu Ser
                485                 490                 495

Ile Thr Cys Thr Val Ser Gly Phe Ser Leu Ser Asp Tyr Gly Val His
            500                 505                 510

Trp Val Arg Gln Ser Pro Gly Gln Gly Leu Glu Trp Leu Gly Val Ile
        515                 520                 525

Trp Ala Gly Gly Gly Thr Asn Tyr Asn Ser Ala Leu Met Ser Arg Lys
    530                 535                 540

Ser Ile Ser Lys Asp Asn Ser Lys Ser Gln Val Phe Leu Lys Met Asn
545                 550                 555                 560

Ser Leu Gln Ala Asp Asp Thr Ala Val Tyr Tyr Cys Ala Arg Asp Lys
                565                 570                 575

Gly Tyr Ser Tyr Tyr Tyr Ser Met Asp Tyr Trp Gly Gln Gly Thr Thr
            580                 585                 590

Val Thr Val Ser Ser
        595

<210> SEQ ID NO 12
<211> LENGTH: 589
<212> TYPE: PRT
<213> ORGANISM: Artificial Sequence
<220> FEATURE:
<223> OTHER INFORMATION: FLT3 x CD16; bsFcko-1/2 [N-terminal anti-FLT3
      chimeric heavy chain (clone 4G8) and C-terminal CD16 single-chain
      (clone 3G8; VL-VH)], being a chain of a glycan-ko-variant-
      halfmolecule

<400> SEQUENCE: 12

Gln Val Gln Leu Gln Gln Pro Gly Ala Glu Leu Val Lys Pro Gly Ala
1               5                   10                  15

Ser Leu Lys Leu Ser Cys Lys Ser Ser Gly Tyr Thr Phe Thr Ser Tyr

```
                    20                  25                  30
Trp Met His Trp Val Arg Gln Arg Pro Gly His Gly Leu Glu Trp Ile
                35                  40                  45
Gly Glu Ile Asp Pro Ser Asp Ser Tyr Lys Asp Tyr Asn Gln Lys Phe
            50                  55                  60
Lys Asp Lys Ala Thr Leu Thr Val Asp Arg Ser Ser Asn Thr Ala Tyr
65                  70                  75                  80
Met His Leu Ser Ser Leu Thr Ser Asp Asp Ser Ala Val Tyr Tyr Cys
                85                  90                  95
Ala Arg Ala Ile Thr Thr Thr Pro Phe Asp Phe Trp Gly Gln Gly Thr
                100                 105                 110
Thr Leu Thr Val Ser Ser Ala Ser Thr Lys Gly Pro Ser Val Phe Pro
            115                 120                 125
Leu Ala Pro Ser Ser Lys Ser Thr Ser Gly Gly Thr Ala Ala Leu Gly
            130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
            195                 200                 205
Asn Thr Lys Val Asp Lys Lys Val Glu Pro Lys Ser Cys Asp Lys Thr
    210                 215                 220
His Thr Ser Pro Pro Ser Pro Ala Pro Pro Val Ala Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Gly Val Ser His Glu Asp Pro Glu
            260                 265                 270
Val Lys Phe Asn Trp Tyr Val Asp Gly Val Glu Val His Asn Ala Lys
            275                 280                 285
Thr Lys Pro Arg Glu Glu Gln Tyr Gln Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Gln Leu Pro Ser Pro Ile Glu Lys Thr Ile
                325                 330                 335
Ser Lys Ala Lys Gly Gln Pro Ser Gly Asp Ile Val Leu Thr Gln Ser
            340                 345                 350
Pro Ala Ser Leu Ala Val Ser Leu Gly Gln Arg Ala Thr Ile Ser Cys
            355                 360                 365
Lys Ala Ser Gln Ser Val Asp Phe Asp Gly Asp Ser Phe Met Asn Trp
    370                 375                 380
Tyr Gln Gln Lys Pro Gly Gln Pro Pro Lys Leu Leu Ile Tyr Thr Thr
385                 390                 395                 400
Ser Asn Leu Glu Ser Gly Ile Pro Ala Arg Phe Ser Ala Ser Gly Ser
                405                 410                 415
Gly Thr Asp Phe Thr Leu Asn Ile His Pro Val Glu Glu Asp Thr
            420                 425                 430
Ala Thr Tyr Tyr Cys Gln Gln Ser Asn Glu Asp Pro Tyr Thr Phe Gly
            435                 440                 445
```

```
Gly Gly Thr Lys Leu Glu Ile Lys Gly Gly Gly Ser Gly Gly Gly
            450                 455                 460

Gly Ser Gly Gly Gly Ser Gln Val Thr Leu Lys Glu Ser Gly Pro
465                 470                 475                 480

Gly Ile Leu Gln Pro Ser Gln Thr Leu Ser Leu Thr Cys Ser Phe Ser
                485                 490                 495

Gly Phe Ser Leu Arg Thr Ser Gly Met Gly Val Gly Trp Ile Arg Gln
                500                 505                 510

Pro Ser Gly Lys Gly Leu Glu Trp Leu Ala His Ile Trp Trp Asp Asp
                515                 520                 525

Asp Lys Arg Tyr Asn Pro Ala Leu Lys Ser Arg Leu Thr Ile Ser Lys
                530                 535                 540

Asp Thr Ser Ser Asn Gln Val Phe Leu Lys Ile Ala Ser Val Asp Thr
545                 550                 555                 560

Ala Asp Thr Ala Thr Tyr Tyr Cys Ala Gln Ile Asn Pro Ala Trp Phe
                565                 570                 575

Ala Tyr Trp Gly Gln Gly Thr Leu Val Thr Val Ser Ser
                580                 585

<210> SEQ ID NO 13
<211> LENGTH: 594
<212> TYPE: PRT
<213> ORGANISM: Artificial Sequence
<220> FEATURE:
<223> OTHER INFORMATION: FLT3 x CD16; bsFcko-1/2 [N-terminal anti-FLT3
      chimeric heavy chain (clone BV10) and C-terminal CD16 single-chain
      (clone 3G8; VL-VH)], being a chain of a glycan-ko-variant-
      halfmolecule

<400> SEQUENCE: 13

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Leu His Trp Val Arg Gln Ser Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Ser Ile Ser Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Arg Lys Gly Gly Ile Tyr Tyr Ala Asn His Tyr Tyr Ala Met Asp Tyr
            100                 105                 110

Trp Gly Gln Gly Thr Ser Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205
```

```
Asn His Lys Pro Ser Asn Thr Lys Val Asp Lys Lys Val Glu Pro Lys
            210                 215                 220

Ser Cys Asp Lys Thr His Thr Ser Pro Pro Ser Ala Pro Pro Val
225                 230                 235                 240

Ala Gly Pro Ser Val Phe Leu Phe Pro Pro Lys Pro Lys Asp Thr Leu
                245                 250                 255

Met Ile Ser Arg Thr Pro Glu Val Thr Cys Val Val Val Gly Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Gln Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gln Leu Pro Ser Pro
                325                 330                 335

Ile Glu Lys Thr Ile Ser Lys Ala Lys Gly Gln Pro Ser Gly Asp Ile
            340                 345                 350

Val Leu Thr Gln Ser Pro Ala Ser Leu Ala Val Ser Leu Gly Gln Arg
        355                 360                 365

Ala Thr Ile Ser Cys Lys Ala Ser Gln Ser Val Asp Phe Asp Gly Asp
    370                 375                 380

Ser Phe Met Asn Trp Tyr Gln Gln Lys Pro Gly Gln Pro Pro Lys Leu
385                 390                 395                 400

Leu Ile Tyr Thr Thr Ser Asn Leu Glu Ser Gly Ile Pro Ala Arg Phe
                405                 410                 415

Ser Ala Ser Gly Ser Gly Thr Asp Phe Thr Leu Asn Ile His Pro Val
            420                 425                 430

Glu Glu Glu Asp Thr Ala Thr Tyr Tyr Cys Gln Gln Ser Asn Glu Asp
        435                 440                 445

Pro Tyr Thr Phe Gly Gly Gly Thr Lys Leu Glu Ile Lys Gly Gly Gly
    450                 455                 460

Gly Ser Gly Gly Gly Gly Ser Gly Gly Gly Gly Ser Gln Val Thr Leu
465                 470                 475                 480

Lys Glu Ser Gly Pro Gly Ile Leu Gln Pro Ser Gln Thr Leu Ser Leu
                485                 490                 495

Thr Cys Ser Phe Ser Gly Phe Ser Leu Arg Thr Ser Gly Met Gly Val
            500                 505                 510

Gly Trp Ile Arg Gln Pro Ser Gly Lys Gly Leu Glu Trp Leu Ala His
        515                 520                 525

Ile Trp Trp Asp Asp Lys Arg Tyr Asn Pro Ala Leu Lys Ser Arg
    530                 535                 540

Leu Thr Ile Ser Lys Asp Thr Ser Asn Gln Val Phe Leu Lys Ile
545                 550                 555                 560

Ala Ser Val Asp Thr Ala Asp Thr Ala Thr Tyr Tyr Cys Ala Gln Ile
                565                 570                 575

Asn Pro Ala Trp Phe Ala Tyr Trp Gly Gln Gly Thr Leu Val Thr Val
            580                 585                 590

Ser Ser

<210> SEQ ID NO 14
<211> LENGTH: 592
<212> TYPE: PRT
```

<213> ORGANISM: Artificial Sequence
<220> FEATURE:
<223> OTHER INFORMATION: CD19 x CD3, bsFcko-1/2 [N-terminal anti-CD19 chimeric heavy chain (clone 4G7) and C-terminal anti-CD3 single-chain (clone UCHT1; VL-VH)], chain of a glycan-ko-variant-halfmolecule

<400> SEQUENCE: 14

```
Glu Val Gln Leu Gln Gln Ser Gly Pro Glu Leu Ile Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Thr Tyr Tyr Tyr Gly Ser Arg Val Phe Asp Tyr Trp Gly
            100                 105                 110

Gln Gly Thr Thr Leu Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Ser Pro Pro Ser Pro Ala Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Gly Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Gln Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gln Leu Pro Ser Pro Ile Glu
                325                 330                 335

Lys Thr Ile Ser Lys Ala Lys Gly Gln Pro Ser Gly Asp Ile Gln Met
            340                 345                 350

Thr Gln Ser Pro Ser Ser Leu Ser Ala Ser Val Gly Asp Arg Val Thr
        355                 360                 365

Ile Thr Cys Arg Ala Ser Gln Asp Ile Arg Asn Tyr Leu Asn Trp Tyr
```

```
            370                 375                 380
Gln Gln Lys Pro Gly Lys Ala Pro Lys Leu Leu Ile Tyr Tyr Thr Ser
385                 390                 395                 400

Arg Leu Glu Ser Gly Val Pro Ser Arg Phe Ser Gly Ser Gly Ser Gly
                405                 410                 415

Thr Asp Tyr Thr Leu Thr Ile Ser Ser Leu Gln Pro Glu Asp Phe Ala
            420                 425                 430

Thr Tyr Tyr Cys Gln Gln Gly Asn Thr Leu Pro Trp Thr Phe Gly Gln
            435                 440                 445

Gly Thr Lys Val Glu Ile Lys Gly Gly Gly Ser Gly Gly Gly Gly
        450                 455                 460

Ser Gly Gly Gly Gly Ser Glu Val Gln Leu Val Glu Ser Gly Gly
465                 470                 475                 480

Leu Val Gln Pro Gly Gly Ser Leu Arg Leu Ser Cys Ala Ala Ser Gly
                485                 490                 495

Tyr Ser Phe Thr Gly Tyr Thr Met Asn Trp Val Arg Gln Ala Pro Gly
            500                 505                 510

Lys Gly Leu Glu Trp Val Ala Leu Ile Asn Pro Tyr Lys Gly Val Ser
        515                 520                 525

Thr Tyr Asn Gln Lys Phe Lys Asp Arg Phe Thr Ile Ser Val Asp Lys
530                 535                 540

Ser Lys Asn Thr Ala Tyr Leu Gln Met Asn Ser Leu Arg Ala Glu Asp
545                 550                 555                 560

Thr Ala Val Tyr Tyr Cys Ala Arg Ser Gly Tyr Tyr Gly Asp Ser Asp
                565                 570                 575

Trp Tyr Phe Asp Val Trp Gly Gln Gly Thr Leu Val Thr Val Ser Ser
            580                 585                 590

<210> SEQ ID NO 15
<211> LENGTH: 588
<212> TYPE: PRT
<213> ORGANISM: Artificial Sequence
<220> FEATURE:
<223> OTHER INFORMATION: CD19 x TCR alpha/beta, bsFcko-1/2 [N-terminal
      anti-CD19 chimeric heavy chain (clone 4G7) and C-terminal anti-TCR
      alpha/beta single-chain (clone BMA031; VH-VL)]: being a chain of a
      glycan-ko-variant-halfmolecule

<400> SEQUENCE: 15

Glu Val Gln Leu Gln Gln Ser Gly Pro Glu Leu Ile Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Thr Tyr Tyr Tyr Gly Ser Arg Val Phe Asp Tyr Trp Gly
            100                 105                 110

Gln Gly Thr Thr Leu Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
```

```
                130             135             140
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Cys
            210                 215                 220

Asp Lys Thr His Thr Ser Pro Pro Ser Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Gly Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Gln Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gln Leu Pro Ser Pro Ile Glu
                325                 330                 335

Lys Thr Ile Ser Lys Ala Lys Gly Gln Pro Ser Gly Glu Val Gln Leu
                340                 345                 350

Gln Gln Ser Gly Pro Glu Leu Val Lys Pro Gly Ala Ser Val Lys Met
            355                 360                 365

Ser Cys Lys Ala Ser Gly Tyr Lys Phe Thr Ser Tyr Val Met His Trp
            370                 375                 380

Val Lys Gln Lys Pro Gly Gln Gly Leu Glu Trp Ile Gly Tyr Ile Asn
385                 390                 395                 400

Pro Tyr Asn Asp Val Thr Lys Tyr Asn Glu Lys Phe Lys Gly Lys Ala
                405                 410                 415

Thr Leu Thr Ser Asp Lys Ser Ser Thr Ala Tyr Met Glu Leu Ser
                420                 425                 430

Ser Leu Thr Ser Glu Asp Ser Ala Val His Tyr Cys Ala Arg Gly Ser
            435                 440                 445

Tyr Tyr Asp Tyr Asp Gly Phe Val Tyr Gly Gln Gly Thr Leu Val Thr
            450                 455                 460

Val Ser Ser Gly Gly Gly Gly Ser Gly Gly Gly Gly Ser Gly Gly Gly
465                 470                 475                 480

Gly Ser Gln Ile Val Leu Thr Gln Ser Pro Ala Ile Met Ser Ala Ser
                485                 490                 495

Pro Gly Glu Lys Val Thr Met Thr Cys Ser Ala Thr Ser Ser Val Ser
                500                 505                 510

Tyr Met His Trp Tyr Gln Gln Lys Ser Gly Thr Ser Pro Lys Arg Trp
            515                 520                 525

Ile Tyr Asp Thr Ser Lys Leu Ala Ser Gly Val Pro Ala Arg Phe Ser
            530                 535                 540

Gly Ser Gly Ser Gly Thr Ser Tyr Ser Leu Thr Ile Ser Ser Met Glu
545                 550                 555                 560
```

Ala Glu Asp Ala Ala Thr Tyr Tyr Cys Gln Gln Trp Ser Ser Asn Pro
            565                 570                 575

Leu Thr Phe Gly Ala Gly Thr Lys Leu Glu Leu Lys
            580                 585

<210> SEQ ID NO 16
<211> LENGTH: 595
<212> TYPE: PRT
<213> ORGANISM: Artificial Sequence
<220> FEATURE:
<223> OTHER INFORMATION: CD19 x CD28; bsFcko-1/2 [N-terminal anti-CD19
      chimeric heavy chain (clone 4G7) and C-terminal CD28 single-chain
      (clone 9.3; VL-VH)],chain of a glycan-ko-variant-halfmolecule

<400> SEQUENCE: 16

Glu Val Gln Leu Gln Gln Ser Gly Pro Glu Leu Ile Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Thr Tyr Tyr Gly Ser Arg Val Phe Asp Tyr Trp Gly
            100                 105                 110

Gln Gly Thr Thr Leu Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Ser Pro Pro Ser Pro Ala Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Gly Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Gln Ser Thr Tyr Arg
    290                 295                 300

Val Val Ser Val Leu Thr Val Leu His Gln Asp Trp Leu Asn Gly Lys
305                 310                 315                 320

```
Glu Tyr Lys Cys Lys Val Ser Asn Lys Gln Leu Pro Ser Pro Ile Glu
            325                 330                 335

Lys Thr Ile Ser Lys Ala Lys Gly Gln Pro Ser Gly Asp Ile Glu Leu
        340                 345                 350

Thr Gln Ser Pro Ala Ser Leu Ala Val Ser Leu Gly Gln Arg Ala Thr
    355                 360                 365

Ile Ser Cys Arg Ala Ser Glu Ser Val Glu Tyr Tyr Val Thr Ser Leu
370                 375                 380

Met Gln Trp Tyr Gln Gln Lys Pro Gly Gln Pro Pro Lys Leu Leu Ile
385                 390                 395                 400

Phe Ala Ala Ser Asn Val Glu Ser Gly Val Pro Ala Arg Phe Ser Gly
                405                 410                 415

Ser Gly Ser Gly Thr Asn Phe Ser Leu Asn Ile His Pro Val Asp Glu
            420                 425                 430

Asp Asp Val Ala Met Tyr Phe Cys Gln Gln Ser Arg Lys Val Pro Tyr
        435                 440                 445

Thr Phe Gly Gly Gly Thr Lys Leu Glu Ile Lys Arg Gly Gly Gly Gly
    450                 455                 460

Ser Gly Gly Gly Gly Ser Gly Gly Gly Gly Ser Gln Val Lys Leu Gln
465                 470                 475                 480

Gln Ser Gly Pro Gly Leu Val Thr Pro Ser Gln Ser Leu Ser Ile Thr
                485                 490                 495

Cys Thr Val Ser Gly Phe Ser Leu Ser Asp Tyr Gly Val His Trp Val
            500                 505                 510

Arg Gln Ser Pro Gly Gln Gly Leu Glu Trp Leu Gly Val Ile Trp Ala
        515                 520                 525

Gly Gly Gly Thr Asn Tyr Asn Ser Ala Leu Met Ser Arg Lys Ser Ile
    530                 535                 540

Ser Lys Asp Asn Ser Lys Ser Gln Val Phe Leu Lys Met Asn Ser Leu
545                 550                 555                 560

Gln Ala Asp Asp Thr Ala Val Tyr Tyr Cys Ala Arg Asp Lys Gly Tyr
                565                 570                 575

Ser Tyr Tyr Tyr Ser Met Asp Tyr Trp Gly Gln Gly Thr Thr Val Thr
            580                 585                 590

Val Ser Ser
        595

<210> SEQ ID NO 17
<211> LENGTH: 592
<212> TYPE: PRT
<213> ORGANISM: Artificial Sequence
<220> FEATURE:
<223> OTHER INFORMATION: CD19 x CD16; bsFcko-1/2 [N-terminal anti-CD19
      chimeric heavy chain (clone 4G7) and C-terminal CD16 single-chain
      (clone 3G8; VL-VH)], chain of a glycan-ko-variant-halfmolecule

<400> SEQUENCE: 17

Glu Val Gln Leu Gln Gln Ser Gly Pro Glu Leu Ile Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
```

-continued

```
            65                  70                  75                  80
Met Glu Leu Ser Ser Leu Thr Ser Glu Asp Ser Ala Val Tyr Tyr Cys
                    85                  90                  95

Ala Arg Gly Thr Tyr Tyr Gly Ser Arg Val Phe Asp Tyr Trp Gly
                100                 105                 110

Gln Gly Thr Thr Leu Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Cys
            210                 215                 220

Asp Lys Thr His Thr Ser Pro Pro Ser Pro Ala Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Gly Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Gln Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gln Leu Pro Ser Pro Ile Glu
                325                 330                 335

Lys Thr Ile Ser Lys Ala Lys Gly Gln Pro Ser Gly Asp Ile Val Leu
                340                 345                 350

Thr Gln Ser Pro Ala Ser Leu Ala Val Ser Leu Gly Gln Arg Ala Thr
                355                 360                 365

Ile Ser Cys Lys Ala Ser Gln Ser Val Asp Phe Asp Gly Asp Ser Phe
            370                 375                 380

Met Asn Trp Tyr Gln Gln Lys Pro Gly Gln Pro Lys Leu Leu Ile
385                 390                 395                 400

Tyr Thr Thr Ser Asn Leu Glu Ser Gly Ile Pro Ala Arg Phe Ser Ala
                405                 410                 415

Ser Gly Ser Gly Thr Asp Phe Thr Leu Asn Ile His Pro Val Glu Glu
                420                 425                 430

Glu Asp Thr Ala Thr Tyr Tyr Cys Gln Gln Ser Asn Glu Asp Pro Tyr
            435                 440                 445

Thr Phe Gly Gly Gly Thr Lys Leu Glu Ile Lys Gly Gly Gly Gly Ser
            450                 455                 460

Gly Gly Gly Gly Ser Gly Gly Gly Ser Gln Val Thr Leu Lys Glu
465                 470                 475                 480

Ser Gly Pro Gly Ile Leu Gln Pro Ser Gln Thr Leu Ser Leu Thr Cys
                485                 490                 495
```

-continued

```
Ser Phe Ser Gly Phe Ser Leu Arg Thr Ser Gly Met Gly Val Gly Trp
            500                 505                 510

Ile Arg Gln Pro Ser Gly Lys Gly Leu Glu Trp Leu Ala His Ile Trp
            515                 520                 525

Trp Asp Asp Lys Arg Tyr Asn Pro Ala Leu Lys Ser Arg Leu Thr
530                 535                 540

Ile Ser Lys Asp Thr Ser Ser Asn Gln Val Phe Leu Lys Ile Ala Ser
545                 550                 555                 560

Val Asp Thr Ala Asp Thr Ala Thr Tyr Tyr Cys Ala Gln Ile Asn Pro
                565                 570                 575

Ala Trp Phe Ala Tyr Trp Gly Gln Gly Thr Leu Val Thr Val Ser Ser
            580                 585                 590
```

<210> SEQ ID NO 18
<211> LENGTH: 592
<212> TYPE: PRT
<213> ORGANISM: Artificial Sequence
<220> FEATURE:
<223> OTHER INFORMATION: CSPG4 x CD3, bsFcko-1/2 [N-terminal anti-CSPG4 chimeric heavy chain (clone 9.2.27) and C-terminal anti-CD3 single-chain (clone UCHT1; VL-VH)], a chain of a glycan-ko-variant-halfmolecule

<400> SEQUENCE: 18

```
Gln Val Lys Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Arg Ser
            20                  25                  30

Trp Met Asn Trp Val Lys Gln Arg Pro Gly Gln Gly Leu Glu Trp Ile
            35                  40                  45

Gly Arg Ile Tyr Pro Gly Asp Gly Asp Thr Asn Tyr Asn Gly Lys Phe
        50                  55                  60

Lys Gly Lys Ala Thr Leu Thr Ala Asp Lys Ser Ser Ser Thr Ala Tyr
65                  70                  75                  80

Met Gln Val Ser Ser Leu Thr Ser Val Asp Ser Ala Val Tyr Phe Cys
            85                  90                  95

Ala Arg Gly Asn Thr Val Val Pro Tyr Thr Met Asp Tyr Trp Gly
            100                 105                 110

Gln Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Val Glu Pro Lys Ser Cys
        210                 215                 220

Asp Lys Thr His Thr Ser Pro Pro Ser Pro Ala Pro Val Ala Gly
225                 230                 235                 240

Pro Ser Val Phe Leu Phe Pro Pro Lys Pro Lys Asp Thr Leu Met Ile
            245                 250                 255
```

Ser Arg Thr Pro Glu Val Thr Cys Val Val Val Gly Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Gln Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gln Leu Pro Ser Pro Ile Glu
                325                 330                 335

Lys Thr Ile Ser Lys Ala Lys Gly Gln Pro Ser Gly Asp Ile Gln Met
            340                 345                 350

Thr Gln Ser Pro Ser Ser Leu Ser Ala Ser Val Gly Asp Arg Val Thr
        355                 360                 365

Ile Thr Cys Arg Ala Ser Gln Asp Ile Arg Asn Tyr Leu Asn Trp Tyr
    370                 375                 380

Gln Gln Lys Pro Gly Lys Ala Pro Lys Leu Leu Ile Tyr Tyr Thr Ser
385                 390                 395                 400

Arg Leu Glu Ser Gly Val Pro Ser Arg Phe Ser Gly Ser Gly Ser Gly
                405                 410                 415

Thr Asp Tyr Thr Leu Thr Ile Ser Ser Leu Gln Pro Glu Asp Phe Ala
            420                 425                 430

Thr Tyr Tyr Cys Gln Gln Gly Asn Thr Leu Pro Trp Thr Phe Gly Gln
        435                 440                 445

Gly Thr Lys Val Glu Ile Lys Gly Gly Gly Gly Ser Gly Gly Gly Gly
    450                 455                 460

Ser Gly Gly Gly Gly Ser Glu Val Gln Leu Val Glu Ser Gly Gly Gly
465                 470                 475                 480

Leu Val Gln Pro Gly Gly Ser Leu Arg Leu Ser Cys Ala Ala Ser Gly
                485                 490                 495

Tyr Ser Phe Thr Gly Tyr Thr Met Asn Trp Val Arg Gln Ala Pro Gly
            500                 505                 510

Lys Gly Leu Glu Trp Val Ala Leu Ile Asn Pro Tyr Lys Gly Val Ser
        515                 520                 525

Thr Tyr Asn Gln Lys Phe Lys Asp Arg Phe Thr Ile Ser Val Asp Lys
    530                 535                 540

Ser Lys Asn Thr Ala Tyr Leu Gln Met Asn Ser Leu Arg Ala Glu Asp
545                 550                 555                 560

Thr Ala Val Tyr Tyr Cys Ala Arg Ser Gly Tyr Tyr Gly Asp Ser Asp
                565                 570                 575

Trp Tyr Phe Asp Val Trp Gly Gln Gly Thr Leu Val Thr Val Ser Ser
            580                 585                 590

<210> SEQ ID NO 19
<211> LENGTH: 588
<212> TYPE: PRT
<213> ORGANISM: Artificial Sequence
<220> FEATURE:
<223> OTHER INFORMATION: CSPG4 x TCR alpha/beta, bsFcko-1/2 [N-terminal
      anti-CSPG4 chimeric heavy chain (clone 9.2.27) and C-terminal
      anti-TCR alpha/beta single-chain (clone BMA031; VH-VL)], chain of
      a glycan-ko-variant-halfmolecule

<400> SEQUENCE: 19

Gln Val Lys Leu Gln Gln Ser Gly Pro Glu Leu Val Lys Pro Gly Ala
1               5                   10                  15

```
Ser Val Lys Ile Ser Cys Lys Ala Ser Gly Tyr Ala Phe Ser Arg Ser
            20                  25                  30

Trp Met Asn Trp Val Lys Gln Arg Pro Gly Gln Gly Leu Glu Trp Ile
            35                  40                  45

Gly Arg Ile Tyr Pro Gly Asp Gly Asp Thr Asn Tyr Asn Gly Lys Phe
 50                  55                  60

Lys Gly Lys Ala Thr Leu Thr Ala Asp Lys Ser Ser Ser Thr Ala Tyr
 65                  70                  75                  80

Met Gln Val Ser Ser Leu Thr Ser Val Asp Ser Ala Val Tyr Phe Cys
                85                  90                  95

Ala Arg Gly Asn Thr Val Val Pro Tyr Thr Met Asp Tyr Trp Gly
                100                 105                 110

Gln Gly Thr Thr Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Cys
            210                 215                 220

Asp Lys Thr His Thr Ser Pro Pro Ser Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Gly Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Gln Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gln Leu Pro Ser Pro Ile Glu
                325                 330                 335

Lys Thr Ile Ser Lys Ala Lys Gly Gln Pro Ser Gly Glu Val Gln Leu
                340                 345                 350

Gln Gln Ser Gly Pro Glu Leu Val Lys Pro Gly Ala Ser Val Lys Met
            355                 360                 365

Ser Cys Lys Ala Ser Gly Tyr Lys Phe Thr Ser Tyr Val Met His Trp
            370                 375                 380

Val Lys Gln Lys Pro Gly Gln Gly Leu Glu Trp Ile Gly Tyr Ile Asn
385                 390                 395                 400

Pro Tyr Asn Asp Val Thr Lys Tyr Asn Glu Lys Phe Lys Gly Lys Ala
                405                 410                 415

Thr Leu Thr Ser Asp Lys Ser Ser Ser Thr Ala Tyr Met Glu Leu Ser
            420                 425                 430
```

```
Ser Leu Thr Ser Glu Asp Ser Ala Val His Tyr Cys Ala Arg Gly Ser
            435                 440                 445

Tyr Tyr Asp Tyr Asp Gly Phe Val Tyr Gly Gln Gly Thr Leu Val Thr
450                 455                 460

Val Ser Ser Gly Gly Gly Gly Ser Gly Gly Gly Gly Ser Gly Gly Gly
465                 470                 475                 480

Gly Ser Gln Ile Val Leu Thr Gln Ser Pro Ala Ile Met Ser Ala Ser
                485                 490                 495

Pro Gly Glu Lys Val Thr Met Thr Cys Ser Ala Thr Ser Ser Val Ser
            500                 505                 510

Tyr Met His Trp Tyr Gln Gln Lys Ser Gly Thr Ser Pro Lys Arg Trp
            515                 520                 525

Ile Tyr Asp Thr Ser Lys Leu Ala Ser Gly Val Pro Ala Arg Phe Ser
            530                 535                 540

Gly Ser Gly Ser Gly Thr Ser Tyr Ser Leu Thr Ile Ser Ser Met Glu
545                 550                 555                 560

Ala Glu Asp Ala Ala Thr Tyr Tyr Cys Gln Gln Trp Ser Ser Asn Pro
                565                 570                 575

Leu Thr Phe Gly Ala Gly Thr Lys Leu Glu Leu Lys
                580                 585

<210> SEQ ID NO 20
<211> LENGTH: 595
<212> TYPE: PRT
<213> ORGANISM: Artificial Sequence
<220> FEATURE:
<223> OTHER INFORMATION: CSPG4 x CD28; bsFcko-1/2 [N-terminal anti-CSPG4
      chimeric heavy chain (clone 9.2.27) and C-terminal CD28 single-
      chain (clone 9.3; VL-VH)], being a chain of a glycan-ko-variant-
      halfmolecule

<400> SEQUENCE: 20

Gln Val Lys Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Arg Ser
            20                  25                  30

Trp Met Asn Trp Val Lys Gln Arg Pro Gly Gln Gly Leu Glu Trp Ile
        35                  40                  45

Gly Arg Ile Tyr Pro Gly Asp Gly Asp Thr Asn Tyr Asn Gly Lys Phe
    50                  55                  60

Lys Gly Lys Ala Thr Leu Thr Ala Asp Lys Ser Ser Ser Thr Ala Tyr
65                  70                  75                  80

Met Gln Val Ser Ser Leu Thr Ser Val Asp Ser Ala Val Tyr Phe Cys
                85                  90                  95

Ala Arg Gly Asn Thr Val Val Pro Tyr Thr Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190
```

```
Pro Ser Ser Ser Leu Gly Thr Gln Thr Tyr Ile Cys Asn Val Asn His
            195                 200                 205

Lys Pro Ser Asn Thr Lys Val Asp Lys Val Glu Pro Lys Ser Cys
210                 215                 220

Asp Lys Thr His Thr Ser Pro Pro Ser Pro Ala Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Gln Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gln Leu Pro Ser Pro Ile Glu
                325                 330                 335

Lys Thr Ile Ser Lys Ala Lys Gly Gln Pro Ser Gly Asp Ile Glu Leu
                340                 345                 350

Thr Gln Ser Pro Ala Ser Leu Ala Val Ser Leu Gly Gln Arg Ala Thr
            355                 360                 365

Ile Ser Cys Arg Ala Ser Glu Ser Val Glu Tyr Tyr Val Thr Ser Leu
            370                 375                 380

Met Gln Trp Tyr Gln Gln Lys Pro Gly Gln Pro Pro Lys Leu Leu Ile
385                 390                 395                 400

Phe Ala Ala Ser Asn Val Glu Ser Gly Val Pro Ala Arg Phe Ser Gly
                405                 410                 415

Ser Gly Ser Gly Thr Asn Phe Ser Leu Asn Ile His Pro Val Asp Glu
            420                 425                 430

Asp Asp Val Ala Met Tyr Phe Cys Gln Gln Ser Arg Lys Val Pro Tyr
            435                 440                 445

Thr Phe Gly Gly Gly Thr Lys Leu Glu Ile Lys Arg Gly Gly Gly Gly
450                 455                 460

Ser Gly Gly Gly Gly Ser Gly Gly Gly Gly Ser Gln Val Lys Leu Gln
465                 470                 475                 480

Gln Ser Gly Pro Gly Leu Val Thr Pro Ser Gln Ser Leu Ser Ile Thr
                485                 490                 495

Cys Thr Val Ser Gly Phe Ser Leu Ser Asp Tyr Gly Val His Trp Val
            500                 505                 510

Arg Gln Ser Pro Gly Gln Gly Leu Glu Trp Leu Gly Val Ile Trp Ala
            515                 520                 525

Gly Gly Gly Thr Asn Tyr Asn Ser Ala Leu Met Ser Arg Lys Ser Ile
530                 535                 540

Ser Lys Asp Asn Ser Lys Ser Gln Val Phe Leu Lys Met Asn Ser Leu
545                 550                 555                 560

Gln Ala Asp Asp Thr Ala Val Tyr Tyr Cys Ala Arg Asp Lys Gly Tyr
                565                 570                 575

Ser Tyr Tyr Tyr Ser Met Asp Tyr Trp Gly Gln Gly Thr Thr Val Thr
            580                 585                 590

Val Ser Ser
595
```

-continued

```
<210> SEQ ID NO 21
<211> LENGTH: 592
<212> TYPE: PRT
<213> ORGANISM: Artificial Sequence
<220> FEATURE:
<223> OTHER INFORMATION: CSPG4 x CD16; bsFcko-1/2 [N-terminal anti-CSPG4
      chimeric heavy chain (clone 9.2.27) and C-terminal CD16 single-
      chain (clone 3G8; VL-VH)], chain of a glycan-ko-variant-
      halfmolecule

<400> SEQUENCE: 21
```

Gln Val Lys Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Arg Ser
            20                  25                  30

Trp Met Asn Trp Val Lys Gln Arg Pro Gly Gln Gly Leu Glu Trp Ile
        35                  40                  45

Gly Arg Ile Tyr Pro Gly Asp Gly Asp Thr Asn Tyr Asn Gly Lys Phe
    50                  55                  60

Lys Gly Lys Ala Thr Leu Thr Ala Asp Lys Ser Ser Thr Ala Tyr
65                  70                  75                  80

Met Gln Val Ser Ser Leu Thr Ser Val Asp Ser Ala Val Tyr Phe Cys
                85                  90                  95

Ala Arg Gly Asn Thr Val Val Pro Tyr Thr Met Asp Tyr Trp Gly
            100                 105                 110

Gln Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Ser Pro Pro Ser Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Gly Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Gln Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gln Leu Pro Ser Pro Ile Glu
                325                 330                 335

Lys Thr Ile Ser Lys Ala Lys Gly Gln Pro Ser Gly Asp Ile Val Leu
            340                 345                 350

Thr Gln Ser Pro Ala Ser Leu Ala Val Ser Leu Gly Gln Arg Ala Thr

```
            355                 360                 365
Ile Ser Cys Lys Ala Ser Gln Ser Val Asp Phe Asp Gly Asp Ser Phe
370                 375                 380

Met Asn Trp Tyr Gln Gln Lys Pro Gly Gln Pro Pro Lys Leu Leu Ile
385                 390                 395                 400

Tyr Thr Thr Ser Asn Leu Glu Ser Gly Ile Pro Ala Arg Phe Ser Ala
                405                 410                 415

Ser Gly Ser Gly Thr Asp Phe Thr Leu Asn Ile His Pro Val Glu Glu
                420                 425                 430

Glu Asp Thr Ala Thr Tyr Tyr Cys Gln Gln Ser Asn Glu Asp Pro Tyr
            435                 440                 445

Thr Phe Gly Gly Gly Thr Lys Leu Glu Ile Lys Gly Gly Gly Gly Ser
        450                 455                 460

Gly Gly Gly Gly Ser Gly Gly Gly Ser Gln Val Thr Leu Lys Glu
465                 470                 475                 480

Ser Gly Pro Gly Ile Leu Gln Pro Ser Gln Thr Leu Ser Leu Thr Cys
                485                 490                 495

Ser Phe Ser Gly Phe Ser Leu Arg Thr Ser Gly Met Gly Val Gly Trp
                500                 505                 510

Ile Arg Gln Pro Ser Gly Lys Gly Leu Glu Trp Leu Ala His Ile Trp
            515                 520                 525

Trp Asp Asp Asp Lys Arg Tyr Asn Pro Ala Leu Lys Ser Arg Leu Thr
530                 535                 540

Ile Ser Lys Asp Thr Ser Ser Asn Gln Val Phe Leu Lys Ile Ala Ser
545                 550                 555                 560

Val Asp Thr Ala Asp Thr Ala Thr Tyr Tyr Cys Ala Gln Ile Asn Pro
                565                 570                 575

Ala Trp Phe Ala Tyr Trp Gly Gln Gly Thr Leu Val Thr Val Ser Ser
            580                 585                 590

<210> SEQ ID NO 22
<211> LENGTH: 590
<212> TYPE: PRT
<213> ORGANISM: Artificial Sequence
<220> FEATURE:
<223> OTHER INFORMATION: EGFR x CD3; bsFcko-1/2 [N-terminal anti-EGFR
      chimeric heavy chain (clone C225) and C-terminal CD3 single-chain
      (clone UCHT1; VL-VH)], chain of a glycan-ko-variant-halfmolecule

<400> SEQUENCE: 22

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser Ala Ser Thr Lys Gly Pro Ser Val Phe
        115                 120                 125
```

-continued

```
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Ser Pro Pro Ser Pro Ala Pro Pro Val Ala Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Gly Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Gln Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Gln Leu Pro Ser Pro Ile Glu Lys Thr
                325                 330                 335
Ile Ser Lys Ala Lys Gly Gln Pro Ser Gly Asp Ile Gln Met Thr Gln
            340                 345                 350
Ser Pro Ser Ser Leu Ser Ala Ser Val Gly Asp Arg Val Thr Ile Thr
        355                 360                 365
Cys Arg Ala Ser Gln Asp Ile Arg Asn Tyr Leu Asn Trp Tyr Gln Gln
    370                 375                 380
Lys Pro Gly Lys Ala Pro Lys Leu Leu Ile Tyr Tyr Thr Ser Arg Leu
385                 390                 395                 400
Glu Ser Gly Val Pro Ser Arg Phe Ser Gly Ser Gly Ser Gly Thr Asp
                405                 410                 415
Tyr Thr Leu Thr Ile Ser Ser Leu Gln Pro Glu Asp Phe Ala Thr Tyr
            420                 425                 430
Tyr Cys Gln Gln Gly Asn Thr Leu Pro Trp Thr Phe Gly Gln Gly Thr
        435                 440                 445
Lys Val Glu Ile Lys Gly Gly Gly Gly Ser Gly Gly Gly Gly Ser Gly
    450                 455                 460
Gly Gly Gly Ser Glu Val Gln Leu Val Glu Ser Gly Gly Gly Leu Val
465                 470                 475                 480
Gln Pro Gly Gly Ser Leu Arg Leu Ser Cys Ala Ala Ser Gly Tyr Ser
                485                 490                 495
Phe Thr Gly Tyr Thr Met Asn Trp Val Arg Gln Ala Pro Gly Lys Gly
            500                 505                 510
Leu Glu Trp Val Ala Leu Ile Asn Pro Tyr Lys Gly Val Ser Thr Tyr
        515                 520                 525
Asn Gln Lys Phe Lys Asp Arg Phe Thr Ile Ser Val Asp Lys Ser Lys
    530                 535                 540
```

-continued

Asn Thr Ala Tyr Leu Gln Met Asn Ser Leu Arg Ala Glu Asp Thr Ala
545                 550                 555                 560

Val Tyr Tyr Cys Ala Arg Ser Gly Tyr Tyr Gly Asp Ser Asp Trp Tyr
            565                 570                 575

Phe Asp Val Trp Gly Gln Gly Thr Leu Val Thr Val Ser Ser
        580                 585                 590

<210> SEQ ID NO 23
<211> LENGTH: 586
<212> TYPE: PRT
<213> ORGANISM: Artificial Sequence
<220> FEATURE:
<223> OTHER INFORMATION: EGFR x TCR alpha/beta; bsFcko-1/2 [N-terminal
      anti-EGFR chimeric heavy chain (clone C225) and C-terminal TCR
      alpha/beta single-chain (clone BMA031; VH-VL)], chain of a glycan-
      ko-variant-halfmolecule

<400> SEQUENCE: 23

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
                20                  25                  30

Gly Val His Trp Val Arg Gln Ser Pro Gly Lys Gly Leu Glu Trp Leu
            35                  40                  45

Gly Val Ile Trp Ser Gly Gly Asn Thr Asp Tyr Asn Thr Pro Phe Thr
        50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Ser Pro Pro Ser Pro Ala Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Gly Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Gln Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Gln Leu Pro Ser Pro Ile Glu Lys Thr
                325                 330                 335

Ile Ser Lys Ala Lys Gly Gln Pro Ser Gly Glu Val Gln Leu Gln Gln
            340                 345                 350

Ser Gly Pro Glu Leu Val Lys Pro Gly Ala Ser Val Lys Met Ser Cys
        355                 360                 365

Lys Ala Ser Gly Tyr Lys Phe Thr Ser Tyr Val Met His Trp Val Lys
    370                 375                 380

Gln Lys Pro Gly Gln Gly Leu Glu Trp Ile Gly Tyr Ile Asn Pro Tyr
385                 390                 395                 400

Asn Asp Val Thr Lys Tyr Asn Glu Lys Phe Lys Gly Lys Ala Thr Leu
                405                 410                 415

Thr Ser Asp Lys Ser Ser Ser Thr Ala Tyr Met Glu Leu Ser Ser Leu
            420                 425                 430

Thr Ser Glu Asp Ser Ala Val His Tyr Cys Ala Arg Gly Ser Tyr Tyr
        435                 440                 445

Asp Tyr Asp Gly Phe Val Tyr Gly Gln Gly Thr Leu Val Thr Val Ser
    450                 455                 460

Ser Gly Gly Gly Gly Ser Gly Gly Gly Gly Ser Gly Gly Gly Gly Ser
465                 470                 475                 480

Gln Ile Val Leu Thr Gln Ser Pro Ala Ile Met Ser Ala Ser Pro Gly
                485                 490                 495

Glu Lys Val Thr Met Thr Cys Ser Ala Thr Ser Ser Val Ser Tyr Met
            500                 505                 510

His Trp Tyr Gln Gln Lys Ser Gly Thr Ser Pro Lys Arg Trp Ile Tyr
        515                 520                 525

Asp Thr Ser Lys Leu Ala Ser Gly Val Pro Ala Arg Phe Ser Gly Ser
    530                 535                 540

Gly Ser Gly Thr Ser Tyr Ser Leu Thr Ile Ser Ser Met Glu Ala Glu
545                 550                 555                 560

Asp Ala Ala Thr Tyr Tyr Cys Gln Gln Trp Ser Ser Asn Pro Leu Thr
                565                 570                 575

Phe Gly Ala Gly Thr Lys Leu Glu Leu Lys
            580                 585

<210> SEQ ID NO 24
<211> LENGTH: 593
<212> TYPE: PRT
<213> ORGANISM: Artificial Sequence
<220> FEATURE:
<223> OTHER INFORMATION: EGFR x CD28; bsFcko-1/2 [N-terminal anti-EGFR
      chimeric heavy chain (clone C225) and C-terminal CD28 single-chain
      (clone 9.3; VL-VH)], chain of a glycan-ko-variant-halfmolecule

<400> SEQUENCE: 24

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe

-continued

```
             65                  70                  75                  80
Lys Met Asn Ser Leu Gln Ser Asn Asp Thr Ala Ile Tyr Tyr Cys Ala
                    85                  90                  95
Arg Ala Leu Thr Tyr Tyr Asp Tyr Glu Phe Ala Tyr Trp Gly Gln Gly
                    100                 105                 110
Thr Leu Val Thr Val Ser Ser Ala Ser Thr Lys Gly Pro Ser Val Phe
                    115                 120                 125
Pro Leu Ala Pro Ser Ser Lys Ser Thr Ser Gly Gly Thr Ala Ala Leu
                    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                    165                 170                 175
Gln Ser Ser Gly Leu Tyr Ser Leu Ser Ser Val Val Thr Val Pro Ser
                    180                 185                 190
Ser Ser Leu Gly Thr Gln Thr Tyr Ile Cys Asn Val Asn His Lys Pro
                    195                 200                 205
Ser Asn Thr Lys Val Asp Lys Lys Val Glu Pro Lys Ser Cys Asp Lys
                    210                 215                 220
Thr His Thr Ser Pro Pro Ser Pro Ala Pro Pro Val Ala Gly Pro Ser
225                 230                 235                 240
Val Phe Leu Phe Pro Pro Lys Pro Lys Asp Thr Leu Met Ile Ser Arg
                    245                 250                 255
Thr Pro Glu Val Thr Cys Val Val Val Gly Val Ser His Glu Asp Pro
                    260                 265                 270
Glu Val Lys Phe Asn Trp Tyr Val Asp Gly Val Glu Val His Asn Ala
                    275                 280                 285
Lys Thr Lys Pro Arg Glu Glu Gln Tyr Gln Ser Thr Tyr Arg Val Val
                    290                 295                 300
Ser Val Leu Thr Val Leu His Gln Asp Trp Leu Asn Gly Lys Glu Tyr
305                 310                 315                 320
Lys Cys Lys Val Ser Asn Lys Gln Leu Pro Ser Pro Ile Glu Lys Thr
                    325                 330                 335
Ile Ser Lys Ala Lys Gly Gln Pro Ser Gly Asp Ile Glu Leu Thr Gln
                    340                 345                 350
Ser Pro Ala Ser Leu Ala Val Ser Leu Gly Gln Arg Ala Thr Ile Ser
                    355                 360                 365
Cys Arg Ala Ser Glu Ser Val Glu Tyr Tyr Val Thr Ser Leu Met Gln
                    370                 375                 380
Trp Tyr Gln Gln Lys Pro Gly Gln Pro Pro Lys Leu Leu Ile Phe Ala
385                 390                 395                 400
Ala Ser Asn Val Glu Ser Gly Val Pro Ala Arg Phe Ser Gly Ser Gly
                    405                 410                 415
Ser Gly Thr Asn Phe Ser Leu Asn Ile His Pro Val Asp Glu Asp Asp
                    420                 425                 430
Val Ala Met Tyr Phe Cys Gln Gln Ser Arg Lys Val Pro Tyr Thr Phe
                    435                 440                 445
Gly Gly Gly Thr Lys Leu Glu Ile Lys Arg Gly Gly Gly Gly Ser Gly
                    450                 455                 460
Gly Gly Gly Ser Gly Gly Gly Gly Ser Gln Val Lys Leu Gln Gln Ser
465                 470                 475                 480
Gly Pro Gly Leu Val Thr Pro Ser Gln Ser Leu Ser Ile Thr Cys Thr
                    485                 490                 495
```

Val Ser Gly Phe Ser Leu Ser Asp Tyr Gly Val His Trp Val Arg Gln
            500                 505                 510

Ser Pro Gly Gln Gly Leu Glu Trp Leu Gly Val Ile Trp Ala Gly Gly
            515                 520                 525

Gly Thr Asn Tyr Asn Ser Ala Leu Met Ser Arg Lys Ser Ile Ser Lys
            530                 535                 540

Asp Asn Ser Lys Ser Gln Val Phe Leu Lys Met Asn Ser Leu Gln Ala
545                 550                 555                 560

Asp Asp Thr Ala Val Tyr Tyr Cys Ala Arg Asp Lys Gly Tyr Ser Tyr
                565                 570                 575

Tyr Tyr Ser Met Asp Tyr Trp Gly Gln Gly Thr Thr Val Thr Val Ser
            580                 585                 590

Ser

<210> SEQ ID NO 25
<211> LENGTH: 590
<212> TYPE: PRT
<213> ORGANISM: Artificial Sequence
<220> FEATURE:
<223> OTHER INFORMATION: EGFR x CD16; bsFcko-1/2 [N-terminal anti-EGFR
      chimeric heavy chain (clone C225) and C-terminal CD16 single-chain
      (clone 3G8; VL-VH)], chain of a glycan-ko-variant-halfmolecule

<400> SEQUENCE: 25

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Ser Pro Pro Ser Pro Ala Pro Val Ala Gly Pro Ser
225                 230                 235                 240

Val Phe Leu Phe Pro Pro Lys Pro Lys Asp Thr Leu Met Ile Ser Arg

```
                    245                 250                 255
Thr Pro Glu Val Thr Cys Val Val Gly Val Ser His Glu Asp Pro
                260                 265                 270
Glu Val Lys Phe Asn Trp Tyr Val Asp Gly Val Glu Val His Asn Ala
            275                 280                 285
Lys Thr Lys Pro Arg Glu Glu Gln Tyr Gln Ser Thr Tyr Arg Val Val
        290                 295                 300
Ser Val Leu Thr Val Leu His Gln Asp Trp Leu Asn Gly Lys Glu Tyr
305                 310                 315                 320
Lys Cys Lys Val Ser Asn Lys Gln Leu Pro Ser Pro Ile Glu Lys Thr
                325                 330                 335
Ile Ser Lys Ala Lys Gly Gln Pro Ser Gly Asp Ile Val Leu Thr Gln
            340                 345                 350
Ser Pro Ala Ser Leu Ala Val Ser Leu Gly Gln Arg Ala Thr Ile Ser
        355                 360                 365
Cys Lys Ala Ser Gln Ser Val Asp Phe Asp Gly Asp Ser Phe Met Asn
    370                 375                 380
Trp Tyr Gln Gln Lys Pro Gly Gln Pro Pro Lys Leu Leu Ile Tyr Thr
385                 390                 395                 400
Thr Ser Asn Leu Glu Ser Gly Ile Pro Ala Arg Phe Ser Ala Ser Gly
                405                 410                 415
Ser Gly Thr Asp Phe Thr Leu Asn Ile His Pro Val Glu Glu Asp
            420                 425                 430
Thr Ala Thr Tyr Tyr Cys Gln Gln Ser Asn Glu Asp Pro Tyr Thr Phe
        435                 440                 445
Gly Gly Gly Thr Lys Leu Glu Ile Lys Gly Gly Gly Gly Ser Gly Gly
    450                 455                 460
Gly Gly Ser Gly Gly Gly Gly Ser Gln Val Thr Leu Lys Glu Ser Gly
465                 470                 475                 480
Pro Gly Ile Leu Gln Pro Ser Gln Thr Leu Ser Leu Thr Cys Ser Phe
                485                 490                 495
Ser Gly Phe Ser Leu Arg Thr Ser Gly Met Gly Val Gly Trp Ile Arg
            500                 505                 510
Gln Pro Ser Gly Lys Gly Leu Glu Trp Leu Ala His Ile Trp Trp Asp
        515                 520                 525
Asp Asp Lys Arg Tyr Asn Pro Ala Leu Lys Ser Arg Leu Thr Ile Ser
    530                 535                 540
Lys Asp Thr Ser Ser Asn Gln Val Phe Leu Lys Ile Ala Ser Val Asp
545                 550                 555                 560
Thr Ala Asp Thr Ala Thr Tyr Tyr Cys Ala Gln Ile Asn Pro Ala Trp
                565                 570                 575
Phe Ala Tyr Trp Gly Gln Gly Thr Leu Val Thr Val Ser Ser
            580                 585                 590
```

<210> SEQ ID NO 26
<211> LENGTH: 693
<212> TYPE: PRT
<213> ORGANISM: Artificial Sequence
<220> FEATURE:
<223> OTHER INFORMATION: heavy chain/main chain sequence, FLT3 x CD3;
      bsFcko-1 [N-terminal anti-FLT3 chimeric heavy chain and C-terminal
      CD3 single-chain (clone UCHT1; VL-VH)]: being a chain of a ko-
      variant-(full) molecule that includes a CH3 domain, not a
      glycomutant

<400> SEQUENCE: 26

-continued

```
Gln Val Gln Leu Gln Gln Pro Gly Ala Glu Leu Val Lys Pro Gly
1               5                   10                  15

Ala Ser Leu Lys Leu Ser Cys Lys Ser Ser Gly Tyr Thr Phe Thr
            20                  25                  30

Ser Tyr Trp Met His Trp Val Arg Gln Arg Pro Gly His Gly Leu
        35                  40                  45

Glu Trp Ile Gly Glu Ile Asp Pro Ser Asp Ser Tyr Lys Asp Tyr
            50                  55                  60

Asn Gln Lys Phe Lys Asp Lys Ala Thr Leu Thr Val Asp Arg Ser
            65                  70                  75

Ser Asn Thr Ala Tyr Met His Leu Ser Ser Leu Thr Ser Asp Asp
            80                  85                  90

Ser Ala Val Tyr Tyr Cys Ala Arg Ala Ile Thr Thr Thr Pro Phe
            95                  100                 105

Asp Phe Trp Gly Gln Gly Thr Thr Leu Thr Val Ser Ser Ala Ser
            110                 115                 120

Thr Lys Gly Pro Ser Val Phe Pro Leu Ala Pro Ser Ser Lys Ser
            125                 130                 135

Thr Ser Gly Gly Thr Ala Ala Leu Gly Cys Leu Val Lys Asp Tyr
            140                 145                 150

Phe Pro Glu Pro Val Thr Val Ser Trp Asn Ser Gly Ala Leu Thr
            155                 160                 165

Ser Gly Val His Thr Phe Pro Ala Val Leu Gln Ser Ser Gly Leu
            170                 175                 180

Tyr Ser Leu Ser Ser Val Val Thr Val Pro Ser Ser Ser Leu Gly
            185                 190                 195

Thr Gln Thr Tyr Ile Cys Asn Val Asn His Lys Pro Ser Asn Thr
            200                 205                 210

Lys Val Asp Lys Lys Val Glu Pro Lys Ser Cys Asp Lys Thr His
            215                 220                 225

Thr Cys Pro Pro Cys Pro Ala Pro Pro Val Ala Gly Pro Ser Val
            230                 235                 240

Phe Leu Phe Pro Pro Lys Pro Lys Asp Thr Leu Met Ile Ser Arg
            245                 250                 255

Thr Pro Glu Val Thr Cys Val Val Val Gly Val Ser His Glu Asp
            260                 265                 270

Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn
            305                 310                 315

Gly Lys Glu Tyr Lys Cys Lys Val Ser Asn Lys Gln Leu Pro Ser
            320                 325                 330

Pro Ile Glu Lys Thr Ile Ser Lys Ala Lys Gly Gln Pro Arg Glu
            335                 340                 345

Pro Gln Val Tyr Thr Leu Pro Pro Ser Arg Asp Glu Leu Thr Lys
            350                 355                 360

Asn Gln Val Ser Leu Thr Cys Leu Val Lys Gly Phe Tyr Pro Ser
            365                 370                 375

Asp Ile Ala Val Glu Trp Glu Ser Asn Gly Gln Pro Glu Asn Asn
            380                 385                 390

Tyr Lys Thr Thr Pro Pro Val Leu Asp Ser Asp Gly Ser Phe Phe
```

395                 400                 405

Leu Tyr Ser Lys Leu Thr Val Asp Lys Ser Arg Trp Gln Gln Gly
            410                 415                 420

Asn Val Phe Ser Cys Ser Val Met His Glu Ala Leu His Asn His
            425                 430                 435

Tyr Thr Gln Lys Ser Leu Ser Leu Ser Pro Gly Lys Ser Gly Asp
            440                 445                 450

Ile Gln Met Thr Gln Ser Pro Ser Ser Leu Ser Ala Ser Val Gly
            455                 460                 465

Asp Arg Val Thr Ile Thr Cys Arg Ala Ser Gln Asp Ile Arg Asn
            470                 475                 480

Tyr Leu Asn Trp Tyr Gln Gln Lys Pro Gly Lys Ala Pro Lys Leu
            485                 490                 495

Leu Ile Tyr Tyr Thr Ser Arg Leu Glu Ser Gly Val Pro Ser Arg
            500                 505                 510

Phe Ser Gly Ser Gly Ser Gly Thr Asp Tyr Thr Leu Thr Ile Ser
            515                 520                 525

Ser Leu Gln Pro Glu Asp Phe Ala Thr Tyr Tyr Cys Gln Gln Gly
            530                 535                 540

Asn Thr Leu Pro Trp Thr Phe Gly Gln Gly Thr Lys Val Glu Ile
            545                 550                 555

Lys Gly Gly Gly Gly Ser Gly Gly Gly Ser Gly Gly Gly Gly
            560                 565                 570

Ser Glu Val Gln Leu Val Glu Ser Gly Gly Leu Val Gln Pro
            575                 580                 585

Gly Gly Ser Leu Arg Leu Ser Cys Ala Ala Ser Gly Tyr Ser Phe
            590                 595                 600

Thr Gly Tyr Thr Met Asn Trp Val Arg Gln Ala Pro Gly Lys Gly
            605                 610                 615

Leu Glu Trp Val Ala Leu Ile Asn Pro Tyr Lys Gly Val Ser Thr
            620                 625                 630

Tyr Asn Gln Lys Phe Lys Asp Arg Phe Thr Ile Ser Val Asp Lys
            635                 640                 645

Ser Lys Asn Thr Ala Tyr Leu Gln Met Asn Ser Leu Arg Ala Glu
            650                 655                 660

Asp Thr Ala Val Tyr Tyr Cys Ala Arg Ser Gly Tyr Tyr Gly Asp
            665                 670                 675

Ser Asp Trp Tyr Phe Asp Val Trp Gly Gln Gly Thr Leu Val Thr
            680                 685                 690

Val Ser Ser

<210> SEQ ID NO 27
<211> LENGTH: 49
<212> TYPE: DNA
<213> ORGANISM: Artificial Sequence
<220> FEATURE:
<223> OTHER INFORMATION: oligonucleotide for hc VDJ segment

<400> SEQUENCE: 27
ctcttcacag gtgtcctctc tgaggtccag ctgcagcagt ctggacctg         49

<210> SEQ ID NO 28
<211> LENGTH: 59
<212> TYPE: DNA
<213> ORGANISM: Artificial Sequence
<220> FEATURE:

-continued

<223> OTHER INFORMATION: oligonucleotide for hc VDJ segment

<400> SEQUENCE: 28
gggagaaggt aggactcacc tgaggagact gtgagagtgg tgccttggcc ccagtagtc    59

<210> SEQ ID NO 29
<211> LENGTH: 51
<212> TYPE: DNA
<213> ORGANISM: Artificial Sequence
<220> FEATURE:
<223> OTHER INFORMATION: oligonucleotide for hc VDJ segment

<400> SEQUENCE: 29
tcttcacagg tgtcctctcc caggtgaagc tgcagcaatc tggacctgag c    51

<210> SEQ ID NO 30
<211> LENGTH: 51
<212> TYPE: DNA
<213> ORGANISM: Artificial Sequence
<220> FEATURE:
<223> OTHER INFORMATION: oligonucleotide for hc VDJ segment

<400> SEQUENCE: 30
aatgggagaa ggtaggactc acctgaggag acggtgaccg tggtcccttg g    51

<210> SEQ ID NO 31
<211> LENGTH: 53
<212> TYPE: DNA
<213> ORGANISM: Artificial Sequence
<220> FEATURE:
<223> OTHER INFORMATION: oligonucleotide for hc VDJ segment

<400> SEQUENCE: 31
tctcttcaca ggtgtcctct ctcaggtcca actgcagcag cctggggctg agc    53

<210> SEQ ID NO 32
<211> LENGTH: 52
<212> TYPE: DNA
<213> ORGANISM: Artificial Sequence
<220> FEATURE:
<223> OTHER INFORMATION: oligonucleotide for hc VDJ segment

<400> SEQUENCE: 32
gagaaggtag gactcacctg aggagactgt gagagtggtg ccttggcccc ag    52

<210> SEQ ID NO 33
<211> LENGTH: 60
<212> TYPE: DNA
<213> ORGANISM: Artificial Sequence
<220> FEATURE:
<223> OTHER INFORMATION: oligonucleotide for hc VDJ segment

<400> SEQUENCE: 33
agacgtccac tctgtctttc tcttcacagg tgtcctctcc caggtgcagc tgaagcagtc    60

<210> SEQ ID NO 34
<211> LENGTH: 49
<212> TYPE: DNA
<213> ORGANISM: Artificial Sequence
<220> FEATURE:
<223> OTHER INFORMATION: oligonucleotide for hc VDJ segment

<400> SEQUENCE: 34
gagaaggtag gactcacctg aggagacggt gactgaggtt ccttgaccc    49

```
<210> SEQ ID NO 35
<211> LENGTH: 40
<212> TYPE: DNA
<213> ORGANISM: Artificial Sequence
<220> FEATURE:
<223> OTHER INFORMATION: oligonucleotide for hc VDJ segment

<400> SEQUENCE: 35
agacgtccac tctgtctttc tcttcacagg tgtcctctcc                                    40

<210> SEQ ID NO 36
<211> LENGTH: 40
<212> TYPE: DNA
<213> ORGANISM: Artificial Sequence
<220> FEATURE:
<223> OTHER INFORMATION: oligonucleotide for hc VDJ segment

<400> SEQUENCE: 36
agacgtccac tctgtctttc tcttcacagg tgtcctctcc                                    40

<210> SEQ ID NO 37
<211> LENGTH: 43
<212> TYPE: DNA
<213> ORGANISM: Artificial Sequence
<220> FEATURE:
<223> OTHER INFORMATION: oligonucleotide for lc VJ segment

<400> SEQUENCE: 37
actcgaggag atattgtgat gactcaggct gcaccctcta tac                                43

<210> SEQ ID NO 38
<211> LENGTH: 48
<212> TYPE: DNA
<213> ORGANISM: Artificial Sequence
<220> FEATURE:
<223> OTHER INFORMATION: oligonucleotide for lc VJ segment

<400> SEQUENCE: 38
aactagtact tacgtttcag ctccagcttg gtcccagcac cgaacgtg                           48

<210> SEQ ID NO 39
<211> LENGTH: 42
<212> TYPE: DNA
<213> ORGANISM: Artificial Sequence
<220> FEATURE:
<223> OTHER INFORMATION: oligonucleotide for lc VJ segment

<400> SEQUENCE: 39
tctcgaggag acatcgagct cactcagtct ccagcttctt tg                                 42

<210> SEQ ID NO 40
<211> LENGTH: 46
<212> TYPE: DNA
<213> ORGANISM: Artificial Sequence
<220> FEATURE:
<223> OTHER INFORMATION: oligonucleotide for lc VJ segment

<400> SEQUENCE: 40
aactagtact tacgtttgat ctccagcttg gtgcccnctc caaagg                             46

<210> SEQ ID NO 41
<211> LENGTH: 42
<212> TYPE: DNA
<213> ORGANISM: Artificial Sequence
<220> FEATURE:
<223> OTHER INFORMATION: oligonucleotide for lc VJ segment
```

```
<400> SEQUENCE: 41
actcgaggag atattgtgct aactcagtct ccagccaccc tg                  42

<210> SEQ ID NO 42
<211> LENGTH: 41
<212> TYPE: DNA
<213> ORGANISM: Artificial Sequence
<220> FEATURE:
<223> OTHER INFORMATION: oligonucleotide for lc VJ segment

<400> SEQUENCE: 42
tactagtact tacgttttat ttccagcttg gtccccctc c                    41

<210> SEQ ID NO 43
<211> LENGTH: 40
<212> TYPE: DNA
<213> ORGANISM: Artificial Sequence
<220> FEATURE:
<223> OTHER INFORMATION: oligonucleotide for lc VJ segment

<400> SEQUENCE: 43
actcgaggag acattgtgat gacacagtct ccatcctccc                     40

<210> SEQ ID NO 44
<211> LENGTH: 47
<212> TYPE: DNA
<213> ORGANISM: Artificial Sequence
<220> FEATURE:
<223> OTHER INFORMATION: oligonucleotide for lc VJ segment

<400> SEQUENCE: 44
actagtactt acgtttcagc tccagcttgg tcccagcacc gaacgtg             47

<210> SEQ ID NO 45
<211> LENGTH: 40
<212> TYPE: DNA
<213> ORGANISM: Artificial Sequence
<220> FEATURE:
<223> OTHER INFORMATION: oligonucleotide for scFv segment

<400> SEQUENCE: 45
atccggagat atccagatga cccagtcccc gagctccctg                     40

<210> SEQ ID NO 46
<211> LENGTH: 45
<212> TYPE: DNA
<213> ORGANISM: Artificial Sequence
<220> FEATURE:
<223> OTHER INFORMATION: oligonucleotide for scFv segment

<400> SEQUENCE: 46
tactagttat cacgaggaga cggtgaccag ggttccttga cccca               45

<210> SEQ ID NO 47
<211> LENGTH: 39
<212> TYPE: DNA
<213> ORGANISM: Artificial Sequence
<220> FEATURE:
<223> OTHER INFORMATION: oligonucleotide for scFv segment

<400> SEQUENCE: 47
atccggagaa gtgcagctgc agcagtccgg ccctgagct                      39

<210> SEQ ID NO 48
<211> LENGTH: 45
```

```
<212> TYPE: DNA
<213> ORGANISM: Artificial Sequence
<220> FEATURE:
<223> OTHER INFORMATION: oligonucleotide for scFv segment

<400> SEQUENCE: 48
tactagttat cacttcagtt ccagcttggt gccagcgccg aaggt            45

<210> SEQ ID NO 49
<211> LENGTH: 41
<212> TYPE: DNA
<213> ORGANISM: Artificial Sequence
<220> FEATURE:
<223> OTHER INFORMATION: oligonucleotide for scFv segment

<400> SEQUENCE: 49
atccggagac attgtgctga cccagtcccc tgcctccctg g                41

<210> SEQ ID NO 50
<211> LENGTH: 45
<212> TYPE: DNA
<213> ORGANISM: Artificial Sequence
<220> FEATURE:
<223> OTHER INFORMATION: oligonucleotide for scFv segment

<400> SEQUENCE: 50
tactagttat caagagctca cagtcactgt ggtgccctgg cccca            45
```